US006451314B1

(12) United States Patent
Clark et al.

(10) Patent No.: US 6,451,314 B1
(45) Date of Patent: *Sep. 17, 2002

(54) MHC CONJUGATES USEFUL IN AMELIORATING AUTOIMMUNITY

(75) Inventors: Brian R. Clark, Redwood City; Somesh D. Sharma, Los Altos; Bernard L. Lerch, Palo Alto, all of CA (US)

(73) Assignee: Anergen, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/602,807

(22) Filed: Jun. 23, 2000

Related U.S. Application Data

(63) Continuation of application No. 08/462,351, filed on Jun. 5, 1995, now Pat. No. 6,106,840, which is a division of application No. 07/869,293, filed on Apr. 14, 1992, now Pat. No. 5,468,481, which is a continuation-in-part of application No. 07/690,840, filed on Apr. 23, 1991, now Pat. No. 5,260,422, which is a continuation-in-part of application No. 07/576,084, filed on Aug. 30, 1990, now Pat. No. 5,130,297, which is a continuation of application No. 07/210,594, filed on Jun. 23, 1988, now abandoned.

(51) Int. Cl.$^7$ .............................................. A61K 39/00

(52) U.S. Cl. .................................. 424/185.1; 424/193.1

(58) Field of Search ................................ 530/403, 402, 530/868; 424/88, 185.1, 193.1

(56) References Cited

U.S. PATENT DOCUMENTS

| | | | |
|---|---|---|---|
| 4,675,382 A | | 6/1987 | Murphy |
| 4,714,759 A | | 12/1987 | Whitaker |
| 5,130,297 A | * | 7/1992 | Sharma et al. |
| 5,260,422 A | * | 11/1993 | Clark et al. |
| 5,284,935 A | * | 2/1994 | Clark et al. |
| 5,468,481 A | * | 11/1995 | Sharma et al. |
| 5,820,866 A | * | 10/1998 | Kappler et al. |
| 6,106,840 A | * | 8/2000 | Clark et al. |

FOREIGN PATENT DOCUMENTS

| | | |
|---|---|---|
| WO | WO 88/00057 | 1/1988 |
| WO | WO 89/12458 | 12/1989 |
| WO | WO 90/14835 | 12/1990 |

OTHER PUBLICATIONS

Quill and Schwartz Journal of Immunology 138:3704–3712, 1987.*
Babbitt, B.P. et al. (1985) *Nature* 317: 359–361.
Bjorkman, P.J. et al. (1987) *Nature* 329: 506–512.
Bjorkman, P.J. et al. (1987) *Nature* 329: 512–518.
Buus, S. et al. (1987) *Science* 235: 1353–1358.
Diener, E. et al. (1986) *Science* 231: 148–150.
Killen, J.A. et al. (1984) *J. Immunol.* 133: 2549–2553.
Livingstone, A.M. et al. (1987) *Ann. Rev. Immunol.* 5: 477–501.
Marx, J.L. (1987) *Science* 238: 613–614.
Paul, W.E. (1989) *Fundamental Immunol.* Raven Press, New York, pp. 69–73.
Puri, J. et al. (1980) *Eur. J. Immunol.* 10: 273–281.
Rennie, D.P. et al. (1983) *The Lancet* (Dec. 10) 1338–1340.
Sterz, R.K.M. et al. (1985) *J. Immunol.* 134: 841–846.
Townsend, A. et al. (1987) *Nature* 329: 482–483.
Turkewitz, A.P. et al. (1983) *Molec. Immunol.* 20: 1139–1147.
Unanue, E.R. et al. (1987) *Science* 236: 551–557.
Watts, T.H. et al. (1984) *Proc. Natl. Acad. Sci. USA* 81: 7564–7568.
Watts, T.H. et al. (1985) *Proc. Natl. Acad. Sci. USA* 82: 5480–5484.
Watts, T.H. et al. (1987) *Ann. Rev. Immunol.* 5: 461–475.
Clemetson, K.J. et al. (1986) In *Membrane proteins: A Laboratory Manual*, Ed. Azzi, A. et al., pp. 57–64.
Cooperman (1979) In *Ribosomes Structure, Function, and Genetics.* Ed. Chambliss et al. University Park Press, Baltimore MD. pp. 531–554.
Estess, P. et al. (1986) In *Regulation of immune gene expression*, Ed. Feldman, M. et al., Humana Press, pp. 3–19.
Guillet et al. (1987) *Science* 235: 865–870.
Hall et al. (1985) *Biochemistry* 24: 5702–5711.
Harcourt, G. et al. (1987) *Immunol. Today* 8 (11): (news and features section).
Liu, M.A. et al. (1988) *Science* 239: 395–398.
Marrack, P. et al. (1988) *Nature* 332: 840–842.
Nakanishi, M. et al. (1983) *Molec. Immunol.* 20: 1227–1231.
Pastan, I. et al. (1986) *Cell* 47: 641–648.
Sekaly, R.P. et al. (1986) *J. Exp. Med.* 164: 1490–1504.
Shizuru, J.A. et al. (1988) *Science* 240: 659–662.
Springer, T.A. et al. (1976) *Proc. Natl. Acad. Sci. USA* 73: 2481–2485.
Sriram, S. et al. (1987) *Concepts Immunopathol.* 4: 275–286.
Vitetta, E.S. et al. (1987) *Science* 238: 1098–1104.
Watts, T.H. et al. (1988) In *Processing and presentation of antigens*, Academic Press, pp. 143–154.
Binz, H. et al. (1979) *J. Exp. Med.* 150: 1084–1097.
Gasciogne, N.R.J. et al. (1987) *Proc. Natl. Acad. Sci. USA.* 84: 2396–2340.
Margulies, D.H. et al. (1987) *Immunol. Res.* 6: 101–116.
McCluskey, J. et al. (1988) *J. Immunol.* 141: 1451–1455.
Lamb et al. (1987) *EMBO J.* 6: 1245–1249.
Berkower et al. (1986) *J. Immunol.* 136: 2498–2502.
Townsend et al. (1986) *Cell* 44: 959–968.
Sanderson et al. (1973) *Transplantation* 16: 304–312.
Turner et al. (1976) *J. Biol. Chem.* 250: 4512–4519.

(List continued on next page.)

*Primary Examiner*—David Saunders
*Assistant Examiner*—Amy DeCloux
(74) *Attorney, Agent, or Firm*—Townsend and Townsend and Crew LLP

(57) ABSTRACT

The present invention is directed to complexes consisting essentially of an isolated MHC component and an autoantigenic peptide associated with the antigen binding site of the MHC component. These complexes are useful in treating autoimmune disease.

10 Claims, 26 Drawing Sheets

OTHER PUBLICATIONS

Gorga et al. (1987) *J. Biol. Chem.* 262: 16087–16094.
Zamvil et al. (1985) *J. Exp. Med.* 162: 2107–2124.
Zamvil et al. (1985) *Nature* 317: 355–358.
Ceredig, R. et al. (1986) *Eur. J. Immunol.* 16: 30–34.
Essery, G. et al. (1988) *Immunology* 64: 413–417.
Jenkins, M.K. et al. (1987) *J. Exp. Med.* 165: 302–319.
Klein, J. (1984) *Immunol. Reviews* 81: 177–202.
Lamb, J.R. (1983) *J. Exp. Med.* 157: 1434–1447.
Lamb, J.R. (1984) *Nature* 308: 72–74.
Lamb, J.R. et al. (1986) *Immunology* 57: 331–335.
Lamb, J.R. et al. (1987) *Eur. J. Immunol.* 17: 1641–1644.
Larche, M. et al. (1988) *Immunology* 64: 101–105.
Madsen, J.C. et al. (1988) *Nature* 332: 161–164.
Miller, S.D. et al. (1979) *J. Exp. Med.* 149: 758–773.
Nau, G.J. et al. (1987) *J. Immunol.* 139: 114–122.
Quill, H. et al. (1987) *J. Immunol.* 138: 3704–3712.
Suzuki, G. et al. (1988) *J. Immunol.* 140: 1359–1365.
Zanders, E.D. et al. (1983) *Nature* 303: 625–627.
Zanders, E.D. et al. (1985) *Eur. J. Immunol.* 15: 302–305.
Germain, R.N. (1981) *J. Immunol.* 127:1964–1966.
Lamb, J.R. et al. (1987) *EMBO J.* 6:1245–1249.
Buss, S. et al. (1988) *Science* 242:1045–1047.
Sharma, S.D. et al. (1991) *Proc. Natl. Acad. Sci. USA* 88:11465–11469.
Nag, B. et al. (1992) *J. of Immunol.* 148(7):2040–2044.
Nag, B. et al. (1992) *J. of Immunol.* 148(2):369–372.
Nag, B. et al. (1991) *J. of Immunological Methods* 142:105–111.

* cited by examiner

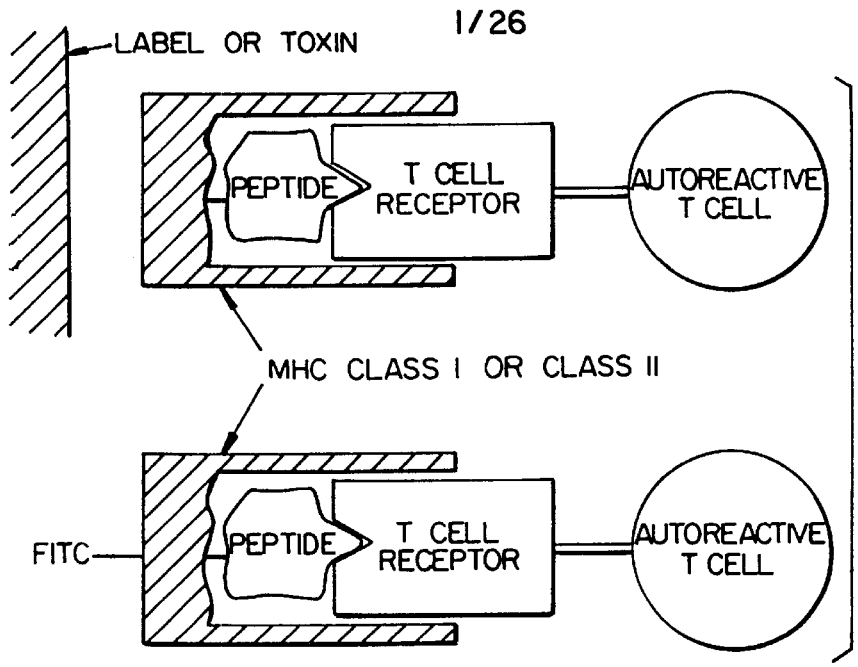
FIG. 1.
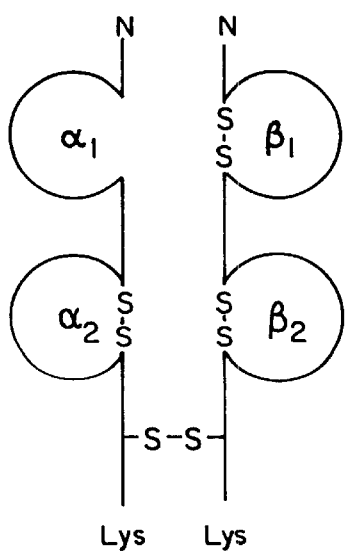
FIG. 3.
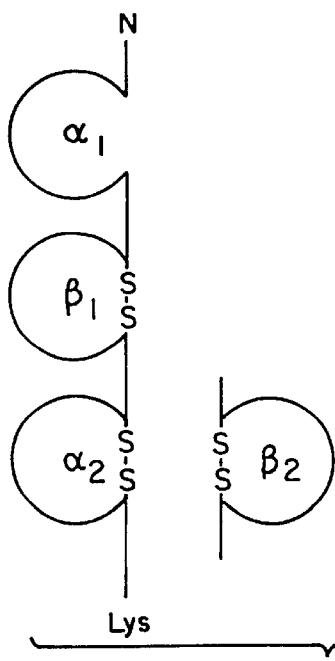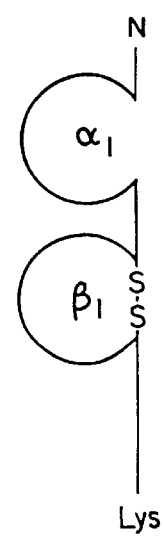
FIG. 4.

```
Leu Leu Leu Phe Ser Cys Cys Gly Leu Val Leu Gly Ser Glu His Glu Thr Arg
CUA CUG UUA UUU UCG UGU UGU GGU CUG GUA CUA GGU UCU GAA CAU GAA ACA CGU
            10              -20                      -1 -1
                                                        1
Leu Val Ala Asn Leu Leu Glu Asn Tyr Asn Lys Val Ile Arg Pro Val Glu His
UUG GUU GCU AAU UUA GAA AAU UAU AAC AAG GUG AUU CGU CCA GUG GAG CAU
    20              40                      20              60
His Thr His Phe Val Asp Ile Thr Val Gly Leu Gln Leu Ile Gln Leu Ile Ser
CAC ACC CAC UUU GUA GAU AUU ACA GUG GGG CUA CAA CAG CUG AUA CUC AUC AGU
    80          30                  100     50                  120 40
Val Asp Glu Val Asn Gln Ile Val Glu Thr Asn Val Arg Leu Arg Gln Gln Trp
GUG GAU GAA GUA AAU CAA AUU GUG GAA ACA AAU GUG CGC CUA AGG CAG CAA UGG
                140                         160                     180 60
Ile Asp Val Arg Leu Arg Trp Asn Pro Ala Asp Tyr Gly Gly Ile Lys Lys Ile
AUU GAU GUG AGG CUU CGC UGG AAU CCA GCC GAU UAU GGU GGA AUU AAA AAG AUC
                    200         70                  220
Arg Leu Pro Ser Asp Asp Val Trp Leu Pro Asp Leu Val Leu Tyr Asn Asn Ala
AGA CUG CCU UCU GAU GAU GUU UGG CUG CCA GAU UUA GUU CUG UAC AAC AAU GCU
        240             80              260                 280
```

FIG. 6-1

```
                100
Asp Gly Asp Phe Ala Ile Val His Met Thr Lys Leu Leu Asp Tyr Thr Gly
GAU GGU GAU UUU GCC AUU GUU CAC AUG ACC AAA CUG UUG GAU UAU ACG GGA
                300                 120                         340

130
Lys Ile Met Trp Thr Pro Pro Ala Ile Phe Lys Ser Tyr Gyx Glu Ile Ile Val
AAA AUA AUG UGG ACA CCU CCA GCA AUC UUC AAA AGC UAU UGU GAA AUU AUU GUA
                    360                         380

150
Thr His Phe Pro Phe Asp Gln Gln Asn Cys Thr Met Lys Leu Gly Ile Ile Trp Thr
ACA CAU UUC CCA UUU GAU CAA CAA AAU UGC ACU AUG AAG UUG GGA AUC UGG ACG
        400                 420                             440

160
Tyr Asp Gly Thr Lys Val Ser Ile Ser Pro Glu Ser Asp Arg Pro Asp Leu Ser
UAC GAU GGG ACA AAA GUU UCC AUA UCC CCG GAA AGU GAC CGU CCG GAU CUG AGU
            460                     480                             500

170              180
Thr Phe Met Glu Ser Gly Glu Ser Gly Lys Val Met Lys Asp Tyr Arg Gly Trp Lys His
ACA UUU AUG GAA AGU GGA GAG UCC GUA AUG AAA GAU UAU CGU GGA UGG AAG CAC
                520                         540

190                                          200
Trp Val Tyr Tyr Thr Cys Cys Pro Asp Thr Pro Tyr Leu Asp Ile Thr Tyr His
UGG GUG UAU UAU ACC UGC UGU CCU GAC ACU CCU UAC CUG GAU AUC ACC UAC CAU
560                     580                         600
```

FIG. 6-2

```
                                                        220
Phe Ile Met Gln Arg Ile Pro Leu Tyr Phe Val Val Asn Val Ile Pro Cys
UUU AUC AUG CAG CGU AUU CCU CUU UAU UUU GUU GUG AAU GUC AUC CCU UGU
            620                         640                     660

250
Leu Leu Phe Ser Phe Leu Thr Gly Leu Val Phe Tyr Leu Pro Thr Asp Ser Gly
CUG CUU UUU UCA UUA ACU GGA UUA GUA UUU UAC UUA CCA ACU GAU UCA GGU
            680                         700                     720

Glu Lys Met Thr Leu Ser Ile Ser Val Leu Ser Leu Thr Val Phe Leu Leu
GAG AAG AUG ACU UUG AGU AUU UCC GUU UUG UCU CUG ACU GUG UUC CUU CUG
            740                         760

260                 270
Val Ile Val Glu Leu Pro Ser Ser Ala Val Pro Leu Ile Gly Lys
GUU AUU GUU GAG CUG CCC UCA AGC GCU GUG CCU UUG AUU GGC AAA
    780                     800                     820

280                             290
Tyr Met Leu Phe Thr Met Ile Phe Val Ile Ser Ser Ile Ile Thr Val Val
UAC AUG CUU UUU ACA AUG AUU GUC AUC AGU UCA AUC AUU ACU GUU GUU
            840                         860                 880

300                 310
Val Ile Asn Thr His Arg Ser Pro Ser Thr His Thr Met Pro Gln Trp Val
GUA AUU AAU ACU CAC CGC UCU CCA AGU ACA CAU ACA AUG CCA CAA UGG GUA
    900                     920
```

FIG. 6-3

```
Arg Lys Ile Phe Ile Asp Thr Ile Pro Asn Val Met Phe Phe Ser Thr Met Lys
CGA AAG AUC UUU AUU GAU ACU AUA CCC AAU GUU AUG UUU UUC UCA ACA AUG AAA
    940                     960                     980                     330

Arg Ala Ser Lys Glu Lys Gln Glu Asn Lys Ile Phe Ala Asp Ile Phe Gln Thr Pro Leu
CGA GCU UCU AAG GAA AAG CAA GAA AAU AAG AUA UUU GCU GAU AUC AUU CAA ACA CCU CUC
            1,000                   340        1,020                   1,040

Ser Asp Ile Ser Gly Lys Gln Val Thr Gly Glu Val Ile Glu Gly Val Lys Tyr Ile Ala Glu
UCU GAC AUU UCU GGA AAG CAA GUG ACA GGA GAA GUA AUU GAG GGA GUC AAA UAU AUU GCA GAG
            1,060                   360        1,080                   380        1,140

Ile Lys Asn Pro Asp Val Lys Ser Ala Ile Glu Ser Asn Ala Ala Glu Trp Lys Tyr Val
AUU AAA AAU CCA GAU GUC AAA AGU GCU AUU GAG AGC AAU GCA GCA GAG UGG AAA UAU GUU
1,100                       1,120                   1,180                       1,200

His Met Lys Ser Asp Glu Ser Asp Glu Ser Ser Asn Ala Ala Glu Val Phe Met Leu Ile Cys Ile Ile
CAC AUG AAG UCU GAU GAG UCA GAA UCA AGC AAU GCA GCA GAG GUC UUC AUG CUG AUU UGU AUA AUU
        1,160                   390                     1,180                   1,240                       420

Ala Met Val Ile Asp His Ile Asp Leu Leu Cys Val Phe Met Leu Ile Glu Leu Cys Ile Ile
GCA AUG GUG AUU GAU CAC CUG CUG UGU GUC UUC AUG CUG AUU GAA CUC AUU UGU AUA AUU
                1,220                   410                     1,240                   1,260

Gly Thr Val Ser Val Phe Ala Gly Arg Leu Ile Glu Leu Ser Gln Gly Gly
GGU ACA GUU AGC GUG UUU GCU CGU CUC AUU GAA CUC AGU CAA GGC UAA
                1,280                   430                     1,300

```
                                            His-Gly
N-Ac-Ala-Ser-Ala-Gln-Lys-Arg-Pro-Ser-Gln-Arg-Ser-Lys-Tyr-Leu-Ala-
     (-)                                10

Thr
Ser-Ala-Ser-Thr-Met-Asp-His-Ala-Arg-His-Gly-Phe-Leu-Pro-Arg-His-
                    20                                      30

Ile            Gly
Arg-Asp-Thr-Gly-Ile-Leu-Asp-Ser-Leu-Gly-Arg-Phe-Phe-Gly-Ser-Asp-
                              40

Ser
Arg-Gly-Ala-Pro-Lys-Arg-Gly-Ser-Gly-Lys-Asp-Gly-His-His-Ala-Ala-Arg-
                  50                                    60

Ala              Ser (-)              Thr
Thr-Thr-His-Tyr-Gly-Ser-Leu-Pro-Gln-Lys-Ala-Gln-Gly-His-Arg-Pro-Gln-
                          70                                80

Asp-Glu-Asn-Pro-Val-Val-His-Phe-Phe-Lys-Asn-Ile-Val-Thr-Pro-Arg-Thr-
                                        90

Me
Pro-Pro-Pro-Ser-Gln-Gly-Lys-Gly-Arg-Gly-Leu-Ser-Leu-Ser-Arg-Phe-Ser-
                100                                    110

Arg
Trp-Gly-Ala-Glu-Gly-Gln-Lys-Pro-Gly-Phe-Gly-Tyr-Gly-Arg-Ala-Ser-
                    120                                130

Phe              Val
Asp-Tyr-Lys-Ser-Ala-His-Lys-Leu-Lys-Gly-Leu-His-Asp-Ala-Gln-Gly-Thr-
                                  140

Leu-Ser-Lys-Ile-Phe-Lys-Leu-Gly-Gly-Arg-Asp-Ser-Arg-Ser-Gly-Ser-Pro-
           150                                      160

Met-Ala-Arg-Arg-COOH
           170
```

FIG. 8-1

IAB ALPHA CHAIN

```
  1 AAT TCA TGC CGC GCA GCA GAG CTC TGA TTC TGG GGG TCC TCG CCC
    TTA AGT ACG GCG CGT CGT CTC GAG ACT AAG ACC CCC AGG AGC GGG

46 TGA CCA CCA TGC TCA GCC TCT GTG GAG GTG AAG ACG ACA TTG AGG
    ACT GGT GGT ACG AGT CGG AGA CAC CTC CAC TTC TGC TGT AAC TCC

91 CCG ACC ACG TAG GCA CCT ATG GTA TAA GTG TAT ATC AGT CTC CTG
    GGC TGG TGC ATC CGT GGA TAC CAT ATT CAC ATA TAG TCA GAG GAC

136 GAG ACA TTG GCC AGT ACA CAT TTG AAT TTG ATG GTG ATG AGT TGT
    CTC TGT AAC CGG TCA TGT GTA AAC TTA AAC TAC CAC TAC TCA ACA

181 TCT ATG TGG ACT TGG ATA AGA AGG AGA CTG TCT GGA TGC TT

FIG. 8-2

```
406 GCT TTG TGG ACA ACA TCT TCC CTC CTG TGA TCA ACA TCA CAT GGC
    CGA AAC ACC TGT TGT AGA AGG GAG GAC ACT AGT TGT AGT GTA CCG

451 TCA GAA ARA GCA AGT CAG TCG CAG ACG GTG TTT ATG AGA CCA GCT
    AGT CTT TYT CGT GTC AGC GTC TGC CAC AAA TAC TCT GGT CGA

496 TCT TCG TCA ACC GTG ACT ATT CCT TCC ACA AGC TGT CTT ATC TCA
    AGA AGC AGT TGG CAC TGA TAA GGA AGG TGT TCG ACA GAA TAG AGT

541 CCT TCA TCC CTT CTG ACG ATG ACA TTT AAA TAC ACT GCA AGG TGG AAC
    GGA AGT AGG GAA GAC TGC TAC TGT AAA TAC TGA CGT TCC ACC TTG

586 ACT GGG GCC TGG AGG AGC CGG TTC TGA AAC ACT GGG AAC CTG AGA
    TGA CCC CGG ACC TCC GCC AAG ACT TTG TGA CCC TTG GAC TCT

631 TTC CAG CCC CCA TGT CAG AGC TGA CAG AGA CTG TGG TGT GTG CCC
    AAG GTC GGG GGT ACA GTC TCG ACT GTC TCT GAC ACC ACA CAC GGG

676 TGG GGT TGT CTG TGG GCC TTG TGG GCA TCG TGG TGG GCA CCA TCT
    ACC CCA ACA GAC CGG AAC ACC CGT AGC ACC ACC CGT GGT AGA

721 TCA TCA TTC AAG GCC TGC GAT CAG GTG GCA CCT CCA GAC ACC CAG
    AGT AGT AAG TTC CGG ACG CTA GTC CAC CGT GGA CTG TGG GTC

766 GGC CTT TAT GA
    CCG GAA ATA CT
```

FIG. 9-1

IAB BETA CHAIN

```
  1  CAT TTC GTG TAC CAG TTC ATG GGC GAG TGC TAC TTC ACC AAC GGG
     GTA AAG CAC ATG GTC AAG TAC CCG CTC ACG ATG AAG TGG TTG CCC

46  ACG CAG CGC ATA CGA TAT GTG ACC AGA TAC ATC TAC AAC CGG GAG
     TGC GTC GCG TAT GCT ATA CAC TGG TCT ATG TAG TTG GCC CTC

91  GAG TAC GTG CGC TAC GAC AGC GAC GTG GGC GAG CAC CGC GCG GTG
     CTC ATG CAC GCG ATG CTG TCG CTG CAC CCG CTC GTG GCG CGC CAC

136  ACC GAG CTG GGG CGG CCA GAC GCC GAG TAC TGG AAC AGC CAG CCG
     TGG CTC GAC CCC GCC GGT CTG CGG CTC ATG ACC TTG TCG GTC GGC

181  GAG ATC CTG GAG CGA ACG CGG GCC GAG CTC GAC ACC GTG TGC AGA
     CTC TAG GAC CTC GCT TGC GCC CGG CTC GAG CTG TGC CAC ACG TCT

226  CAC AAC TAC GAG GGG CCC GAG ACC CAC ACC TCC CTG CGG CGG CTT
     GTG TTG ATG CTC CCC GGG CTC TGG GTG TGG AGG GAC GCC GCC GAA

271  GAA CAG CCC AAT GTC GTC ATC TCC CTG TCC AGG ACA GAG GCC CTC
     CTT GTC GGG TTA CAG CAG TAG AGG GAC AGG TCC TGT CTC CGG GAG

316  AAC CAC CAC AAC ACT CTG GTC TGC TCA GTG ACA GAT TTC TAC CCA
     TTG GTG GTG TTG TGA GAC CAG ACG AGT CAC TGT CTA AAG ATG GGT
```

FIG. 9-2

```
361 GCC AAG ATC AAA GTG CGC TGG TTC CGG AAT GGC CAG GAG GAG ACG
    CGG TTC TAG TTT CAC GCG ACC AAG GCC TTA CCG GTC CTC TGC

406 GTG GGG GTC TCA TCC ACA CAG CTT ATT AGG AAT GGG GAC TGG ACC
    CAC CCC CAG AGT AGG TGT GTC GAA TAA TCC CCC CTG ACC TGG

451 TTC CAG GTC CTG GTC ATG CTG GAG ATG ACC CCT CGG CGG GGA GAG
    AAG GTC CAG GAC CAG CTC TAC GAC CTC TGG GGA GCC GCC CCT CTC

496 GTC TAC ACC TGT CAC GTG GAG CAT CCC AGC CTG AAG AGC CCC ATC
    CAG ATG TGG ACA GTG CAC CTC GTA GGG TCG GAC TTC TCG GGG TAG

541 ACT GTG GAG TGG AGG GCA CAG TCT GAG TCT GCC TGG AGC AAG ATG
    TGA CAC CTC ACC TCC CGT GTC AGA CTC ACG GGG ACC TCG TTC TAC

586 TTG AGC GGC ATC GGG GGC TGC GTG CTT GGG GTG ATC TTC CTC GGG
    AAC TCG CCG TAG CCC ACG CCG GAA CCC CAC TAG AAG GAG CCC

631 CTT GGC CTT TTC ATC CGT CAC AGG AGT CAG AAA GGA CCT CGA GGC
    GAA CCG GAA AAG TAG GCA GTG TCC TCA GTC TTT CCT GGA GCT CCG

676 CCT CCT CCA GCA GGG CTC CTG CAG TGA
    GGA GGA GGT CGT CCC GAG GAC GTC ACT
```

| HPTYP # | FREQ %[2] | DQ | DQB1 | DQA1[3] | DRB1 | DRB3 | DRB4 | D | DISEASE ASSOCIATION[4] |
|---|---|---|---|---|---|---|---|---|---|
| 1. | 20 | w5(w1) | 1.1 | 1a | — | ne | ne | w1 | IDDM*, RA† |
| 2. |  | w5(w1) | 1.1 | 1a | — | ne | ne | w20 | IDDM |
| 3. | 26 | w6(w1) | 1.2 | 1b | w15(2) | ne | ne | w2 | CPMS, MG(T+) |
| 4. | 1.5 | w6(w1) | 1.12 | 1c | w15(2) | ne | ne | w12 |  |
| 5. | 1.5 | w5(w1) | 1.1 | ? | w16(2) | ne | ne | w21(AZH) | IDDM, MG(T−) |
| 6. | ? | w7(w3) | 3.1 | ? | w16(2) | ne | ne | w22 |  |
| 7. | 22 | w2 | ? | ? | w17(3) | 24(52) | ne | w3 ⎫ |  |
| 8. |  | w2 | ? | ? | w17(3) | 25(52) | ne | w3 ⎬ | IDDM, MG(T−) |
| 9. | ? | w4(Wa) | Wa | ? | w18(3) | ?(52) | ne | ? ⎭ |  |
| 10. | 9 | w8(w3) | 3.2 | 3 | 4 | ne | 53 | w4(4.2) | IDDM*, RA†, CPMS |
| 11. | 5 | w7(w3) | 3.1 | 3 | 4 | ne | 53 | w4(4.1) |  |
| 12. | 3 | w8(w3) | 3.2 | 3 | 4 | ne | 53 | w10 | IDDM*, CPMS |
| 13. | ? | w7(w3) | 3.1 | 3 | 4 | ne | 53 | w13 |  |
| 14. | 14 | w8(w3) | 3.2 | ? | 4 | ne | 53 | w14 | IDDM*, RA†, CPMS |
| 15. | 0.5 | w4(Wa) | Wa | ? | 4 | ne | 53 | w15 | RA |

FIG. 10-1

| | | | | | | | | |
|---|---|---|---|---|---|---|---|---|
| 16. | 15 | {w7(w3) | 3.1 | 2 | w11(5) | 25(52) | ne | w5} |
| 17. | — | {w7(w3) | 3.1 | 2 | w12(5) | 25(52) | ne | B6} MG |
| 18. | 10 | {w5(w1) | 1.18 | 1c | w(13)(w6) | 24(52) | ne | w18 |
| 19. | 3 | {w5(w1) | 1.18 | 1c | w(13)(w6) | 25(52) | ne | w18 IDDM |
| 20. | 3 | w5(w1) | 1.19 | 1b | w(13)(w6) | 26(52) | ne | w19 |
| 21. | 3 | w6(w1) | 1.9 | 1a | w(14)(w6) | 25(52) | ne | w9 |
| 22. | ? | w6(w1) | 1.16 | 2 | w(14)(w6) | 24(52) | ne | w16 RA |
| 23. | 1 | w9(w3) | 3.3 | 3 | 7 | ne | 53 | w11 |
| 24. | 27 | w2 | 2 | 3 | 7 | ne | 53 | w17 |
| 25. | 6 | w4(Wa) | Wa | 1b | ne | w8/52 | ne | w8 |
| 26. | 2 | ?(w3) | ? | 1b | ne | w8/52 | ne | w8 |
| 27. | 1 | w9(w3) | 3.3 | 3 | 9 | ne | 53 | w23 |
| 28. | ? | w5(w1) | 1.1 | 1a | w10 | ? | ? | ? |

FIG. 10-2

10-2.16 Mab WERE PURIFIED ON PROTEIN-A COLUMN FROM 5 ml ASCITES, 30mg PURE Ab WERE RECOVERED. A STANDARD PROCEDURE (MAPS II) FROM Bio-Rad LABORATORIES WAS FOLLOWED

COUPLED TO CNBr ACTIVATED SEPHAROSE 4B
(3-4 mg Ab/ml OF WET GEL)
STANDARD PROCEDURE FROM PHARMACIA WAS FOLLOWED
EXTENT OF COUPLING → 98%

PURIFIED IgG WAS ANALYZED ON 10% ID POLYACRYLAMIDE GEL FOLLOWED BY COOMASSIE BRILLIANT BLUE R-250

FIG. 13a.

ONE DIMENSIONAL POLYACRYLAMIDE GEL ANALYSIS OF PURIFIED 10-2.16 MONOCLONAL ANTIBODY

ONE DIMENSIONAL POLYACRLAMIDE GEL ANALYSIS OF IAk

WASHED 10-2.16 ANTIBODY COLUMN WITH LOW AND HIGH pH
BUFFERS AND EQUILIBRATED WITH 0.5% NP-40 BUFFER, pH
8.3 (10mM TRIS HCl pH 8.3, 0.5% NP40, 0.1 M NaCl,
5 mM EDTA, 0.02% NaN$_3$ AND 1 mM PMSF)

↓

APPLIED 50ml MEMBRANE FRACTION (20-25mg TOTAL PROTEIN)
TO A 4ml BED VOLUME COLUMN CONTAINING 15-20mg
COUPLED ANTIBODIES (CIRCULATED OVERNIGHT AT 4°C)

↓

WASHED COLUMN WITH 10 BED VOLUMES OF
0.5% DOC BUFFER, pH 8.3
(1mM TRIS HCl, pH 8.3, 0.5% DEOXYCHOLATE, 0.1 M NaCl,
5mM EDTA. 0.02% NanN$_3$ AND 5mM PMSF)

↓

WASHED WITH 5 BED VOLUMES OF
1% OG BUFFER IN PHOSPHATE BUFFER, pH 8.3
(20mM PHOSPHATE pH 8.3, 0.1 M NaCl, 1% OCTYLGLUCOSIDE
.02% NaN$_3$ AND 5mM PMSF)

↓

ELUTED WITH 1% OG IN PHOSPHATE BUFFER, pH 11.0
(20mM PHOSPHATE pH 11, 0.1 M NaCl, 1% OCTYLGLUCOSIDE
.02% NaN$_3$ AND 5 mM PMSF)
NEUTRALIZED EACH 1ml FRACTION WITH 12 μl OF 1 M ACETIC ACID

↓

POOLED PEAK WAS CONCENTRATED (5-10 FOLD)
BY VACUUM DIALYSIS

↓

TOTAL I-A$^k$ = 200-300 μg (FROM 5×10$^9$ SPLEEN CELLS)
ANALYZED ON 10% PAGE FOLLOWED BY SILVERSTAIN

FIG. 14.

MHC CONJUGATES USEFUL IN AMELIORATING AUTOIMMUNITY

CROSS-REFERENCE TO RELATED APPLICATIONS

This application is a continuation of Ser. No. 08/462,351, filed Jun. 5, 1995, now U.S. Pat. No. 6,106,840, which is a divisional of Ser. No. 07/869,293, filed Apr. 14, 1992, which is a c-i-p of Ser. No. 07/690,840, filed Apr. 23, 1998, now U.S. Pat. No. 5,260,422, which is a c-i-p of Ser. No. 07/576,084, filed Aug. 30, 1990, now U.S. Pat. No. 5,130,297, which is a continuation of Ser. No. 07/210,594, filed Jun. 23, 1988, now abandoned and claims the benefit of the disclosure of which is incorporated by reference.

TECHNICAL FIELD

The invention relates to the methods and compositions for the modulation of T cell function in the treatment of for example, autoimmune diseases, allergic responses, transplant rejection, and other immunological disorders. In particular, it concerns complexes which target helper T cells by using a complex of the major histocompatibility complex (MHC) glycoproteins with peptides representing fragments of antigens associated with such diseases. These complexes can be further conjugated to radioisotopes or other labels for diagnostic purposes, or to toxins or other substances which render the complexes therapeutically useful.

BACKGROUND OF THE INVENTION

A number of pathological responses involving unwanted T cell activation are known. For instance, a number of allergic diseases, have been associated with particular MHC alleles or suspected of having an autoimmune component.

Other deleterious T cell-mediated responses include the destruction of foreign cells that are purposely introduced into the body as grafts or transplants from allogeneic hosts. This process, known as "allograft rejection," involves the interaction of host T cells with foreign MHC molecules. Quite often, a broad range of MHC alleles are involved in the response of the host to an allograft.

Autoimmune disease is a particulalry important class of deleterious immune response. In autoimmune diseases, self-tolerance is lost and the immune system attacks "self" tissue as if it were a foreign target. More than 30 autoimmune diseases are presently known; these include many which have received much public attention, including myasthenia gravis (MG) and multiple sclerosis (MS).

A crude approach to treating autoimmune disease and other immunopathologies is general immunosuppression. This has the obvious disadvantage of crippling the ability of the subject to respond to real foreign materials to which it needs to mount an immune response. An only slightly more sophisticated approach relies on the removal of antibodies or immune complexes involving the target tissue. This also has adverse side effects, and is difficult to accomplish. The invention approach, described in detail below, relies on a "clonotypic" reagent—i.e., a reagent which attacks only the cells of the immune system which are responsive to the autoantigen.

In the general paradigm now considered to describe the immune response, specific antigens presented result in a clonal expansion, as first proposed by Burnet in 1959. According to this scenario, a particular subject will have hundreds of thousands of T and B cells each bearing receptors that bind to different antigenic determinants. Upon exposure to an antigen, the antigen selectively binds to cells bearing the appropriate receptors for the antigenic determinants it contains, ignoring the others. The binding results in a cloned population of thousands of daughter cells, each of which is marked by the same receptor. A clonotypic reagent affects only a subset of the T and B cells which are appropriate for the antigen of interest. In the case of the invention compositions, the antigenic determinant is usually that associated with an autoimmune disease.

The clonotypic reagent compositions of the invention are specifically designed to target T-helper cells which represent the clones specific for the antigenic determinant(s) of the tissue which is affected by the autoimmune disease. T-helper cells recognize a determinant only in association with an MHC protein; the complexes of the invention therefore include an effective portion of the MHC protein.

There have, recently, been some related approaches which attempt to interdict the immune response to specific antigens. For example, the autoantigen thyroglobulin has been conjugated to ricin A and the conjugate was shown to suppress specifically the in vitro antibody response of lymphocytes which normally respond to this antigen. It was suggested that such immunotoxins would specifically delete autoantibody-secreting lymphocyte clones (Rennie, D. P., et al., *Lancet* (Dec. 10, 1983) 1338–1339). Diener, E., et. al., *Science* (1986) 231:148–150 suggested the construction of compounds which cause antigen-specific suppression of lymphocyte function by conjugating daunomycin to the hapten (in this case, of ovalbumin) using an acid-sensitive spacer. The conjugate caused hapten-specific inhibition of antibody secretion by B lymphocytes in vitro and in vivo. A conjugate of daunomycin (with an acid-sensitive spacer) to a monoclonal antibody-specific to T cells also eliminated the response by T-lymphocytes to concanavalin A. Steerz, R. K. M., et al., *J. Immunol.* (1985) 134:841–846 utilized radiation as the toxic element in a toxin conjugate. Rats were administered a radioactively labeled, purified receptor from electric fish, prior to injection with cold receptor. Injection with this receptor is a standard procedure to induce experimental autoimmune myasthenia gravis (EAMG). Control rats that received preinjection only either of cold receptor or radiolabeled albumin, prior to administration of receptor to induce the disease develop the symptoms of EAMG; those pretreated with radioactively-labeled receptor showed reduced symptoms. It was surmised that the labeled, and therefore destructive, receptor selectively eliminated immunocompetent cells. Similar work utilizing a ricin/receptor conjugate for pretreatment was reported by Killen, J. A., et al., *J. Immunol.* (1984) 133:2549–2553.

A less specific approach which results in the destruction of T cells in general is treatment with an IL-2/toxin conjugate as reported by Hixson, J. R., Medical *Tribune* (Jan. 28, 1988) 4–5. In a converse, but related, approach Liu, M. A., et al., *Science* (1988) 239:395–397, report a method to "link up" cytotoxic T cells with a desired target, regardless of the cytotoxic T cell specificity. In this approach, antibody specific to the universal cytotoxic T-lymphocytes to destroy human melanoma cells when melanocyte-stimulating hormone was the hormone used.

The current model of immunity postulates that antigens mobilize an immune response, at least in part, by being ingested by an antigen-presenting cell (APC) which contains on its surface a Class II glycoprotein encoded by a gene in the major histocompatibility complex (MHC). The antigen is then presented to a specific T helper cell in the context of the surface bound MHC glycoprotein, and by interaction of the antigen specific T cell receptor with the antigen —MHC complex, the T helper cell is stimulated to mediate the antigen-specific immune response, including induction of cytotoxic T cell function, induction of B cell function, and secretion of a number of factors aiding and abetting this response.

The involvement of the MHC Class II proteins in autoimmune disease has been shown in animal models. Administration of antibodies to either MHC Class II proteins themselves or antibodies to agents that induce expression of the MHC Class II genes interferes with development of the autoimmune condition in these model systems. The role of helper T cells has also been demonstrated in these models by counteracting the autoimmune system using anti-CD4 monoclonal antibodies; CD4 is the characteristic helper T cell receptor (Shizuru, J. A. et al., *Science* (1988) 240:659–662).

Recent experiments have shown that, under certain circumstances, anergy or nonresponsiveness can be induced in autoreactive lymphocytes (see, Schwartz, *Cell* (1989) 1073–1081, which is incorporated herein by reference). In vitro experiments suggest that antigen presentation by MHC Class II molecules in the absence of an unknown co-stimulatory signal induces a state of proliferative non-responsiveness in syngeneic T cells (Quill et al., *J. Immunol.* (1987) 138:3704–3712, which is incorporated herein by reference). These reports, however, provide no clear evidence that induction of anergy in vivo is possible or that autoimmune disease can be effectively treated in this manner.

SUMMARY OF THE INVENTION

The present invention is directed to methods and compositions that can be used to identify and inhibit those aspects of the immune system which are responsible for undesirable autoimmunity. The invention compositions and methods are designed to target helper T cells which recognize a particular antigen in association with a glycoprotein encoded by the MHC. The invention complexes effectively substitute for the antigen-presenting cell and cause non-responsiveness in autoreactive T-lymphocytes and other cells of the immune system.

The invention provides forms of an autoantigen which interact with the immune system, in a manner analogous to those initiated by the autoantigen itself to cause the autoimmune reaction. Compositions of the present invention are purified two component complexes of (1) an effective portion of the MHC-encoded antigen-presenting glycoprotein; and (2) an effective portion of the antigen. These two components may be bound covalently or by noncovalent association. Evidence from both in vitro and in vivo experiments establishes that such complexes induce clonal anergy in syngeneic T cells.

In other aspects, the invention is directed to pharmaceutical compositions wherein the complexes of the invention are active ingredients. The compositions can be used to down-regulate parts of the immune system reactive with a particular self-antigen associated with an autoimmune disease.

BRIEF DESCRIPTION OF THE DRAWINGS

FIG. 1 is a diagram of a typical complex of the invention.

FIG. 3 shows a diagrammatic representation of the active portion of a modified Class II MHC-encoded glycoprotein.

FIG. 4 shows preferred second generation MHC protein designs.

FIG. 6 shows the amino acid sequence (SEQ ID NO: 2) and encoding mRNA (SEQ ID NO: 1) for the alpha subunit of acetylcholine receptor protein.

FIG. 7 shows the amino acid sequence (SEQ ID NO: 3) of myelin basic protein.

FIG. 8 shows the nucleotide sequence (SEQ ID NO: 4) encoding the I-$A^b$-alpha chain.

FIG. 9 shows the nucleotide sequence (SEQ ID NO: 5) encoding the I-$A^b$-beta chain.

FIG. 10 presents a list of the DQ/DR haplotypes in humans and their associations with autoimmune diseases.

FIG. 13A is a scheme for the affinity purification of 10–2.16 monoclonal antibody and its coupling to CNBr activated Sepharose 4B.

FIG. 14 shows a scheme for the purification of I-$A^k$.

DESCRIPTION OF PREFERRED EMBODIMENTS

Figure 2A:
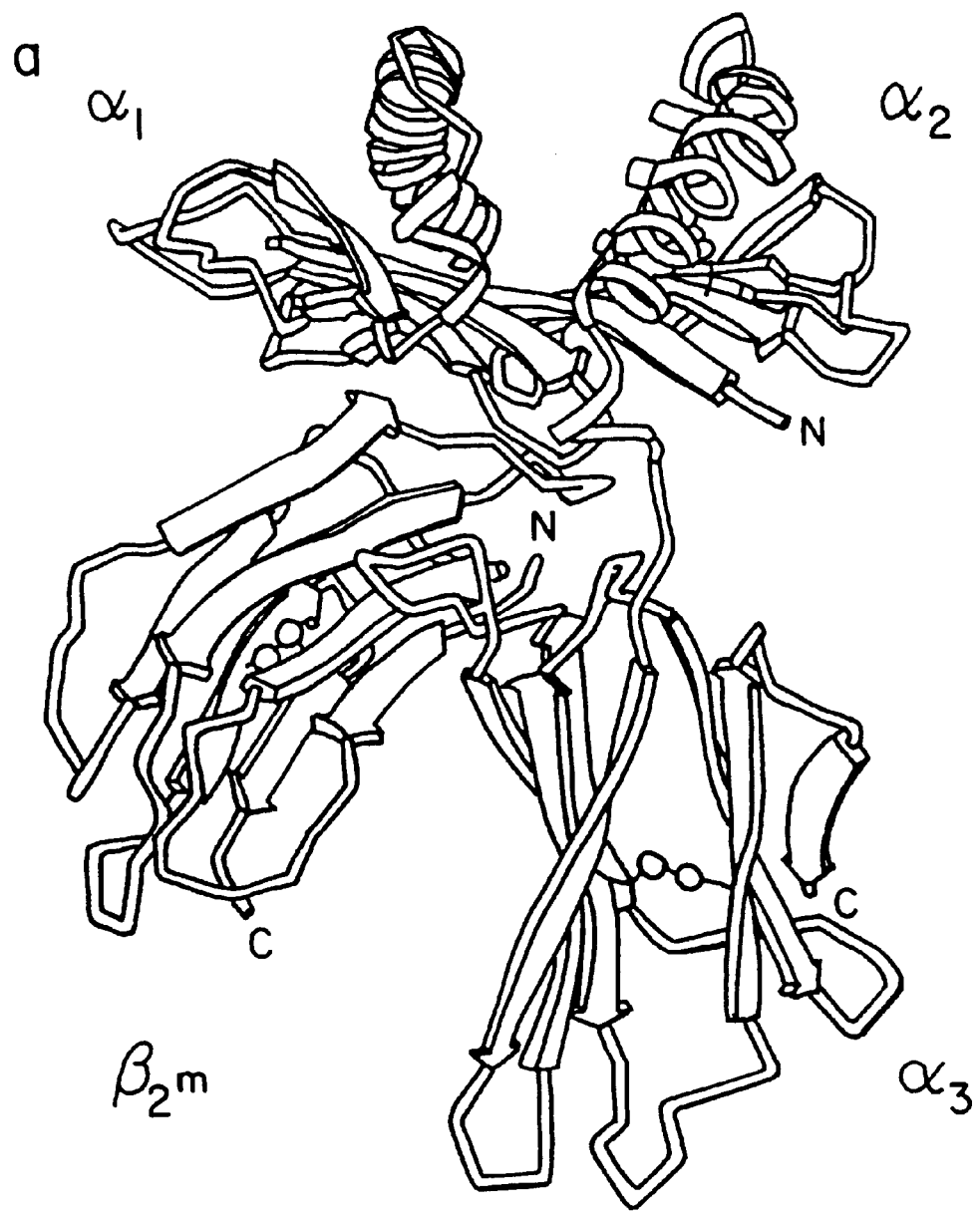
FIG. 2 shows the 3-dimensional structure of the human HLA-A2 antigen (Class I).

The present invention provides complexes which can be used to modulate T cell function. For instance, the complexes can be used to inhibit a deleterious T cel-mediated immune response, such as allergic responses, allograft rejection, and autoimmune diseases. In addition, the complexes of the invention can also be used as vaccines and thus, promote T cell responses.

The invention complexes contain at least two components: a peptide which represents an autoantigen or other antigenic sequence with the relevant effect on the immune system and an effective portion of the MHC-encoded glycoprotein involved in antigen presentation. An effective portion of an MHC glycoprotein is one which comprises the antigen binding sites and sequences necessary for recognition of the MHC-peptide complex by the appropriate T cell receptor. The MHC component can be either a Class I or a CLass II molecule. The association between the peptide antigen and the antigen binding sites of the MHC protein can be by covalent or by noncovalent bonding.

In other embodiments the complexes may also contain an effector component which is generally a toxin or a label. The effector portion may be conjugated to either the MHC-encoded glycoprotein or to the autoantigenic peptide. Complexes containing an effector component are disclosed and claimed in copending application U.S. Ser. No. 07/367,751 filed Jun. 21, 1989, supra.

Each of the components of the system is described separately below; followed by description of the methods by which these complexes can be prepared, evaluated and employed.

The MHC-Derived Component

The glycoproteins encoded by the MHC have been extensively studied in both the human and murine systems. In general, they have been classified as Class I glycoproteins, found on the surfaces of all cells and primarily recognized by cytotoxic T cells; and Class II which are found on the surfaces of several cells, including accessory cells such as macrophages, and are involved in presentation of antigens to helper T cells. Some of the histocompatibility proteins have been isolated and characterized. For a general review of MHC glycoprotein structure and function, see *Fundamental Immunology*, 2d Ed., W. E. Paul, ed., Ravens Press N.Y. 1989, which is incorporated herein by reference. The term "isolated MHC component" as used herein refers to an MHC glycoprotein or an effective portion of an MHC glycoprotein (i.e., one comprising an antigen binding site or sites and sequences necessary for recognition by the appropriate T cell receptor) which is in other than its native state, for example, not associated with the cell membrane of a cell that normally expresses MHC. As described in detail below, the MHC component may be recombinantly produced, solubilized from the appropriate cell source or associated with a liposome.

Methods for purifying the murine I-A (Class II) histocompatibility proteins have been disclosed by Turkewitz, A. P., et al., *Molecular Immunology* (1983) 20:1139–1147, which is incorporated herein by reference. These methods, which are also suitable for Class I molecules, involve preparation of a soluble membrane extract from cells containing the desired MHC molecule using nonionic detergents, such as NP-40, Tween 80 and the like. The MHC molecules are then purified by affinity chromatography, using a column containing antibodies raised against the desired MHC molecule. Use of 0.02% Tween-80 in the elution buffer is helpful to eliminate aggregation of the purified molecules.

The isolated antigens encoded by the I-A and I-E subregions have been shown to consist of two noncovalently bonded peptide chains: an alpha chain of 32–38 kd and a beta chain of 26–29 kd. A third, invariant, 31 kd peptide is noncovalently associated with these two peptides, but it is not polymorphic and does not appear to be a component of the antigens on the cell surface (Sekaly, R. P., *J. Exp. Med.* (1986) 164:1490–1504, which is incorporated herein by reference). The alpha and beta chains of seven allelic variants of the I-A region have been cloned and sequenced (Estees, "T cell Clones", 3–19).

The human Class I proteins have also been studied. The MHC of humans (HLA) on chromosome 6 has three loci, HLA-, HLA-B, and HLA-C, the first two of which have a large number of alleles encoding alloantigens. These are found to consist of a 44 kd subunit and a 12 kd $beta_2$-microglobulin subunit which is common to all antigenic specificities. Isolation of these detergent-soluble HLA antigens was described by Springer, T. A., et al., *Proc. Natl. Acad. Sci. USA* (1976) 73:2481–2485; Clementson, K. J., et al., in "Membrane Proteins" Azzi, A., ed; Bjorkman, P., Ph.D. Thesis Harvard (1984) all of which are incorporated herein by reference.

Figure 2B:
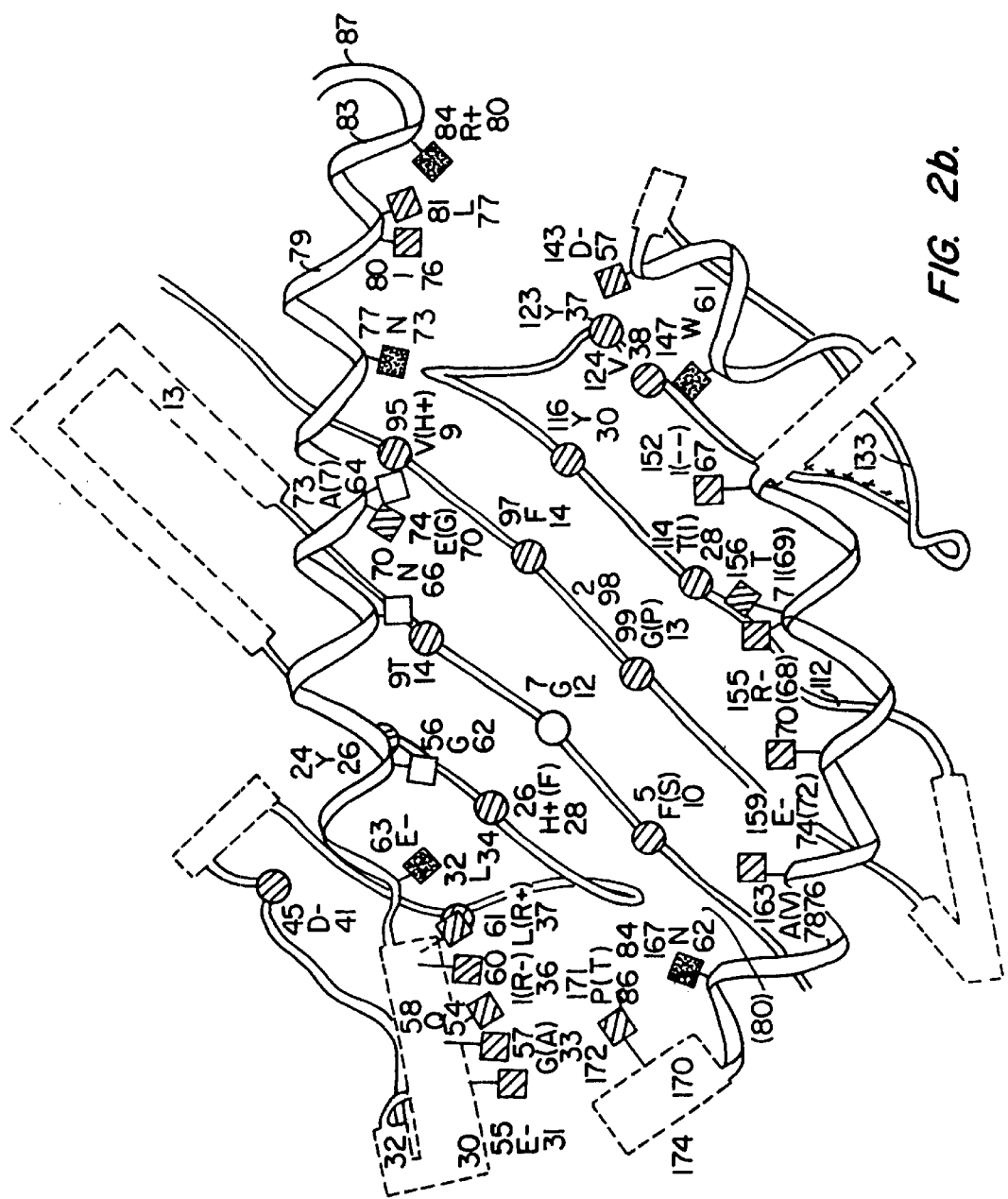
Figure 5:
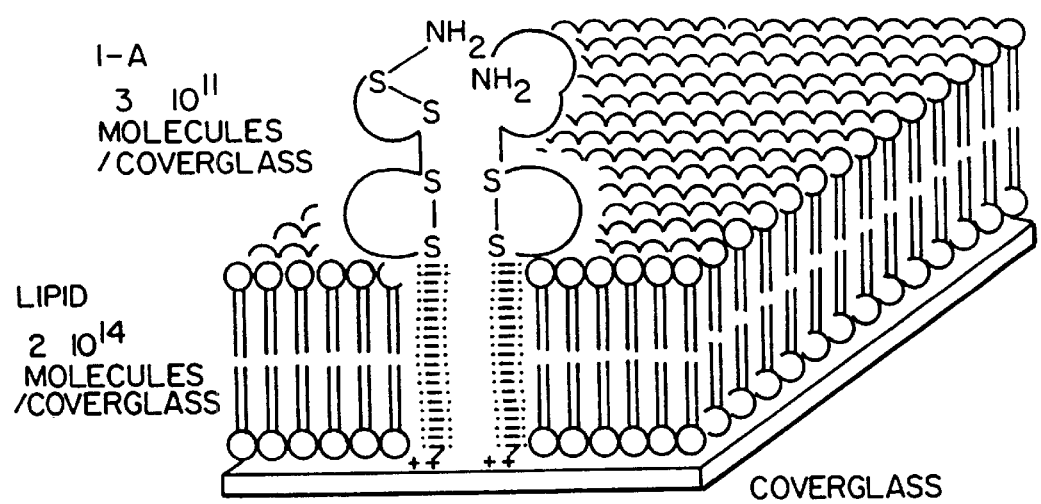
FIG. 5 is a diagram of a planar membrane bilayer including the MHC glycoprotein, mimicking the surface of the antigen presenting cell.

Further work has resulted in a detailed picture of the 3-D structure of HLA-A2, a Class I human antigen. (Bjorkman, P. J., et al., *Nature* (1987) 329:506–512, 512–518 which is incorporated herein by reference). In this picture, the $\beta_2$-microglobulin protein and $alpha_3$ segment of the heavy chain are associated; the $alpha_1$ and $alpha_2$ regions of the heavy chain appear to form antigen-binding sites to which the peptide is bound (*Science* (1987) 238:613–614, which is incorporated herein by reference) Bjorkman, P. J. et al. *Nature* (supra). Soluble HLA-A2 can be purified after papain digestion of plasma membranes from the homozygous human lymphoblastoid cell line J-Y as described by Turner, M. J. et al.,*J. Biol. Chem.* (1977) 252:7555–7567, all of which are incorporated herein by reference. Papain cleaves the 44 kd chain close to the transmembrane region yielding a molecule comprised of $alpha_1$, $alpha_2$, $alpha_3$, and $\beta_2$ microglobulin. A representation of the deduced three dimensional structure of the Class I HLA-A2 antigen is shown in FIG. 2.

While the three dimensional structure of Class II MHC antigens is not known in such detail, it is thought that Class II glycoproteins have a domain structure, including an antigen binding site, similar to that of Class I. It is formed from the N-terminal domain portions of two class II chains which extend from the membrane bilayer. The N-terminal portion of one chain has two domains of homology with the $alpha_1$ and $alpha_2$ regions of the MHC Class I antigen sequence. Cloning of the Class II genes (as described by Estees supra) permits manipulation of the Class II MHC binding domains for example, as described below.

The MHC glycoprotein portions of the complexes of the invention, then, can be obtained by isolation from lymphocytes and screened for the ability to bind the desired peptide antigen. The lymphocytes are from the species of individual which will be treated with the complexes. For example, they may be isolated from human B cells from an individual suffering from the targeted autoimmune disease, which have been immortalized by transformation with a replication deficient Epstein-Barr virus, utilizing techniques known in the art.

MHC glycoproteins have been isolated from a multiplicity of cells using a variety of techniques including solubilization by treatment with papain, by treatment with 3M KCl, and by treatment with detergent. In a preferred method detergent extraction of Class II protein from lymphocytes followed by affinity purification is used. Detergent can then be removed by dialysis or selective binding beads, e.g., Bio Beads.

Alternatively, the amino acid sequence of each of a number of Class II proteins are known, and the genes have been cloned, therefore, the proteins can be made using recombinant methods. In a first generation synthetic MHC protein, the heavy (alpha) and light (beta) chains are synthesized using a carboxy terminal truncation which effects the deletion of the hydrophobic domain, and the carboxy termini can be arbitrarily chosen to facilitate the conjugation of toxins or label. For example, in the MHC protein shown in FIG. 3, lysine residues are introduced. In addition, cysteine residues near the carboxy termini are included to provide a means to form disulfide linkage of the chains; the synthetic gene can also include restriction sites to aid in insertion into expression vectors and in manipulating the gene sequence to encode analogs. The alpha and beta chains are then inserted into expression vectors, expressed separately in an appropriate host, such as E. coli, yeast, or other suitable cells, and the recombinant proteins obtained are recombined in the presence of the peptide antigen.

As the availability of the gene permits ready manipulation of the sequence, a second generation of preferred construction includes hybrid Class I and Class II features, as illustrated in FIG. 4, wherein the $alpha_1$ and $beta_1$ domains of Class II MHC are linked through a flexible portion that permits intramolecular dimerization between these domains resulting in an edge-to-edge beta sheet contact. The $beta_1$ segment is then fused to the $alpha_2$ domain of Class I with $beta_2$ microglobulin coexpressed to stabilize the complex. The transmembrane and intracellular domains of the Class I gene can also be included but there may be no point in doing so unless liposomes are used to transport the complex. A simpler version includes only the $alpha_1$ and $beta_1$ domains with a C-terminal lysine for toxin conjugation (FIG. 4).

Construction of expression vectors and recombinant production from the appropriate DNA sequences are performed by methods known in the art per se. Expression can be in procaryotic or eucaryotic systems. Procaryotes most frequently are represented by various strains of *E. coli*. However, other microbial strains may also be used, such as bacilli, for example *Bacillus subtilis*, various species of Pseudomonas, or other bacterial strains. In such procaryotic systems, plasmid vectors which contain replication sites and control sequences derived from a species compatible with the host are used. For example, *E. coli* is typically transformed using derivatives of pBR322, a plasmid derived from an *E. coli* species by Bolivar et al., *Gene* (1977) 2:95. Commonly used procaryotic control sequences, which are defined herein to include promoters for transcription initiation, optionally with an operator, along with ribosome binding site sequences, including such commonly used promoters as the beta-lactamase (penicillinase) and lactose (lac) promoter systems (Change et al., *Nature* (1977) 198:1056) and the tryptophan (trp) promoter system (Goeddel et al., *Nucleic Acids Res.* (1980) 8:4057) and the lambda-derived $P_L$ promoter and N-gene ribosome binding site (Shimatake et al., *Nature* (1981) 292:128). Any available promoter system compatible with procaryotes can be used. All references cited herein whether supra or infra, are hereby incorporated herein by reference.

The expression systems useful in the eucaryotic hosts comprise promoters derived from appropriate eucaryotic genes. A class of promoters useful in yeast, for example, include promoters for synthesis of glycolytic enzymes, including those for 3-phosphoglycerate kinase (Hitzeman, et al., *J. Biol. Chem.* (1980) 255:2073). Other promoters include those from the enolase gene (Holland, M. J., et al. *J. Biol. Chem.* (1981) 256:1385) or the Leu2 gene obtained from YEp13 (Broach, J., et al., *Gene* (1978) 8:121).

Suitable mammalian promoters include the early and late promoters from SV40 (Fiers, et al., *Nature* (1978) 273:113) or other viral promoters such as those derived from polyoma, adenovirus II, bovine papilloma virus or avian sarcoma viruses. Suitable viral and mammalian enhancers are cited above.

The expression system is constructed from the foregoing control elements operably linked to the MHC sequences using standard methods, employing standard ligation and restriction techniques which are well understood in the art. Isolated plasmids, DNA sequences, or synthesized oligonucleotides are cleaved, tailored, and relegated in the form desired.

Site specific DNA cleavage is performed by treating with the suitable restriction enzyme (or enzymes) under conditions which are generally understood in the art, and the particulars of which are specified by the manufacturer or these commercially available restriction enzymes. See, e.g., New England Biolabs, Product Catalog. In general, about 1 ug of plasmid or DNA sequence is cleaved by one unit of enzyme in about 20 ul of buffer solution; in the examples herein, typically, an excess of restriction enzyme is used to insure complete digestion of the DNA substrate. Incubation times of about 1 hr to 2 hr at about 37° C. are workable, although variations can be tolerated. After each incubation, protein is removed by extraction with phenol/chloroform, and may be followed by ether extraction, and the nucleic acid recovered from aqueous fractions by precipitation with ethanol followed by running over a Sephadex G-50 spin column. If desired, size separation of the cleaved fragments may be performed by polyacrylamide gel or agarose gel electrophoresis using standard techniques. A general description of size separation is found in *Methods in Enzymology* (1980) 65:499–560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20 to 25° C. in 50 Mm Tris Ph 7.6, 50 Mm NaCl, 6 mM $MgCl_2$, 6 Mm DTT and 5–10 uM dNTPs. The Klenow fragment fills in a 5' sticky ends but chews back protruding 3' single strands, even through the four dNTPS, are present. If desired, selective repair can be performed by supplying only one of the, or selected, dNTPs within the limitations dictated by the nature of the sticky ends. After treatment with Klenow, the mixture is extracted with phenol/chloroform and ethanol precipitated followed by running over a Sephadex G-50 spin column.

Synthetic oligonucleotides are prepared using commercially available automated oligonucleotide synthesizers. Kinasing of single strands prior to annealing or for labeling is achieved using an excess, e.g., approximately 10 units of polynucleotide kinase to 0.1 nmole substrate in the presence of 50 mM Tris, pH 7.6, 10 mM $MgCl_2$, 5 mM dithiothreitol, 1–2 mM ATP, 1.7 pmoles $^{32}$P-ATP (2.9 mCi/mmole), 0.1 mM spermidine, 0.1 mM EDTA.

Ligations are performed in 15–30 ul volumes under the following standard conditions and temperatures: 20 mM Tris-HCl pH 7.5, 10 mM $MgCl_2$, 10 mM DTT, 33 ug/ml BSA, 10 mM–50 mM NaCl, and either 40 uM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 ug/ml total DNA concentrations (5–100 nM total end concentration). Intermolecular blunt end ligations (usually employing a 10–30 fold molar excess of linkers) are performed at 1 uM total ends concentration.

In vector construction employing "vector fragments," the vector fragment is commonly treated with bacterial alkaline phosphatase (BAP) in order to remove the 5' phosphate and prevent religation of the vector. BAP digestions are conducted at pH 8 in approximately 150 mM Tris, in the presence of $Na^+$ and $Mg^{+2}$ using about 1 unit of BAP per ug of vector at 60° C. for about 1 hr. In order to recover the nucleic acid fragments, the preparation is extracted with phenol/chloroform and ethanol precipitated and desalted by application to a Sephadex G-50 spin column. Alternatively, religation can be prevented in vectors which have been double digested by additional restriction enzyme digestion of the unwanted fragments.

For portions of vectors derived from cDNA or genomic DNA which require sequence modifications, site specific primer directed mutagenesis can be used. This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a stand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered.

In the proteins of the invention, however, a synthetic gene is conveniently employed. The gene design can include restriction sites which permit easy manipulation of the gene to replace coding sequence portions with these encoding analogs.

Correct ligations for plasmid construction can be confirmed by first transforming *E. coli* strain MM294 obtained from *E. coli* Genetic Stock Center, CGSC #6135, or other suitable host with the ligation mixture. Successful transformants are selected by ampicillin, tetracycline or other antibiotic resistance or using other markers depending on the mode of plasmid construction, as is understood in the art. Plasmid from the transformants are then prepared according to the method of Clewell, D. B., et al., *Proc. Natl. Acad. Sci. USA* (1969) 62:1159, optionally following chloramphenicol amplification (Clewell, D. B., *J. Bacteriol.* (1972) 110:667). The isolated DNA is analyzed by restriction and/or sequenced by the dideoxy method of Sanger, F., et al., *Proc. Natl. Acad. Sci. USA* (1977) 74:5463 as further described by Messing, et al., *Nucleic Acids Res.* (1981) 9:309, or by the method of Maxam, et al., *Methods in Enzymology* (1980) 65:499.

The constructed vector is then transformed into a suitable host for production of the protein. Depending on the host cell used, transformation is done using standard techniques appropriate to such cells. The calcium treatment employing calcium chloride, as described by Cohen, S. N., *Proc. Natl. Acad. Sci. USA* (1972) 69:2110, or the RbCl method described in Maniatis, et al., *Molecular Cloning: A Laboratory Manual* (1982) Cold Spring Harbor Press, p. 254 is used for procaryotes or other cells which contain substantial cell wall barriers. For mammalian cells without such cell walls, the calcium phosphate precipitation method of Graham and van der Eb, *Virology* (1978) 52:546 or electroporation is preferred. Transformations into yeast are carried out according to the method of Van Solingen, P., et al., *J. Bacter.* (1977) 130:946 and Hsiao, C. L., et al., *Proc. Natl. Acad. Sci. USA* (1979) 76:3829.

The transformed cells are then cultured under conditions favoring expression of the MHC sequence and the recombinantly produced protein recovered from the culture.

Antigenic Pentides

The autoantigenic proteins or tissues for a number of autoimmune diseases are known. For example, in experimentally induced autoimmune diseases, antigens involved in pathogenesis have been characterized: in arthritis in rat and mouse, native type-II collagen is identified in collagen-induced arthritis, and mycobacterial heat shock protein in adjuvant arthritis (Stuart et al. (1984), *Ann. Rev. Immunol.* 2:199–218; van Eden et al. (1988), *Nature* 331:171–173.); thyroglobulin has been identified in experimental allergic thyroiditis (EAT) in mouse (Maron et al. (1988), *J. ExR. Med.* 152:1115–1120); acetyl choline receptor (AChR) in experimental allergic myasthenia gravis (EAMG) (Lindstrom et al. (1988), *Adv. Immunol.* 42:233–284); and myelin basic protein (MBP) and proteolipid protein (PLP) in experimental allergic encephalomyelitis (EAE) in mouse and rat (See Acha-Orbea et al., supra). In addition, for example, target antigens have been identified in humans: type-II collagen in human rheumatoid arthritis (Holoshitz et al. (1986), *Lancet* ii:305–309); and acetyl choline receptor in myasthenia gravis (Lindstrom et al. (1988), supra) all of the above are incorporated herein by reference.

It is believed that the presentation of antigen by the MHC glycoprotein on the surface of antigen-presenting cells (APCs) occurs subsequent to the hydrolysis of antigenic proteins into smaller peptide units. The location of these smaller segments within the antigenic protein can be determined empirically. These segments are thought to be 8–15 residues in length, and contain both the agretope (recognized by the MHC molecule) and the epitope (recognized by T cell receptor on the T-helper cell). The epitope itself is a contiguous or non-contiguous sequence of 5–6 amino acids which recognizes the antigen-specific receptor of T-helper cells. The agretope is a continuous or non-contiguous sequence which is responsible for the association of the peptide with the MHC glycoproteins.

The empirical process of determining the relevant 8–15 amino acid subunits is illustrated using the alpha subunit of the acetylcholine receptor of skeletal muscle. In myasthenia gravis (MG) an autoimmune response is directed to a region of this subunit. A loss of the acetyl choline receptors on the postsynaptic membrane of the neuromuscular junction causes the MG symptoms.

In MG, autoantibodies against the alpha subunit of the acetylcholine receptor (AChR) are associated with the autoimmune response directed at the AChR. Eighty five percent of MG patients have autoantibodies reactive with the alpha subunit. Of these, 60% have antibodies that bind to a peptide segment of the alpha subunit called the main immunogenic region (MIR) which is located between residues 60 and 80 (Tzartos and Lindstrom, *Proc. Natl. Acad. Sci. USA* (1980) 77:755). The peptide segments recognized by autoreactive human T cells also are located on the alpha subunit (Hohfield, et al., *Proc. Natl. Acad. Sci. USA* (1987). The epitopes recognized by these T cells lie between residues 1–30, 125–147, 169–181, 257–271 and 351–368. In addition, in humans the AChR peptides 195–212 and 257–269 have been partially characterized as epitopes in myasthenia gravis patients of the HLA-DR5 and HLA-DR3, DQW2 MHC haplotypes, respectively (See Acha-Orbea (1989), supra).

The peptides carrying agretopes permitting presentation of the epitopes associated with alpha subunit of this receptor are readily determined. For example, determination of the appropriate peptides in a mouse model is carried out as follows. Strains of mice which, when immunized with Torpedo californicus AChR develop a disease with many of the features of human myasthenia gravis, are used as model. MHC Class II glycoproteins are isolated from spleen cells of mice of this strain using lectin and monoclonal antibody affinity supports. The purified MHC Class II proteins are incorporated into phospholipid vesicles by detergent dialysis. The resultant vesicles are then allowed to fuse to clean glass cover slips to produce on each a planar lipid bilayer containing MHC molecules as shown in FIG. 5 (Brian and McConnell, *Proc. Natl. Acad. Sci. USA* (1984) 81:6159, which is incorporated herein by reference).

One cover slip containing MHC Class II molecules embedded in the adherent planar lipid membrane is placed in each well of several 24-well culture plates. Each one of the approximately 40 overlapping 20-residue synthetic peptides corresponding to the alpha subunit sequence and containing one or more radiolabeled amino acid residues (prepared as described below) is placed in a well with cover slip and PBS and allowed to incubate several days. The extent of binding of peptide in the MHC Class II glycoprotein antigen binding site is measured by the amount of radio-activity incorporated into the MHC Class II-planar lipid membrane on the cover slip versus planar lipid membrane alone. Specific incorporation of radioactivity indicates that the bound peptide contains an agretope (MHC Class II peptide binding site) of one of the several species of MHC Class II molecules present in the planar lipid membrane. In this way, the set of agretopes for the alpha subunit of AChR is defined for the mouse strain that displays the symptoms of MG upon immunization with AChR or purified alpha subunit.

Next, each of the alpha subunit synthetic peptide segments that contain an agretope is again incorporated into the antigen binding site of isolated MHC Class II proteins embedded in planar lipid membranes on cover slips. One cover slip is added to each well of a 24-well culture plate, and spleen cells from mice immunized against AChR (and from which strain the adherent MHC Class II proteins were isolated) are added to each well. T cell hybridoma proliferation, as measured by tritiated thymidine uptake into DNA, indicates that the MHC Class II protein-bound peptide contains both an agretope and an epitope for binding to the T cell. Activation of T cell clones is determined by measuring IL-3 production (see, Quill et al., supra).

The Dupont apparatus and technique for rapid multiple peptide synthesis (RAMPS) is used to synthesize the members of a set of overlapping (10 residue overlap), 20-residue peptides from the alpha subunit of Torpedo californicus AChR. The sequence of this peptide is known and is shown in FIG. 6. One or more radioactive amino acids is incorporated into each synthetic peptide. The pentafluorphenyl active esters of side chain-protected, FMOC amino acids are used to synthesize the peptides, applying standard stepwise solid phase peptide synthetic methods, followed by standard side chain deprotection and simultaneous release of the peptide amide from the solid support.

Alternatively the overlapping sequences which include the putative segments of 8–15 amino acids of the antigenic protein, such as acetylcholine receptor protein, can be synthesized on the method of Geysen, H. M., et al. *J. Immun. Meth*. (1987) 102:274, which is incorporated herein by reference. The synthesized radio labeled peptides are tested by incubating them individually (on the plates) with purified MHC proteins which have been formulated into lipid membrane bilayers as above.

In multiple sclerosis (MS), which results in the destruction of the myelin sheath in the central nervous system, myelin basic protein (MBP), the major protein component of myelin is the principal autoantigen. Pertinent segments of the MBP protein are also determined empirically, using a strain of mice which develops experimental allergic encephalitis (EAG) when immunized with bovine myelin basic protein, the sequence of MBP is shown in FIG. 7.

Systemic lupus erythematosus (SLE) has a complex systemology, but results from an autoimmune response to red blood cells. Peptides which are the antigenic effectors of this disease are found in the proteins on the surface of red blood cells.

Rheumatoid arthritis (RA) is a chronic inflammatory disease resulting from an immune response to proteins found in the synovial fluid.

Insulin-dependent diabetes mellitus (IDDM) results from autoimmune attack on the beta cells within the Islets of Langerhans which are responsible for secretion of insulin. Circulating antibodies to Islets cells surface antigens and to insulin are known to precede IDDM. Critical peptides in eliciting the immune response in IDDM are believed to be portions of the insulin sequence and the beta cell membrane surface proteins.

The relevant antigenic peptide subunits, as they are relatively short, can readily by synthesized using standard automated methods for peptide synthesis. In the alternative, they can be made recombinantly using isolated or synthetic DNA sequences; though this is not the most efficient approach for peptides of this length.

Thus, in summary, a set of labeled test peptides is prepared, and those which bind to MHC in planar lipid membranes containing MHC proteins are shown to contain the agretope.

The identified peptides are then prepared by conventional solid phase synthesis and the subset which contain epitopes for the disease-inducing helper T cell clones is determined by incubation of the candidate peptides with murine antigen-presenting cells (APC) (or with isolated MHC complex) and spleen or lymph node T cells from mice immunized with the full length protein. Successful candidates will stimulate T cell proliferation in this system. This second, smaller, subset represents the suitable peptide component.

Formation of the Complex

The elements of the complex can be associated by standard means known in the art. The antigenic peptides can be associated noncovalently with the pocket portion of the MHC protein by, for example, mixing the two components. They can also be covalently bound using standard procedures by, for example, photo affinity labelling, (see e.g., Hall et al., *Biochemistry* 24:5702–5711 (1985), which is incorporated herein by reference).

For example, the AChR peptide 195–215, which has been characterized as an epitope in MG in humans and in mice, may be connected to the N-terminal antigen binding site of a polypeptide derived from an MHC antigen associated with MG. The amino acid sequence of the AChR peptide in one letter amino acid code is:

DTPYLDITYHFIMQRIPLYFV (SEQ ID NO: 6)

An oligonucleotide which encodes the peptide is synthesized using the known codons for the amino acid, preferably those codons which have preferred utilization in the organism which is to be used for expression are utilized in designing the oligonucleotide. Preferred codon utilizations for a variety of organisms and types of cells are known in the art. If, for example, expression is to be in *E. coli*, a suitable oligonucleotide sequence encoding AChR 195–215 could be:

5' GAC ACC CCG TAC CTG GAC ATC ACC TAC CAC TTC ATC ATG CAG CGT ATC CCG CTG TAC TTC CTG 3' (SEQ ID NO: 7).

This sequence may then be incorporated into a sequence encoding the peptides derived from the MHC antigen, utilizing techniques known in the art. The incorporation site will be such that, when the molecule is expressed and folded, the AChR peptide antigen will be available as an epitope for the target T cells.

In one protocol, the AChR 195–215 peptide is attached to the N-terminal end of the appropriate MHC molecule. If the recombinant complex is to be used in mice, for example, the AChR peptide may be incorporated into a sequence encoding either the I-$A^b$-alpha or I-$A^b$-beta chain. The sequences encoding these chains are known, and are shown in FIG. 8 (alpha chain), and FIG. 9 (beta chain); also shown in the figures are restriction enzyme sites and significant domains of the chains. If the AChR peptide is to be incorporated into the beta chain, for example, the oligonucleotide may be inserted as a replacement for the leader peptide. Methods of replacing sequences within polynucleotides are known in the art, examples of which are described in the section on the construction of plasmids.

A similar protocol may be used for incorporation of the AChR peptide into a sequence encoding a peptide derived from the appropriate human HLA antigen. For example, in humans, the haplotype DR2W2 is associated with MG. Hence, the AChR peptide may be incorporated into, for example, a sequence encoding a beta-chain of a DR2 allele. The structural basis in the DR subregion for the major serological specificities DR1–9 are known, as are the sequences encoding the HLA-DR-beta chains from a number of DR haplotypes. See, for e.g., Bell et al. (1987), *Proc. Natl. Acad. Sci. USA* 84:6234–6238 which are incorporated herein by reference.

As demonstrated above, the autoimmune antigen peptide and the MHC component may be linked via peptide linkages. However, other modes of linkage are obvious to those of skill in the art, and could include, for example, attachment via carbohydrate groups on the glycoproteins, including, e.g., the carbohydrate moieties of the alpha- and/or beta-chains.

Assessment of the Complex

The complexes of the invention can be assayed using an in vitro system or using an in vivo model. In the in vitro system, the complex is incubated with peripheral blood T cells from subjects immunized with, or showing immunity to, the protein or antigen responsible for the condition associated with the peptide of the complex. The successful complexes will induce anergy in syngeneic T cells and prevent proliferation of the T cells even upon stimulation with additional antigen.

In the in vivo system, T cells that proliferate in response to the isolated epitope or to the full length antigen in the presence of APC are cloned. The clones are injected into histocompatible animals which have not been immunized in order to induce the autoimmune disease. Symptoms related to the relevant complex should ameliorate or eliminate the symptoms of the disease.

Either of the types of complexes, i.e., with or without the effector component, may be used. In one mode the treatment is two-fold. The individual is treated with the complex of MHC-encoded antigen-presenting glycoprotein containing an effective portion of the antigen to down-regulate the immune system. Further down-regulation is achieved by treatment with the three component complex with includes the MHC-encoded antigen-presenting glycoprotein, an effective portion of antigen which is specific for the autoimmune disease being treated, and an effector component.

In addition, panels of complexes may be used for treatment.

For example, if it is suspected that more than one peptide of an antigen is involved in the autoimmune response, and/or if it is suspected that more than one antigen is involved, the individual may be treated with several complexes selected from a panel containing the effective portion of the appropriate MHC-encoded antigen-presenting polypeptides, and effective portions of antigens; these may be with or without effector components.

Administration of a labeled complex permits identification of those portions of the immune system involved in the disease, in diagnostic applications.

Selection of the MHC Complexes for Therapy and/ or Diagnosis

In order to select the MHC complexes of the invention which are to be used in the diagnosis or treatment of an individual for an autoimmune disease, the type of MHC antigens which are involved in the presentation of the autoantigen are identified.

Specific autoimmune dysfunctions are correlated with specific MHC types. A list of the DQ/DR haplotypes in humans and their associations with autoimmune diseases are shown in FIG. 10. Methods for identifying which alleles, and subsequently which MHC encoded polypeptides, are associated with an autoimmune disease are known in the art. A method described in EP 286447 is suitable. In this method several steps are followed. First, the association between an MHC antigen and the autoimmune disease is determined based upon genetic studies. The methods for carrying out these studies are known to those skilled in the art, and information on all known HLA disease associations in humans is maintained in the HLA and Disease Registry in Copenhagen. The locus encoding the polypeptide associated with the disease is the one that would bear the strongest association with the disease (See FIG. 10).

Second, specific alleles encoding the disease associated with MHC antigen/polypeptide are identified. In the identification of the alleles, it is assumed that the susceptibility allele is dominant. Identification of the allele is accomplished by determining the strong positive association of a specific subtype with the disease. This may be accomplished in a number of ways, all of which are known to those skilled in the art. E.g., subtyping may be accomplished by mixed lymphocyte response (MLR) typing and by primed lymphocyte testing (PLT). Both methods are described in Weir and Blackwell, eds., Handbook of Experimental Immunology, which is incorporated herein by reference. It may also be accomplished by analyzing DNA restriction fragment length polymorphism (RFLP) using DNA probes that are specific for the MHC locus being examined. E.g., Nepom (1986), Annals N.Y. Acad. Sci. 475, 1. Methods for preparing probes for the MHC loci are known to those skilled in the art. See, e.g., Gregersen et al. (1986), *Proc. Natl. Acad. Sci. USA* 79:5966; Weissman et al. in Medicine in Transition: the Centennial of the University of Illinois College of Medicine (E. P. Cohen, ed. 1981) all of which are incorporated herein by reference.

The most complete identification of subtypes conferring disease susceptibility is accomplished by sequencing of genomic DNA of the locus, or CDNA to mRNA encoded within the locus. The DNA which is sequenced includes the section encoding the hypervariable regions of the MHC encoded polypeptide. Techniques for identifying specifically desired DNA with a probe, for amplification of the desired region are known in the art, and include, for example, the polymerase chain reaction (PCR) technique.

Once the allele which confers susceptibility to the specific autoimmune disease is identified, the polypeptide encoded within the allele is also identifiable, i.e., the polypeptide sequence may be deduced from the sequence of DNA within the allele encoding it. The MHC antigen complexes of the invention used for diagnosis and/or therapy are derived from the effective portion of the MHC antigen associated with the autoimmune disease state and from an autoimmune antigen associated with the same disease state.

As an example, over 90% of rheumatoid arthritis patients have a haplotype of DR4(Dw4), DR4(Dw14) or DR1 (See FIG. 10). It is also known that a target antigen in human rheumatoid arthritis is type-II collagen. Hence, the complexes of the invention used for treatment or diagnosis of an individual with rheumatoid arthritis would include those containing a polypeptide derived from the DR4(Dw4), DR1 and/or DR4(Dw14) which is capable of antigen presentation for disease induction, or incapable of antigen presention for disease suppression, complexed with an effective portion of type-II collagen.

Figure 11:
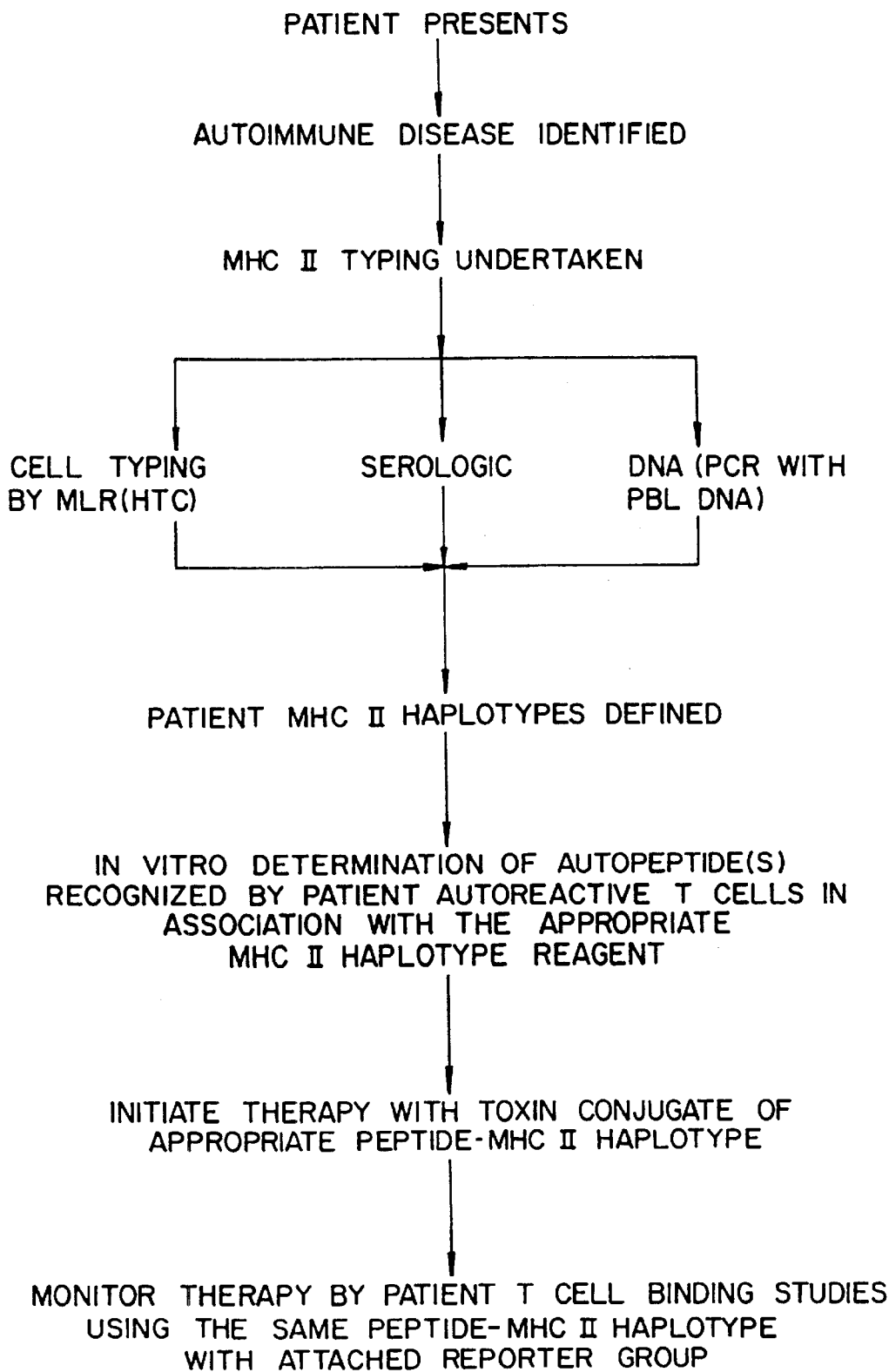
FIG. 11 shows a protocol suitable for the utilization of the complexes of the invention for the diagnosis and/or treatment of an autoimmune disease.

A protocol which may be suitable for the utilization of the complexes of the invention for the diagnosis and/or treatment of an autoimmune disease is depicted in FIG. 11. Briefly, an individual having (or susceptible to) an autoimmune disease is identified, and the autoimmune dysfunction is identified. Identification may be by symptomology and/or an examination of family histories. The individual's MHC type is determined by one or more of several methods known in the art, including, for example, cell typing by MLR, by serologic assay, and by DNA analysis (including RFLP and PCR techniques). The individuals T cells are examined in vitro, to determine the autopeptide(s) recognized by autoreactive T cells; this is accomplished utilizing labeled complexes of the invention, described supra, which are of the formula $X^1$ $MHC^2$ peptide, wherein X is a label moiety. After it is determined which complexes target the T cells, the individual is treated with complexes of the invention which are able to suppress the specific autoreactive T cell replication and/or those which kill the autoreactive T cells; these are complexes of the type $MHC^2$ peptide, and, $X^1$ $MHC^2$ peptide (wherein X is a moiety capable of killing the T cell), respectively. Therapy (as determined by the autoreactive T cells remaining) is monitored with T cell binding studies using the labeled complexes of the invention, described supra.

As used herein, the term "individual" encompasses all mammals and all vertebrates which possess basically equivalent MHC systems.

Model Systems for In Vivo Testing

The following are model systems for autoimmune diseases which can be used to evaluate the effects of the complexes of the invention on these conditions.

Systemic Lupus Erythematosus (SLE)

$F_1$ hybrids of autoimmune New Zealand black (NZB) mice and the phenotypically normal New Zealand White (NZW) mouse strain develop severe systemic autoimmune disease, more fulminant than that found in the parental NZB strain. These mice manifest several immune abnormalities, including antibodies to nuclear antigens and subsequent development of a fatal, immune complex-mediated glomerulonephritis with female predominance, remarkably similar to SLE in humans. Knight, et al., *J. Exp. Med.* (1978) 147:1653, which is incorporated hereby by reference.

In both the human and murine forms of the disease, a strong association with MHC gene products has been reported. HLA-DR2 and HLA-DR3 individuals are at a higher risk than the general population to develop SLE (Reinertsen, et al., *N. Engl. J. Med* (1970) 299:515), while in NZB/W $F_1$ mice (H-$2^{d/u}$), a gene linked to the h-$2^u$ haplotype derived from the NZW parent contributes to the development of the lupus-like nephritis.

The effect of the invention complex can be measured by survival rates and by the progress of development of the symptoms, such as proteinuria and appearance of anti-DNA antibodies.

Proteinuria is measured calorimetrically by the use of Uristix (Miles Laboratories, Inc., Elkhart, Ind.), giving an approximation of proteinuria as follows: trace, 10 mg/dl; 1+, 30 mg/dl; 100 mg/dl; 3+, 300 mg/dl; and 4+, 1000 mg/dl. The development of high grade proteinuria is significantly delayed by treatment of the mice with complex.

The presence of anti-DNA specific antibodies in NZB/W $F_1$ mice is determined by using a modification of a linked immunosorbent assay (ELISA) described by Zouali and Stollar, *J. Immunol. Methods* (1986) 90:105 which is incorporated herein by reference.

Myasthenia Gravis (MG)

Myasthenia gravis is one of several human autoimmune diseases linked to HLA-D. Safenberg, et al., *Tissue Antigens* (1978) 12:136; McDevitt, et al., *Arth. Rheum.* (1977) 20:59 which are incorporated herein by reference. In MG, antibodies to the acetyl choline receptors (AcChoR) impair neuromuscular transmission by mediating loss of AcChoR in the postsynaptic membrane.

SJL/J female mice are a model system for human MG. In these animals, experimental autoimmune myasthenia gravis (EAMG) is induced by immunizing the mice with soluble AcChoR protein from another species. Susceptibility to EAMG is linked in part to the MHC and has been mapped to the region within H-2. Christadoss, et al., *J. Immunol.* (1979) 123:2540.

AcChoR protein is purified from *Torpedo californica* and assayed according to the method of Waldor, et al., *Proc. Natl. Acad. Sci.* (USA) (1983) 80:2713, incorporated by reference. Emulsified AcChoR, 15 ug in complete Freund adjuvant, is injected intradermally among six sites on the back, the hind foot pads, and the base of the tail. Animals are reimmunized with this same regimen 4 weeks later.

Evaluation can be made by measurement of anti-AcChoR antibodies. Anti-AcChoR antibody levels are measured by a microliter ELISA assay as described in Waldor, et al., supra. The standard reagent volume is 50 ul per well. Reagents are usually incubated in the wells for 2 hr at RT. Five ug of AcChoR diluted in bicarbonate buffer, pH 9.6, is added to each well. After incubation with AcChoR, the plates are rinsed four times with a wash solution consisting of phosphate-buffer saline containing 0.05% Tween and 0.05% NaN$_3$. Mouse sera are diluted in 0.01M PBS (pH 7.2), 1.5 mfr MgCl$_2$, 2.0 mM 2-mercaptoethanol, 0.05% Tween-80, 0.05% NaN$_3$ (P-Tween buffer) and incubated on the plate. After the plate is washed, beta-galactosidase-conjugated sheep anti-mouse antibody diluted in P-Tween buffer is added to each well. After a final washing, the enzyme substrate, p-nitrophenyl-galctopyranoside is added to the plate, and the degree of substrate catalysis is determined from the absorbance at 405 nm after 1 hr.

Anti-AcChoR antibodies are expected to be present in the immunized with AcChoR mice as compared to nonimmunized mice. Treatment with complex is expected to significantly reduce the titer of anti-AcChoR antibodies in the immunized mice.

The effect of treatment with complex on clinical EAMG can also be assessed. Myasthenia symptoms include a characteristic hunched posture with drooping of the head and neck, exaggerated arching of the back, splayed limbs, abnormal walking, and difficulty in righting. Mild symptoms are present after a standard stress test, and should be ameliorated by administration of complex after a period of time after which antibody titer has fallen.

Rheumatoid Arthritis (RA)

In humans, susceptibility to rheumatoid arthritis is associated with HLA D/DR. The immune response in mice to native type II collagen has been used to establish an experimental model for arthritis with a number of histological and pathological features resembling human RA. Susceptibility to collagen-induced arthritis (CIA) in mice has been mapped to the H-2 I region, particularly the I-A subregion. Huse, et al., *Fed. Proc.* (1984) 43:1820.

Mice from a susceptible strain, DBA-1 are caused to have CIA by treatment of the mice with native type II collagen, using the technique described in Wooley and Luthra, *J. Immunol.* (1985) 134:2366, incorporated herein by reference.

In another model, adjuvant arthritis in rats is an experimental model for human arthritis, and a prototype of autoimmune arthritis triggered by bacterial antigens, Holoschitz, et al., *Prospects of Immunology* (CRC Press) (1986); Pearson *Arthritis Rheum.* (1964) 7:80. The disease the result of a cell-mediated immune response, as evidenced by its transmissibility by a clone of T cells which were reactive against the adjuvant (MT); the target self-antigen in the disease, based upon studies with the same cloned cells, appears to be part(s) of a proteoglycan molecule of cartilage.

Adjuvant disease in rats is produced as described by Pearson, supra, i.e., by a single injection of Freund's adjuvant (killed tubercle bacilli or chemical fractions of it, mineral oil, and an emulsifying agent) given into several depot sites, preferably intracutaneously or into a paw or the base of the tail. The adjuvant is given in the absence of other antigens.

The effect of complex treatment of manifestations of the disease are monitored. These manifestations are histopathological, and include an acute and subacute synovitis with proliferation of synovial lining cells, predominantly a mononuclear infiltration of the articular and particular tissues, the invasion of bone and articular cartilage by connective tissue pannus, and periosteal new bone formation, especially adjacent to affected joints. In severe or chronic cases, destructive changes occur, as do fibrous or bony ankylosis. These histopathological symptoms are expected to appear in control animals at about 12 days after sensitization to the Freund's adjuvant.

Insulin Dependent Diabetes Mellitus (IDDM)

IDDM is observed as a consequence of the selective destruction of insulin-secreting cells within the Islets of Langerhans of the pancreas. Involvement of the immune system in this disease is suggested by morphologic evidence of early infiltration of the Islets by mononuclear cells, by the detection of anti-islet cell antibodies, by the high frequency of HLA-DR3 and -DR4 alleles in IDDM populations, and by clinical associations between IDDM and various autoimmune diseases. An animal model for spontaneous IDDM and thyroiditis has been developed in the BB rat. As in humans, the rat disease is controlled in part by the genes encoding the MHC antigens, is characterized by islet infiltration, and is associated with the presence of anti-islet antibodies. The I-E equivalent Class II MHC antigens appear to be involved in manifestation of the autoimmune diseases in the BB rat. Biotard, et al., *Proc. Natl. Acad. Sci. USA* (1985) 82:6627.

In morphologic evaluation, insulitis is characterized by the presence of mononuclear inflammatory cells within the islets. Thyroiditis is characterized by focal interstitial lymphocytic infiltrate within the thyroid gland, as a minimum criterion. Most severe cases show diffuse extensive lymphocytic infiltrates, disruption of acini, fibrosis, and focal Hurthle call change. See Biotard et al., supra.

Treatment of the BB rats with complex of the invention is expected to ameliorate or prevent the manifestation of the clinical and morphological symptoms associated with IDDM and thyroiditis.

In another spontaneous model, the NOD mouse strain (H-2K$^d$D$^b$) is a murine model for autoimmune IDDM. The disease in these animals is characterized by anti-islet cell antibodies, severe insulitis, and evidence for autoimmune destruction of the beta-cells. Kanazawa, et al., *Diabetologia* (1984) 27:113. The disease can be passively transferred with lymphocytes and prevented by treatment with cyclosporin-A (Ikehara, et al., *Proc. Natl. Acad. Sci. USA* (1985) 82:7743; Mori, et al.), *Diabetologia* (1986) 29:244. Untreated animals develop profound glucose intolerance and ketosis and succumb within weeks of the onset of the disease. Seventy to ninety percent of female and 20–30% of male animals develop diabetes within the first six months of life. Breeding studies have defined at least two genetic loci responsible for disease susceptibility, one of which maps to the MHC. Characterization of NOD Class II antigens at both the serologic and molecular level suggest that the susceptibility to autoimmune disease is linked to I-A$_B$. Acha-Orbea and McDevitt, *Proc. Natl. Acad. Sci. USA* (1907) 84:235.

Treatment of Female NOD mice with complex is expected to lengthen the time before the onset of diabetes and/or to ameliorate or prevent the disease.

Experimental Allergic Encephalomyelitis (EAE)

Experimental allergic encephalomyelitis (EAE) is an induced autoimmune disease of the central nervous system which mimics in many respects the human disease of multiple sclerosis (MS). The disease can be induced in many species, including mice and rats.

The disease is characterized by the acute onset of paralysis. Perivascular infiltration by mononuclear cells in the CNS is observed in both mice and rats. Methods of inducing the disease, as well as symptomology, are reviewed in Aranson (1985) in The *Autoimmune Diseases* (eds. Rose and Mackay, Academic Press, Inc.) pp. 399–427, and in Acha-Orbea et al. (1989), *Ann. Rev. Imm.* 7:377–405.

One of the genes mediating susceptibility is localized in the MHC class II region (Moore et al. (1980), *J. Immunol.*

124:1815–1820). The best analyzed encephalitogenic protein is myelin basic protein (MBP), but other encephalitogenic antigens are found in the brain. The immunogenic epitopes have been mapped (see Acha-Orbea et al., supra.). In the PL mouse strains (H-2$^u$) two encephalitogenic peptides in MBP have been characterized: MBP peptide p35–47 (MBP 35–47), and acetylated (MBP 1–9).

The effect of the invention complexes on ameliorating disease symptoms in individuals in which EAE has been induced can be measured by survival rates, and by the progress of the development of symptoms.

Formulation and Administration

If the transmembrane region of the MHC subunit is included, the complexes of the invention are conveniently administered after being incorporated in lipid monolayers or bilayers. Typically liposomes are used for this purpose but any form of lipid membrane, such as planar lipid membranes or the cell membrane of a cell (e.g., a red blood cell) may be used. The complexes are also conveniently incorporated into micelles. The data presented in Example 2, below, shows that MHC-peptide complexes comprising dimeric MHC molecules exist primarily as aggregates.

Liposomes can be prepared according to standard methods, as described below. However, if the transmembrane region is deleted, the complex can be administered in a manner conventionally used for peptide-containing pharmaceuticals.

Administration is systemic and is effected by injection, preferably intravenous, thus formulations compatible with the injection route of administration may be used. Suitable formulations are found in *Remington's Pharmaceutical Sciences*, Mack Publishing Company, Philadelphia, Pa., 17th ed. (1985), which is incorporated herein by reference. A variety of pharmaceutical compositions comprising complexes of the present invention and pharmaceutically effective carriers can be prepared. The pharmaceutical compositions are suitable in a variety of drug delivery systems. For a brief review of present methods of drug delivery, see, Langer, *Science* 249:1527–1533 (1990) which is incorporated herein by reference.

In preparing pharmaceutical compositions of the present invention, it is frequently desirable to modify the complexes of the present invention to alter their pharmacokinetics and biodistribution. For a general discussion of pharmacokinetics, see, *Remington's Pharmaceutical Sciences*, supra, Chapters 37–39. A number of methods for altering pharmacokinetics and biodistribution are known to one of ordinary skill in the art (see, e.g., Langer, supra). For instance, methods suitable for increasing serum half-life of the complexes include treatment to remove carbohydrates which are involved in the elimination of the complexes from the bloodstream. Preferably, substantially all of the carbohydrate moieties are removed by the treatment. Substantially all of the carbohydrate moieties are removed if at least about 75%, preferably about 90%, and most preferably about 99% of the carbohydrate moieties are removed. Conjugation to soluble macromolecules, such as proteins, polysaccharides, or synthetic polymers, such as polyethylene glycol, is also effective. Other methods include protection of the complexes in vesicles composed of substances such as proteins, lipids (for example, liposomes), carbohydrates, or synthetic polymers.

Liposomes of the present invention typically contain the MHC-peptide complexes positioned on the surface of the liposome in such a manner that the complexes are available for interaction with the T cell receptor. The transmembrane region is usually first incorporated into the membrane at the time of forming the membrane. The liposomes can be used to target desired drugs (e.g. toxins or chemotherapeutic agents) to particular autoreactive T cells. Alternatively, the complexes embedded in the liposome may be used to induce anergy in the targeted cells.

Liposome charge is an important determinant in liposome clearance from the blood, with negatively charged liposomes being taken up more rapidly by the reticuloendothelial system (Juliano, *Biochem. Biophys. Res. Commun.* 63:651 (1975)) and thus having shorter half-lives in the bloodstream. Liposomes with prolonged circulation half-lives are typically desirable for therapeutic and diagnostic uses. For instance, liposomes which can be maintained from 8, 12, or up to 24 hours in the bloodstream are particularly preferred.

Typically, the liposomes are prepared with about 5–15 mole percent negatively charged phospholipids, such as phosphatidylglycerol, phosphatidylserine or phosphatidylinositol. Added negatively charged phospholipids, such as phosphatidylglycerol, also serve to prevent spontaneous liposome aggregating, and thus minimize the risk of undersized liposomal aggregate formation. Membrane-rigidifying agents, such as sphingomyelin or a saturated neutral phospholipid, at a concentration of at least about 50 mole percent, and 5–15 mole percent of monosialylganglioside, may provide increased circulation of the liposome preparation in the bloodstream, as generally described in U.S. Pat. No. 4, 837,028, incorporated herein by reference.

Additionally, the liposome suspension may include lipid-protective agents which protect lipids against free-radical and lipid-peroxidative damages on storage. Lipophilic free-radical quenchers, such as α tocopherol and water-soluble iron-specific chelators, such as ferrioxianine, are preferred.

A variety of methods are available for preparing liposomes, as described in, e.g., Szoka et al., *Ann. Rev. Biophys. Bioeng.* 9:467 (1980), U.S. Pat. Nos. 4, 235,871, 4,501,728 and 4,837,028, all of which are incorporated herein by reference. One method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powderlike form. This film is covered with an aqueous solution of the targeted drug and the targeting component and allowed to hydrate, typically over a 15–60 minute period with agitation. The size distribution of the resulting multilamellar vesicles can be shifted toward smaller sizes by hydrating the lipids under more vigorous agitation conditions or by adding solubilizing detergents such as deoxycholate.

The hydration medium contains the targeted drug at a concentration which is desired in the interior volume of the liposomes in the final liposome suspension. Typically the drug solution contains between 10–100 mg/ml of the complexes in a buffered saline solution.

Following liposome preparation, the liposomes may be sized to achieve a desired size range and relatively narrow distribution of liposome sizes. One preferred size range is about 0.2–0.4 microns, which allows the liposome suspension to be sterilized by filtration through a conventional filter, typically a 0.22 micron filter. The filter sterilization method can be carried out on a high through-put basis if the liposomes have been sized down to about 0.2–0.4 microns.

Several techniques are available for sizing liposome to a desired size. One sizing method is described in U.S. Pat. No. 4,737,323, incorporated herein by reference. Sonicating a liposome suspension either by bath or probe sonication produces a progressive size reduction down to small unilamellar vesicles less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. In both methods, the particle size distribution can be monitored by conventional laser-beam particle size discrimination.

Extrusion of liposome through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size.

Even under the most efficient encapsulation methods, the initial sized liposome suspension may contain up to 50% or more complex in a free (nonencapsulated) form.

Several methods are available for removing non-entrapped compound from a liposome suspension. In one method, the liposomes in the suspension are pelleted by high-speed centrifugation leaving free compound and very small liposomes in the supernatant. Another method involves concentrating the suspension by ultrafiltration, then resuspending the concentrated liposomes in a replacement medium. Alternatively, gel filtration can be used to separate large liposome particles from solute molecules.

Following the above treatment, the liposome suspension is brought to a desired concentration for use in intravenous administration. This may involve resuspending the liposomes in a suitable volume of injection medium, where the liposomes have been concentrated, for example by centrifugation or ultrafiltration, or concentrating the suspension, where the drug removal step has increased total suspension volume. The suspension is then sterilized by filtration as described above. The liposomes comprising the MHC-peptide complex may be administered parenterally or locally in a dose which varies according to, e.g., the manner of administration, the drug being delivered, the particular disease being treated, etc.

Micelles are commonly used in the art to increase solubility of molecules having nonpolar regions. One of skill will thus recognize that micelles are useful in compositions of the present invention. Micelles comprising the complexes of the invention are prepared according to methods well known in the art (see, e.g., *Remington's Pharmaceutical Sciences*, supra, Chap. 20). Micelles comprising the complexes of the present invention are typically prepared using standard surfactants or detergents.

Micelles are formed by surfactants (molecules that contain a hydrophobic portion and one or more ionic or otherwise strongly hydrophilic groups) in aqueous solution. As the concentration of a solid surfactant increases, its monolayers adsorbed at the air/water or glass/water interfaces become so tightly packed that further occupancy requires excessive compression of the surfactant molecules already in the two monolayers. Further increments in the amount of dissolved surfactant beyond that concentration cause amounts equivalent to the new molecules to aggregate into micelles. This process begins at a characteristic concentration called "critical micelle concentration".

The shape of micelles formed in dilute surfactant solutions is approximately spherical. The polar head groups of the surfactant molecules are arranged in an outer spherical shell whereas their hydrocarbon chains are oriented toward the center, forming a spherical core for the micelle. The hydrocarbon chains are randomly coiled and entangled and the micellar interior has a nonpolar, liquid-like character. In the micelles of polyoxyethylated nonionic detergents, the polyoxyethlene moieties are oriented outward and permeated by water. This arrangement is energetically favorable since the hydrophilic head groups are in contact with water and the hydrocarbon moieties are removed from the aqueous medium and partly shielded from contact with water by the polar head groups. The hydrocarbon tails of the surfactant molecules, located in the interior of the micelle, interact with one another by weak van der Waals forces.

The size of a micelle or its aggregation number is governed largely by geometric factors. The radius of the hydrocarbon core cannot exceed the length of the extended hydrocarbon chain of the surfactant molecule. Therefore, increasing the chain length or ascending homologous series increases the aggregation number of spherical micelles. For surfactants whose hydrocarbon portion is a single normal alkyl chain, the maximum aggregation numbers consistent with spherical shape are approximately 27, 39, 54, 72, and 92 for $C_8$, $C_{10}$, $C_{12}$, $C_{14}$ and $C_{16}$, respectively. If the surfactant concentration is increased beyond a few percent and if electrolytes are added (in the case of ionic surfactants) or the temperature is raised (in the case of nonionic surfactants), the micelles increase in size. Under these conditions, the micelles are too large to remain spherical and become ellipsoidal, cylindrical or finally lamellar in shape.

Common surfactants well known to one of skill in the art can be used in the micelles of the present invention. Suitable surfactants include sodium laureate, sodium oleate, sodium lauryl sulfate, octaoxyethylene glycol monododecyl ether, octoxynol 9 and PLURONIC F-127® (Wyandotte Chemicals Corp.). Preferred surfactants are nonionic polyoxyethylene and polyoxypropylene detergents compatible with IV injection such as, TWEEN-80®, PLURONIC F-68®, n-octyl-β-D-glucopyranoside, and the like. In addition, phospholipids, such as those described for use in the production of liposomes, may also be used for micelle formation.

Since the MHC subunits of the present invention comprise a lipophilic transmembrane region and a relatively hydrophilic extracellular domain, mixed micelles are formed in the presence of common surfactants or phospholipids and the subunits. The mixed micelles of the present invention may comprise any combination of the subunits, phospholipids and/or surfactants. Thus, the micelles may comprise subunits and detergent, subunits in combination with both phospholipids and detergent, or subunits and phospholipid.

For pharmaceutical compositions which comprise the complexes of the present invention, the dose will vary according to, e.g., the particular complex, the manner of administration, the particular disease being treated and its severity, the overall health and condition of the patient, and the judgment of the prescribing physician. Dosage levels for murine subjects are generally between about 10 $\mu$g and about 500 $\mu$g. A total dose of between about 50 $\mu$g and about 300 $\mu$g, is preferred. For instance, in treatments provided over the course of a disease, three 25 $\mu$g or 100 $\mu$g doses are effective. Total dosages range between about 0.5 and about 25 mg/kg, preferably about 3 to about 15 mg/kg.

The pharmaceutical compositions are intended for parenteral, topical, oral or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, and capsules.

Preferably, the pharmaceutical compositions are administered intravenously. Thus, this invention provides compositions for intravenous administration which comprise a solution of the complex dissolved or suspended in an acceptable carrier, preferably an aqueous carrier. A variety of aqueous carriers may be used, e.g., water, buffered water, 0.4% saline, and the like. For instance, phosphate buffered saline (PBS) is particularly suitable for administration of soluble complexes of the present invention. A preferred formulation is PBS containing 0.02% TWEEN-80. These compositions may be sterilized by conventional, well-known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of the complex can vary widely, i.e., from less than about 0.05%, usually at or at least about 1% to as much as 10 to 30% by weight and will be selected primarily by fluid volumes, viscosities, etc., in accordance with the particular mode of administration selected. Preferred concentrations for intravenous administration are about 0.02% to about 0.1% or more in PBS.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient.

For aerosol administration, the complexes are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol, and the polyoxyethylene and polyoxypropylene derivatives of these esters. Mixed esters, such as mixed or natural glycerides may be employed. The surfactant may constitute 0.1%–20% by weight of the composition, preferably 0.25–5%. The balance of the composition is ordinarily propellant. Liquefied propellants are typically gases at ambient conditions, and are condensed under pressure. Among suitable liquefied propellants are the lower alkanes containing up to 5 carbons, such as butane and propane; and preferably fluorinated or fluorochlorinated alkanes. Mixtures of the above may also be employed. In producing the aerosol, a container equipped with a suitable valve is filled with the appropriate propellant, containing the finely divided compounds and surfactant. The ingredients are thus maintained at an elevated pressure until released by action of the valve.

The compositions containing the complexes can be administered for therapeutic, prophylactic, or diagnostic applications. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective dose." Amounts effective for this use will depend on the severity of the disease and the weight and general state of the patient. As discussed above, this will typically be between about 0.5 mg/kg and about 25 mg/kg, preferably about 3 to about 15 mg/kg.

In prophylactic applications, compositions containing the complexes of the invention are administered to a patient susceptible to or otherwise at risk of a particular disease. Such an amount is defined to be a "prophylactically effective dose." In this use, the precise amounts again depend on the patient's state of health and weight. The doses will generally be in the ranges set forth above.

In diagnostic applications, compositions containing the appropriately complexes or a cocktail thereof are administered to a patient suspected of having an autoimmune disease state to determine the presence of autoreactive T cells associated with the disease. Alternatively, the efficacy of a particular treatment can be monitored. An amount sufficient to accomplish this is defined to be a "diagnostically effective dose." In this use, the precise amounts will depend upon the patient's state of health and the like, but generally range from 0.01 to 1000 mg per dose, especially about 10 to about 100 mg per patient.

Kits can also be supplied for therapeutic or diagnostic uses. Thus, the subject composition of the present invention may be provided, usually in a lyophilized form in a container. The complexes, which may be conjugated to a label or toxin, or unconjugated, are included in the kits with buffers, such as Tris, phosphate, carbonate, etc., stabilizers, biocides, inert proteins, e.g., serum albumin, or the like, and a set of instructions for use. Generally, these materials will be present in less than about 5% wt. based on the amount of complex and usually present in total amount of at least about 0.001% wt. based again on the protein concentration. Frequently, it will be desirable to include an inert extender or excipient to dilute the active ingredients, where the excipient may be present in from about 1 to 99% wt. of the total composition. Where an antibody capable of binding to the complex is employed in an assay, this will usually be present in a separate vial. The antibody is typically conjugated to a label and formulated according to techniques well known in the art.

The following example illustrates, but does not limit, the invention.

EXAMPLE 1

Down-Regulation of T cells In Vitro with a Complex of Mouse I-$A^k$ and rat MBP Peptide The efficacy of Class II MHC-peptide complexes in induction of nonresponsiveness or anergy in T cell clones directed against epitopes of myelin basic protein (MBP), known to induce experimental allergic encephalomyelitis in mice, a disease model which mimics human multiple sclerosis, is shown below.

T cell clones AJ1.2 and 4R3.4 prepared by immunization of mice against rat MBP peptide (1–11) and characterized for antigen specificity were obtained from Dr. Pat Jones of Stanford University.

The I-$A^k$ complex with rat NSF peptide was formed utilizing purified mouse I-$A^k$ and synthetic rat MBP peptide (1–13), the sequence for which is known (Zamvil et al. (1986), *Nature* 324:258260), and which is:

Ac-ASQKRPSQRHGSK (SEQ ID NO: 8)

Figure 12:
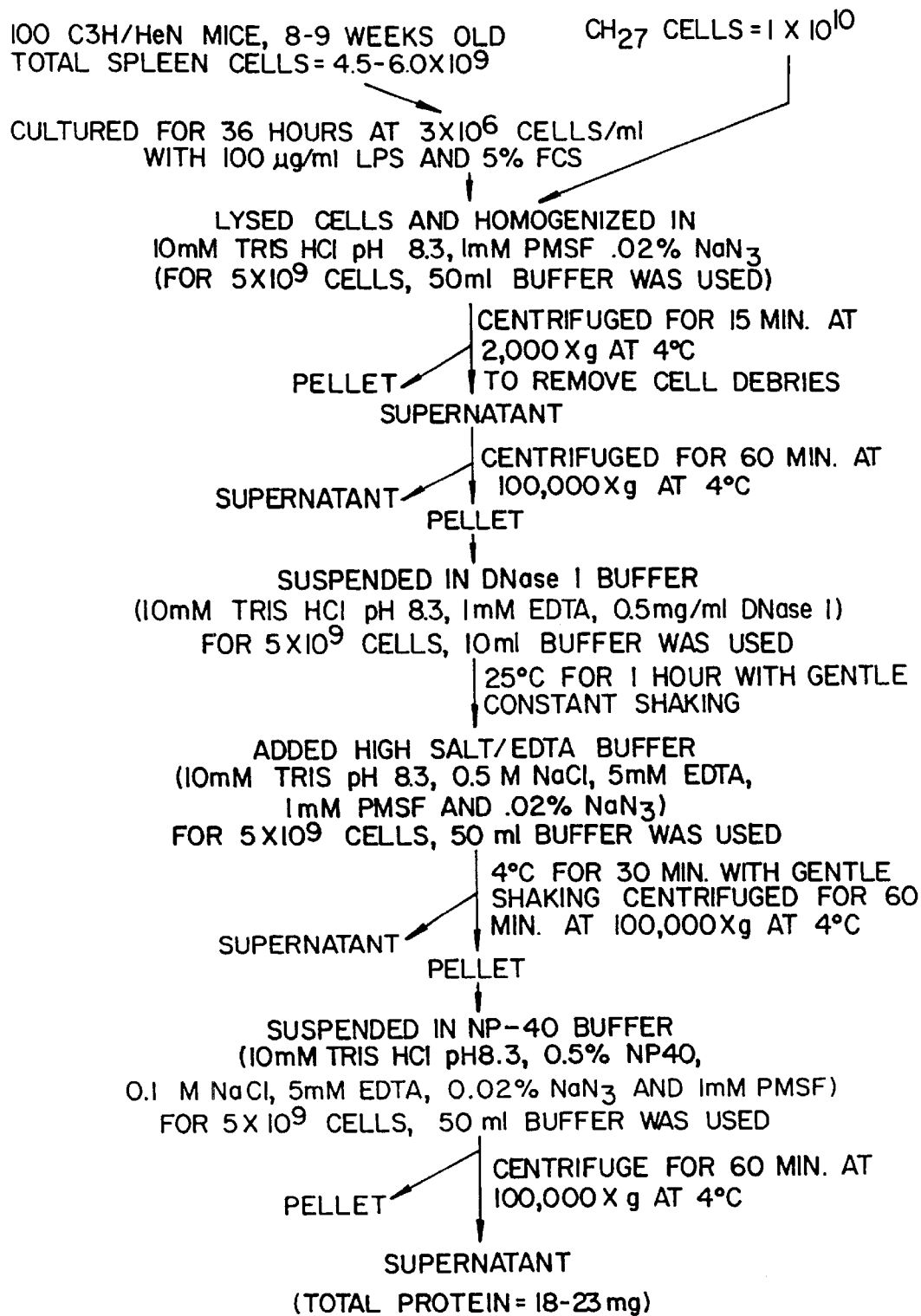
FIG. 12 shows a scheme for the preparation of I-$A^k$ containing NP-40 soluble membrane extracts.
Figure 13B:
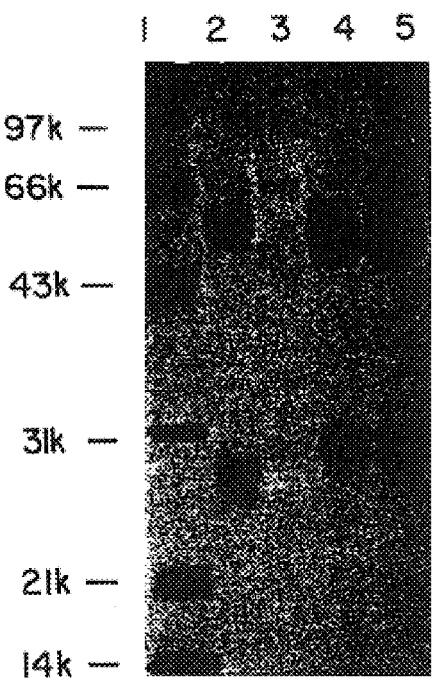
FIG. 13B is a copy of a gel showing the purity of 10–2.16 monoclonal antibody purified by the scheme in FIG. 13A.
Figure 15:
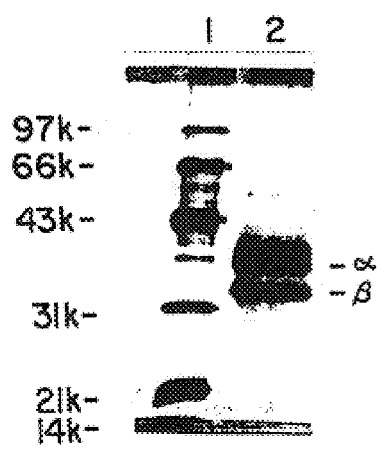
FIG. 15 is a polyacrylamide gel showing the purity of I-$A^k$ purified by the scheme in FIG. 14.

Mouse I-$A^k$ was purified by a modified method based upon Turkewitz et al., supra. Basically, a soluble membrane extract of cells containing I-$A^k$ was prepared using NP-40. I-$A^k$ from the extract was purified by affinity chromatography, using a column containing 10–2.16 antibodies, which had been purified by affinity chromatography on Protein-A, and which were coupled to CNBr activated Sepharose 4b. The preparation schemes for the NP-40 soluble membrane extract, for the purification of 10–2.16 Mab and its coupling to CnBr activated Sepharose 4B, and for the purification of I-$A^k$, are shown in FIGS. 12, 13a and 14, respectively. FIG. 13b is a copy of a polyacrylamide gel showing the Purity of the purified 10–2.16 antibody. The purity of I-$A^k$, as monitored by polyacrylamide gel analysis, is shown in FIG. 15.

In order to form the complex of I-$A^k$ and rat MBP peptide, ten ug of affinity-purified I-$A^k$ in PBS containing 30 mM octyl glucoside and 50-fold molar excess of HPLC-purified MBP peptide were mixed in a total volume of 125 ul. Samples were incubated at 37° C. for 16 hours with constant shaking and were either separated from peptide by G-24 Sephadex desalting for liposome preparation or, for cell studies, were dialyzed against PBS followed by RPMI media for 36 hours at 4° C.

The introduction of the I-$A^K$-MBP peptide complex into liposomes was as follows. A lipid solution consisting of cholesterol:dipalmitoylphosphatidyl choline (DPPC):dipalmitoylphosphatidyl ethanolamine-fluorescein (DPPEF) at a molar ration of 25:75:2 was prepared in chloroform containing 30 mM octyl glucoside (OG). Lipid was dried under vacuum and preformed I-$A^k$-peptide complex in PBS containing 17 mM OG was mixed with dried lipid at a ration of 5:1 (w/w). The mixture was vortexed for 2–3 minutes, cooled to 4° C., and finally dialyzed against PBS followed by RPMI media for 36 at 4° C. In experiments using (125-I)-labeled I-$A^k$, no fluoresceinated lipid was included in the lipid mixture, and the incorporation of I-$A^k$ into liposomes was measured by scintigraphy.

Planar lipid membranes were prepared on sterile 12-mm glass coverslips using 50–100 ul of liposomes containing affinity-purified I-$A^k$ alone or purified I-$A^k$+MBP(1–13) by the method of Watts et al. (1985), *Proc. Natl. Acad. Sci. USA* 82:5480–5484, which is incorporated herein by reference. The presence of I-$A^k$ in planar membranes was confirmed by fluorescence microscopy after staining with fluorescent anti-I-$A^k$ anti-body. No fluorescence above background was noted upon staining with fluorescent anti-I-$A^d$.

AJ1.2 and 4R3.4 cells obtained six to eight days after MBP peptide stimulation were washed twice, and the 4×10$^5$ cells were added to planar membranes. The plates were incubated for 48–72 hours in 5% $CO_2$ at 37° C. and then examined visually for formation of colonies.

The effects of detergent-solubilized Class II molecules were examined by culturing 1×10$^5$ AJ1.2 or 4R3.4 cells with 50–100 ul of purified I-$A^k$ alone, purified I-$A^k$ plus MBP (1–13) and medium alone for five hours at 37° C. in 5% $CO_2$. Following this incubation the cells were diluted to 900 ul and tested for their ability to respond to antigen-presenting cells (APC) and antigen [MBP(1–13)] in a proliferation assay. Uptake of 3-(4,5-dimethyl-thiazol-2-7')-2,5 diphenyltetrazolium bromide (MTT) was used as an indication of cell proliferation. Although DNA synthesis, usually monitored by $^3$H-thymidine uptake, and the activity of mitochondria, measured by MTT uptake, are different cellular functions, it has been demonstrated that these two activities, monitored three days after initiation of stimulation of spleen cell cultures, tracked each other very well (Molecular Device Application Bulletin Number 011-A, Feb. 9, 1988).

Data are presented as % suppression of proliferation of cells incubated with Class I+Ag compared to cells cultured with medium alone and were calculated by using the formula:

(O.D.)570 [T cells$_a$+Spleen cells+MBP(1–11)]–(O.D.) 570 [T cells$_b$+Spleen cells](O.D.)570 [T cells$_c$+Spleen cells+MBP(1–13)]–(O.D.) 570 [T cells$_c$+Spleen cells]

wherein

T cells$_a$=T cells preincubated with I-$A^k$ -MBP(1–13) complex

T cells$_b$=T cells preincubated with I-$A^k$ -MBP(1–13) alone

T cells$_c$=T cells preincubated with medium.

Since proliferation of cells cultured in the presence of Class II MHC alone was generally equal to cells cultured with medium alone in most studies, this latter number was used in obtaining % suppression. The Standard Deviation of triplicate wells was <10% in the majority of experiments.

Initially two qualitative studies were performed to determine whether pretreatment with I-$A^k$+MBP(1–13) will alter the binding of T cell clones to planar membranes prepared from liposomes containing I-$A^k$+MBP(1–13). AJ1.2 cells were used for these studies because they formed characteristic colonies on planar membranes in the presence of MBP(1–13) alone, i.e., without antigen presenting cells (APC). Preincubation of AJ1.2 cells with I-$A^k$+MBP(1–13) for five hours inhibited the number of colonies formed on planar membranes compared to cells incubated with I-$A^k$ or medium alone. In the second experiment, AJ1.2 cells were incubated with liposomes containing I-$A^k$+MBP(1–13) or with I-$A^k$ alone for five hours and then added to planar membranes prepared as described above. As noted previously with detergent-solubilized I-$A^k$ MBP(1–13), culturing of cells with liposome containing I-$A^k$+MBP(1–13) reduced the number of colonies in comparison to cells incubated with liposomes containing I-$A^k$ alone. Although colonies could not be counted accurately, clear differences in their number were evident.

Because these studies did not allow quantitation of the effects of I-$A^k$+MBP(1–13) on the function of T cell clones, we examined the effects of preincubation with this complex on the proliferation of 4R3.4 or AJ1.2 cells in the presence of APCs and MBP(1–13). Therefore, 4R3.4 or AJ1.2 cells were preincubated with 50–100 ul of I-$A^k$+MBP(1–13), I-$A^k$, or medium alone for five hours at 37° C. The cells were then diluted to an appropriate concentration and added to APC. Antigen [MBP(1–13)] was added to a final concentration ranging from 13.3 um to 53.2 um.

APC used in the study were prepared from spleens of female A/J mice. Briefly, spleens were removed and single cell suspensions were prepared by gentle teasing between the frosted ends of sterile microscope slides. Red cells were lysed by hypotonic shock. The remaining cells were washed twice with RPMI containing antibiotics and incubated with 10 micrograms/ml mitomycin-C for 1 hour at 37° C. Following this incubation, spleen cells were washed five times with RPMI containing antibiotics, counted, and used as APC's.

Figure 16:
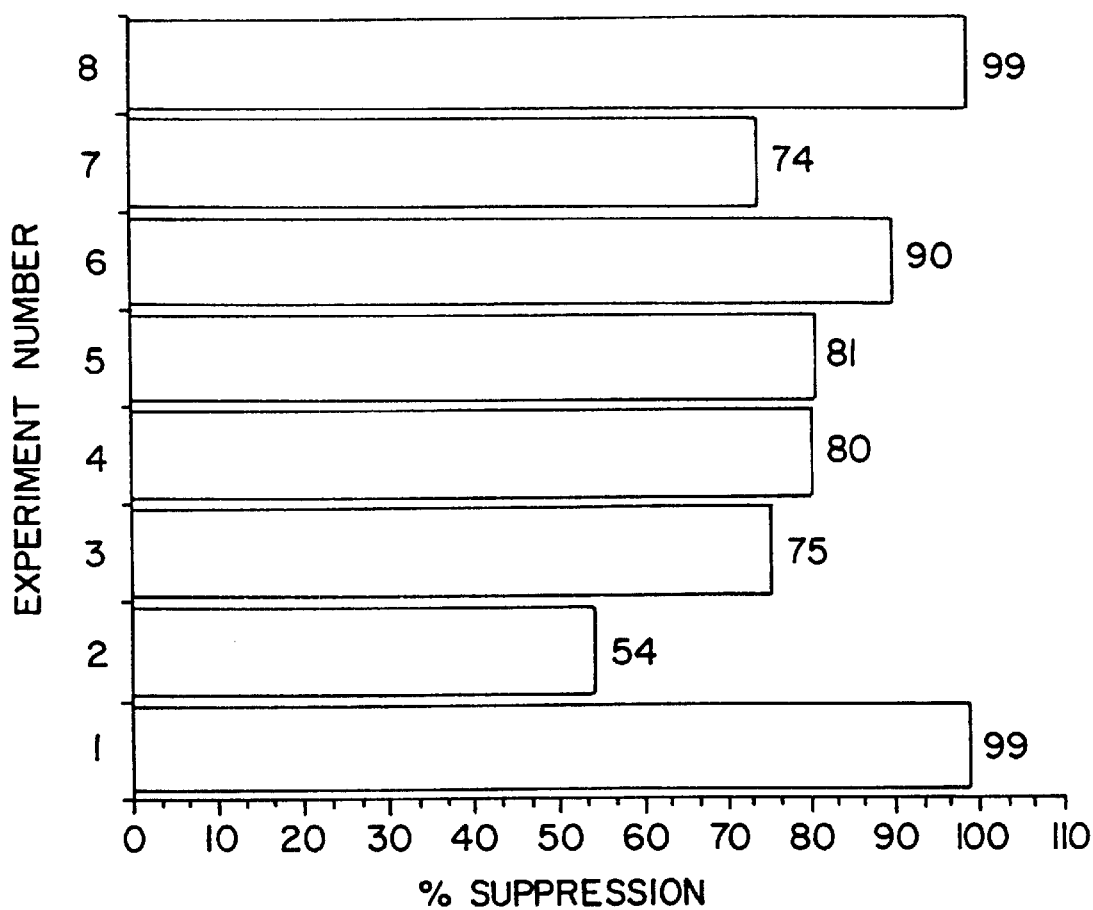
FIG. 16 is a bar graph showing the results of eight studies on the inhibition of proliferation by a complex containing I-$A^k$ and MBP (1–13).

Following a 72-hour incubation period of the cells with APC and MBP(1–13), the extent of proliferation was quantitated using MTT uptake. The results of eight such studies are summarized in FIG. 16. In studies 1, 3, and 4, 4R3.4 cells were incubated as above. In study 2, 4R3.4 cells were preincubated with liposomes containing I-A$^k$+MBP(1–13) or I-A$^k$ alone. T cells were then separated from unbound liposomes by centrifugation through a 10% Ficoll solution, washed, and used in proliferation assays. Studies 5 through 8 were carried out with the clone AJ1.2. Cells incubated with I-A$^k$ alone proliferated to the same extent as cells cultured in medium. T cell clones preincubated in this manner did not proliferate in the absence of APC.

The data presented above demonstrate that the complex of Class II MHC+MBP(1–13) induces dramatic nonresponsiveness in T cell clones specific for MBP(1–11). In addition, the data show that this complex was immunologically reactive with, and hence bound to the MBP-stimulated T cell clones.

Preparation and Stability of Human HLA-DR2-MBP Complexes

The optimum pH for maximum binding of human MBP (83–102) peptide to HLA-DR2 was determined to be pH 7. Affinity-purified DR2 from homozygous lymphoblastoid cells was incubated with 10 fold molar excess of radioiodinated MBP(83–102) peptide at 37° C. for 48 hours at various pH. The unbound peptide was removed by dialysis and the amount of bound peptide was calculated from the silica gel TLC assay. Samples were also analyzed on reduced and non-reduced polyacrylamide gel. Bands were cut out, counted and the amount of bound peptide was calculated from the specific activity.

The stability of human DR2-MBP(83–102) complex at 4° C. was also investigated. Complexes of DR2 and 125I-MBP (83–102) were prepared as described above and stored at 4° C. Every week an aliquot of 1 gl was applied on a silica gel TLC plate in triplicate. Plates were run, developed and the percent dissociation was calculated. Over a period of 42 days, there was no significant dissociation of this complex.

EXAMPLE 2

EBV Transformation of B Cells from an Individual with an Autoimmune Dysfunction

Peripheral blood mononuclear cells (PBMNC) from an individual with an autoimmune dysfunction are isolated by diluting whole blood or buffy 1:1 with sterile phosphate buffered saline (PBS), pH 7.2, layering the suspension on Ficoll-Hypaque, and centrifuging 20 minutes at 1800–2000 RPM in a table top centrifuge. PBMNC present in a band at the interface of the Ficoll-Hypaque and PBS-plasma are harvested with a pipette and washed twice with PBS. Cells are resuspended at 5×10$^6$ cells/ml in RPMI 1640 containing 10% fetal serum (FBS), plated in a polystyrene flask and incubated for 1 hour at 37° C. to remove monocytes. Non-adherent cells are collected, pelleted by centrifugation and resuspended at 10×10$^6$ cells/ml in Ca$^{++}$—Mg$^{++}$ free Dulbecco's PBS containing 15% FBS. AET-SRBC (2% v/v) is mixed 1:1 with PBMC, the mixture is centrifuged for 20 min. at 100×g, and then incubated on ice for 1 hour. The pellet is gently resuspended, and the suspension centrifuged through Ficoll-Hypaque as described earlier. The band which contains B cells and remaining monocytes is harvested.

Transformation of B cells is with B95–8 cell line (Walls and Crawford in *Lymphocytes: A Practical Approach* (G. G. B. Klaus ed., IRL Press)). The B95-8 cells are diluted 1:3 in medium, and cultured for 5 days at 37° C. The supernatant is harvested, centrifuged at 250×g for 15 minutes, and filtered through a 0.45 micron millipore filter. The EBV is then concentrated by centrifugation at 10,000 rpm for 2 hours at 4° C., and the pellet containing the virus is suspended in RPMI 1640 containing 10% FBS, at 1% of the original volume.

In order to transform B cells, the virus stock is diluted 1:9 with culture medium containing 2×10$^6$ cells. After the virus is absorbed to the cells for 1–2 hours at 4° C., the cells are centrifuged at 250×g. The resulting cell pellet is suspended at approximately 0.7×10$^6$ to 7.0×10$^6$ cells/ml in RPMI 1640 containing 10% FBS. Transformed cells are cloned using standard methods.

The transformed B cells made by the procedure are suitable for the isolation of human MHC glycoproteins.

EXAMPLE 3

Induction of EAE in Mice

Adoptive transfer of T cell clones AJ1.2 and 4R3.4, as well as immunization of mice with MBP(1–13) causes mice to develop EAE.

Figure 17:
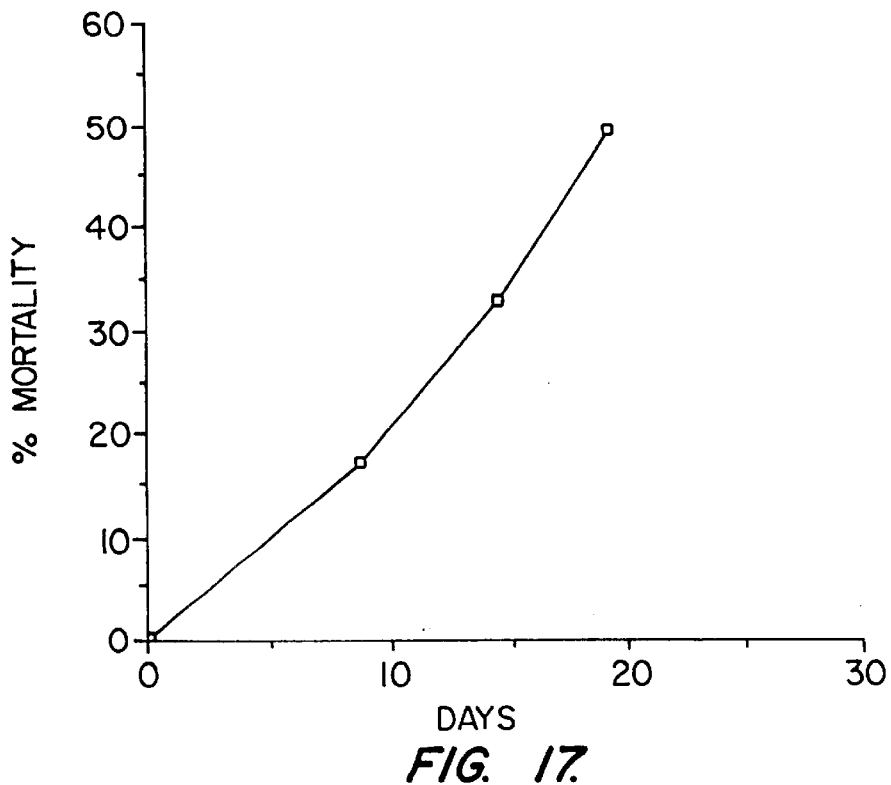
FIG. 17 is a graph showing the development of EAE in mice resulting from immunization with MBP (1–13).

EAE was induced with the peptide using the method for induction of EAE in mice with intact MBP. Briefly, MBP (1–13) was dissolved in PBS and mixed vigorously with complete Freund's adjuvant so as to form a thick emulsion. Female A/J mice were injected with 100 micrograms of this mixture at four sites on the flank. Twenty-four and 72 hours later, 400 ng of pertussis toxin was injected intravenously. Mice are observed daily by two individuals for the development of EAE and mortality. The results in FIG. 17 show the development of EAE in mice resulting from immunization with MBP(1–13).

Figure 18:
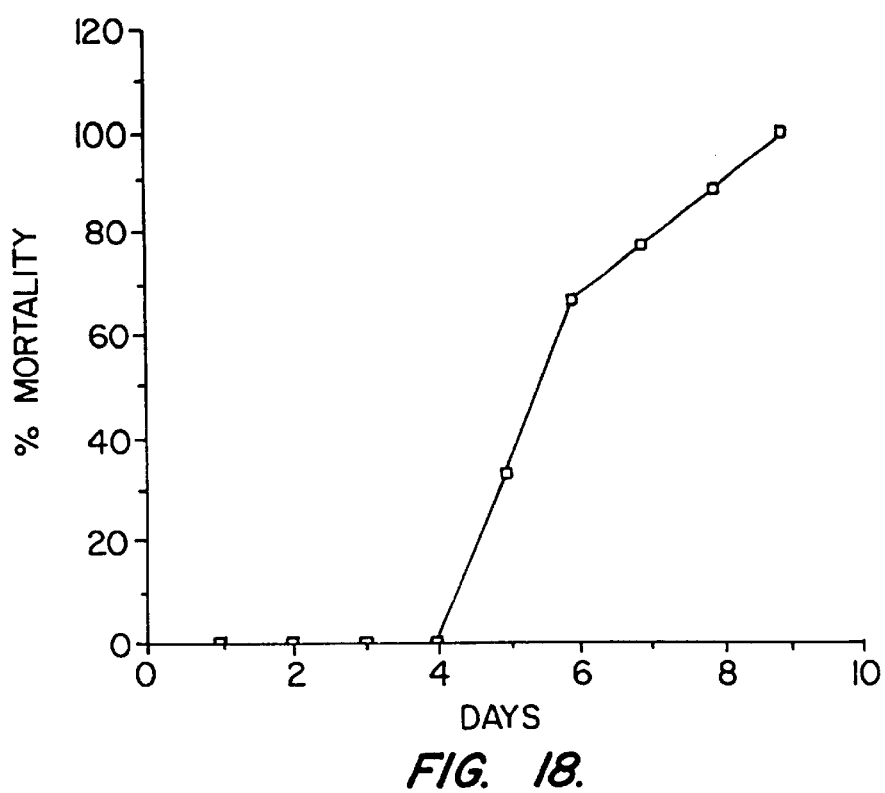
FIG. 18 is a graph showing the adoptive transfer of EAE by T cell clone 4R3.4, obtained from B10A (4R) strain of mice following immunization with MBP (1–11).

For the adoptive transfer of EAE, T cell clone 4R3.4, obtained from B10A(4R) strain of mice following immunization with MBP(1–11) was used. B10.A(4R) mice were given 350 rad of whole body radiation and then injected with 400 ng pertussis toxin intravenously. Two to three hours later 10×10$^6$ 4R3.4 cells, stimulated with MBP(1–13) three days previously, were injected intravenously. These animals were observed twice daily for signs of EAE and mortality. The results of this study are summarized in FIG. 18.

EXAMPLE 4

Down-Regulation of EAE by I-A$^s$-MBP(91–103) Complex

This example demonstrates that in vivo therapy with complexes of the present invention results in prevention of passively induced EAE. In addition, the therapy significantly lowered mortality and morbidity in treated animals.

In order to demonstrate that treatment with I-A$^s$/MBP (91–103) complex will prevent the development of EAE following T cell activation, SJL mice were injected with MBP(91–103) reactive T cell blasts in vivo. Briefly, SJL mice 10–12 weeks of age were immunized with 400 μg of MBP(91–103) (Ac-FFKNIVTPRPPP-amide (SEQ ID NO: 9), >95% purity) in complete Freund's adjuvant on the dorsum. After 10–12 days, regional draining lymph node cells were harvested and cultured in 24 well plates (Falcon) at a concentration 6×10⁶ cells/well in a 1.5 mls of RPMI 1640 media containing 10% fetal bovine serum, 1% penicillin/strepmycin and 50 μg/ml of MBP. Following a 4 day in vitro stimulation, MBP(91–103) reactive T cell blasts were harvested via ficoll-hypaque gradient (Hypaque 1077, Sigma, Mo.) and washed twice in PBS according to standard techniques. Approximately $1.3–1.5 \times 10^7$ cells were injected into each mouse.

Mice that received encephalitogenic MBP(91–103) reactive T cells then received either 100 μg of soluble I-A$^s$/MBP (91–103) complexes in 100 μl PBS, 100 μg of I-A$^s$/MBP (1–14) (a peptide that is not encephalitogenic in SJL mice) complexes in 100 μl PBS or PBS alone on days 0, 3, and 7 (total dose 300 μg). Animals were observed daily and graded for clinical signs of EAE: grade 1, loss of tail tone; grade 2, hind leg weakness; grade 3, hind leg paralysis; grade 4, moribund; grade 5, death. In accordance with the regulations of the animals care committee, mice that could not feed themselves were sacrificed.

Figure 19A:
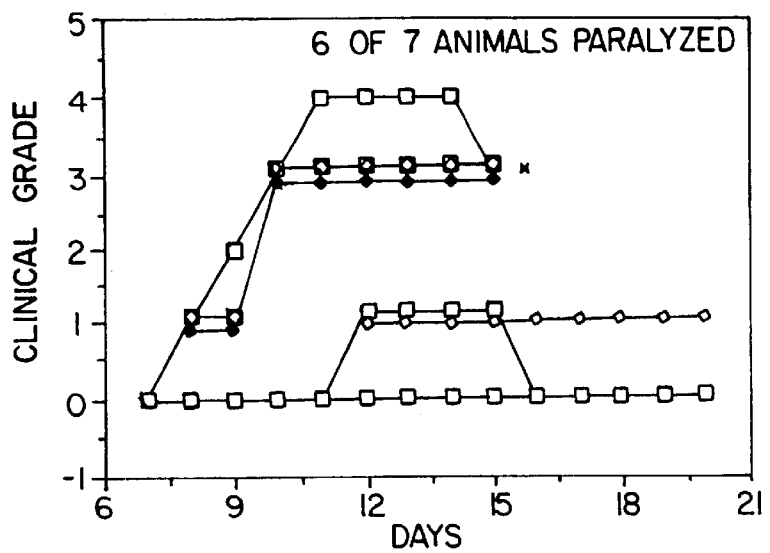
FIGS. 19A–C show treatment of passively induced EAE in mice using PBS alone (19a), I-$A^s$/MBP1–14 (a non-encephalitogenic peptide) (19b), and I-$A^s$/MBp91–103 (19c).
Figure 19B:
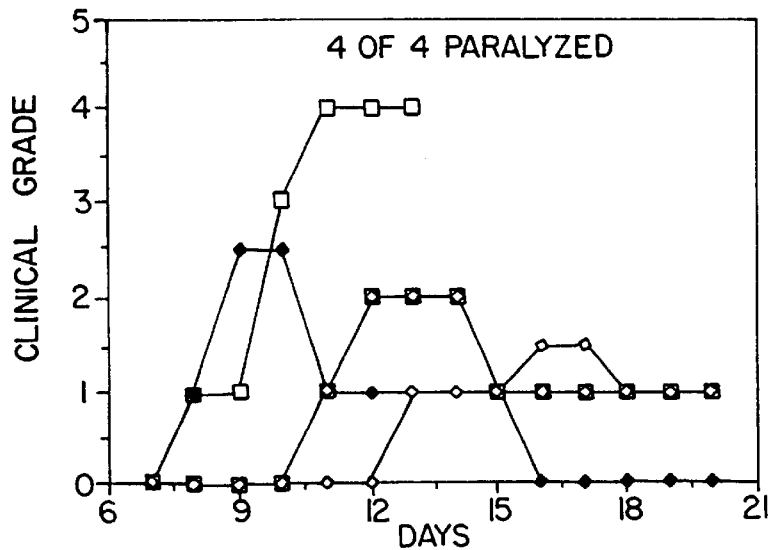
Figure 19C:
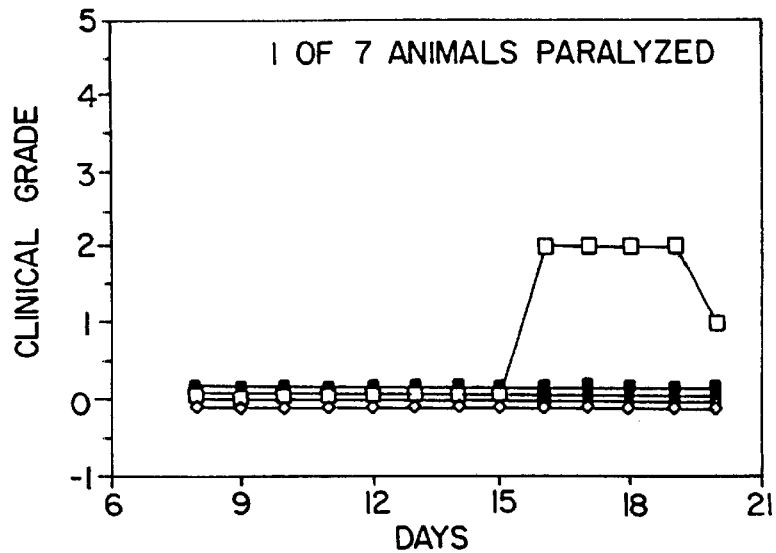

Only one of the seven mice that received I-A$^s$/MBP (91–103) complex developed clinical EAE on day 16 (FIG. 19). In contrast, all four animals that received the I-A$^s$/MBP1–14, and six of seven animals that received PBS developed paralysis. In the former group, the mean onset of disease was on days 9.7 and in the latter group it was 9.0 with mean severity of 2.3 and 2.5 respectively.

The inability of other auto-antigens presented by the I-A$^s$ allele to inhibit disease induction was also demonstrated. SJL mice were immunized with the peptide 139–151 of proteolipoprotein (PLP) in complete Freund's adjuvant to induce EAE. SJL mice were immunized with the peptide dissolved in PBS and mixed with complete Freund's adjuvant containing 4 mg/ml *Myobacterium tuberculosis* H37Ra in a 1:1 ratio. Animals were injected with 152 μg of peptide, a dose found to induce EAE in 100% of the animals, subcutaneously in both abdominal flanks. On the same day, and 48 hours later, all animals were given 400 μg of pertussis toxin intravenously. Mice were treated with PBS, 15 μg of I-A$^s$ alone or 15 μg of I-A$^s$ plus PLP(139–151) on days 1, 4, and 7 after immunization as described above.

As shown in Table 1, animals that received the appropriate I-A$^s$/PLP(139–151) peptide complex were protected from the severe fulminant paralytic disease induced by the immunization with peptide in adjuvant. The was no mortality in the I-A$^s$/PLP peptide treated group. Although all six animals did develop paralysis, the mean severity of animals that were paralyzed was 2.2 and the mean day of onset was 10.6. In contrast, all six animals that received I-A$^s$ complex alone, died with a mean day of onset of 8.2. Five animals died by day 11 and one animal died on day 21. Animals that received saline or no treatment had a mortality of 87% and the average day of onset was 9.2 (p<0.0001 I-A$^s$/PLP (139–151)

TABLE 1

| Treatment Received | No Animals Paralyzed | Mean Severity | Mortality | Day of Onset Paralysis |
|---|---|---|---|---|
| None or Saline | 15 of 15 | 4.7 | 87% | 8 |
| I-A$^s$ complex alone | 6 of 6 | 5 | 100% | 7 |

TABLE 1-continued

| Treatment Received | No Animals Paralyzed | Mean Severity | Mortality | Day of Onset Paralysis |
|---|---|---|---|---|
| I-A$^s$ PLP (139–151) | 6 of 6 | 2.2 | 0 | 10 |

Our observations indicate that in vivo therapy with I-A$^s$/MBP(91–103) complexes (300 μg) results in the prevention of passively induced EAE. In addition, therapy with 45 μg of I-A$^s$/PLP(139–151) significantly lowered the mortality and morbidity in animals that received this therapy.

The complexes of the invention were also tested for the ability to prevent relapse of EAE in mice. In these experiments, SJL mouse received $1.2 \times 10^7$ p91–103 reactive T cells ip on day zero. Initial paralytic signs developed between 8–12 days and all animals recovered by at least 2 clinical grades by day 22. The mice received 50 μgm of MHC complex (with the cognate peptide and without), or PBS iv on days 27, 37, and 47. In experiment 1 mice were observed for 102 days and in Experiment 2, they were observed for 112 days. The results indicated that the complexes with the cognate peptide were significantly more effective than controls in preventing relapses.

EXAMPLE 5

Down-regulation of RA by MHCII-HSP (180–188) Complexes

Lewis rats develop a form of arthritis called adjuvant arthritis in response to subcutaneous injections of Mycrobacterium tuberculosis emulsified in incomplete Freund's adjuvant. This model of arthritis fulfills many of the criteria necessary for evaluating efficacy of drugs being developed for the treatment of rheumatoid arthritis. The pathology of the tissue and the infiltration of monocytic and lymphocytic cells indicate a strong T cell mediated response. The experiments described here use a technique that anergizes peptide-specific-T cells that recognize and bind the peptide-MHC Class II complex. The studies involve in vivo treatment with the soluble MHC Class II-peptide complex soon after the induction of the disease. The results show significantly less bone degeneration in the MHC Class II-peptide treated rats compared to the group that received saline treatment.

Lewis rat MHC Class II RTLB and RT1D molecules were affinity purified from NP-40 extract of splenocyte membranes on OX-6 and OX-17 monoclonal antibodies coupled to sepharose 4B columns. The relative yield of RT1B to RT1D was 1:2. MHC Class II molecules were loaded with the peptide by mixing 56 μg of RT1B and 113 μg of RT1D molecules with 50-fold molar excess of the heat shock protein (HSP) peptide, p(180–188), at 37° C. for 48h in a total volume of 1 ml phosphate buffer pH 7.5 containing 1% octylglucoside. The unbound peptide was removed by extensive dialysis of the sample against PBS buffer at 4° C. The final complex concentration was 170 μg/ml and was free of endotoxin as tested by Limulus amebocyte lysate procedure as described by Whittaker Bioproduct, Inc.

Six male Lewis rats (age 77 days) were injected in both hind foot pads with 1 mg of Mycobacterium tuberculosis in incomplete Freund's adjuvant to induce arthritis. Three of the rats were treated with the MHC Class II+plus HSP180–188 complex intravenously on days 1, 4 and 7 after the induction of the disease. The other three rats were given saline as above. Arthritic index was determined by the gross appearance and by the following criteria: 0) no change; 1) slight change in the joints of the digits; 2) slight to moderate edema of the paw or swelling of more than two digits; 3) swelling of the paw with slight scabbiness, moderate curing of toes and nails; 4) severe swelling of the paw, marked scabbiness, and prominent curing of toes and nails.

The rats treated with MHC Class II-peptide or saline had swelling of most of their feet by day 20, with an arthritic index of 4. It is most likely that the differences in the swelling seen in some of the rats' feet was a reflection of the amount of MT injected. However, when radiographs of the feet were taken on day 35 after the induction of the disease, there was a significant difference between the MHC Class II-peptide treated and the saline treated groups.

In a second experiment, 18 animals were treated over 5 weeks during the course of disease progression. As illustrated in Table 2, animals treated with MHC-peptide of the present invention had a greatly reduced arthritic index and significantly reduced joint swelling compared with the saline treated group. Animals received 25 $\mu$g of MHC-peptide on days 4, 8, and 12.

TABLE 2

Reduction of inflammation and severity of disease

| Treatment | # of Rats | Thickness (mm ± SD) | Arthritic Index |
|---|---|---|---|
| Saline | 4 | 10.5 ± 0.6 | 4 ± 0 |
| MHC alone | 4 | 9.0 ± 0.7* | 3.25 ± 0.5 |
| MHC + HSP (180–188) | 5 | 7.88 ± 1.4* | 2.6 ± 0.55 |
| Normal | 5 | 5.55 ± 0.36 | 00 |

*Statistically significant compared to saline treatment (p < 0.05 by student's t-test).

On day 35, tarsal joints of all animals were measured using vernier calipers. Measurements represent the sum of the thickness of both hind feet.

EXAMPLE 6

Increasing Serum Half-life of the Complexes

This example presents data showing that various modifications of the complexes lead to increased serum half-life.

The protocol for these studies was generally as follows: Affinity-purified, soluble MHC molecules were labeled with $^{125}$I by the iodobeads method (Pierce Chemical Co., Rockford, Ill. Excess $^{125}$I was removed by dialysis against PBS containing 0.1% neutral detergent. The quality of the labeled protein was assessed by thin layer chromatography, cellulose acetate electrophoresis, and polyacrylamide gel electrophoresis. The MHC glycoprotein was administered by tail vein injection to mice subjected to Lugol's solution in the drinking water at least one day before injection. Blood samples were obtained at different time points. The animals were then sacrificed to obtain organs of interest. Radioactivity in the blood and organ samples was detected in a gamma well counter according to standard techniques.

A. Effect of Asialoletuin on Serum Half-life

IA$^k$ was labeled and administered to mice as described above. The mice were divided into three sets: (1) I-A$^k$ (10 $\mu$g i.v.); (2) I-A$^k$ (10 $\mu$g i.v.) plus asialoletuin (10 mg i.v.) plus asialoletuin (100 mg i.p.); and (3) I-A$^k$ (10 $\mu$g i.v.) plus asialoletuin (10 mg i.p.). Blood was drawn at different time points and the percent of injected dose retained in the blood was calculated.

The mean serum half-life for the three sets was as follows:

Set 1—3 min.

Set 2—40 min.

Set 3—35 min.

B. Effect of Liposomes on Serum Half-life

I-A$^s$ was labeled as described above. The labeled I-A$^s$ molecules were captured inside liposomes by standard procedures (see, e.g., Remingtion's, supra). Ten mice were injected with 10 $\mu$g I-A$^s$, as described above, and divided into four sets: (1) I-A$^s$ alone; (2) liposomal I-A$^s$; (3) liposomal I-A$^s$ coinjected with blank liposomes; and (4) blank liposomes plus, 10 minutes later, liposomal I-A$^s$ coinjected with blank liposomes. Blood samples were obtained at different time points after injection, and the percent of injected dose of I-A$^s$ retained in the blood was calculated.

The serum mean half-life of the three sets was as follows:

Set 1—2 min.

Set 2—7 min.

Set 3—10 min.

Set 4—60 min.

C. Effect of Periodate/cyanoborohydride Treatment on Serium Half-life

I-A$^k$ in a phosphate buffer containing 3 mM taurodeoxycholate at pH 7.5 was labeled as described above. The labeled molecules were subjected to periodate oxidation and cyanoborohydride reduction for 5 or 21 hours at 4° C., using 20 mM sodium periodate and 40 mM cyanoborohydride (final concentrations) in 0.1 M acetate buffer at pH 5.5. The reaction was quenched by addition of ethylene glycol (final concentration 0.7%). The treated I-A$^k$ was purified by dialysis and administered (10 $\mu$g i.v.) to mice, as described above. Nine mice were divided into three sets: (1) I-A$^k$ (untreated); (2) I-A$^k$ (5 hr. treatment); and (3) I-A$^k$ (21 hr. treatment). Blood samples were obtained at different time points and the percent of injected dose of I-A$^k$ retained in the blood was calculated.

The serum half-life of the three sets was as follows:

Set 1—4 min.

Set 2—7 min.

Set 3—70 min.

EXAMPLE 7

The results presented below demonstrate that MHC-peptide complexes of the invention exist primarily as a$\mu$gregates in the absence of detergent.

Figure 20:
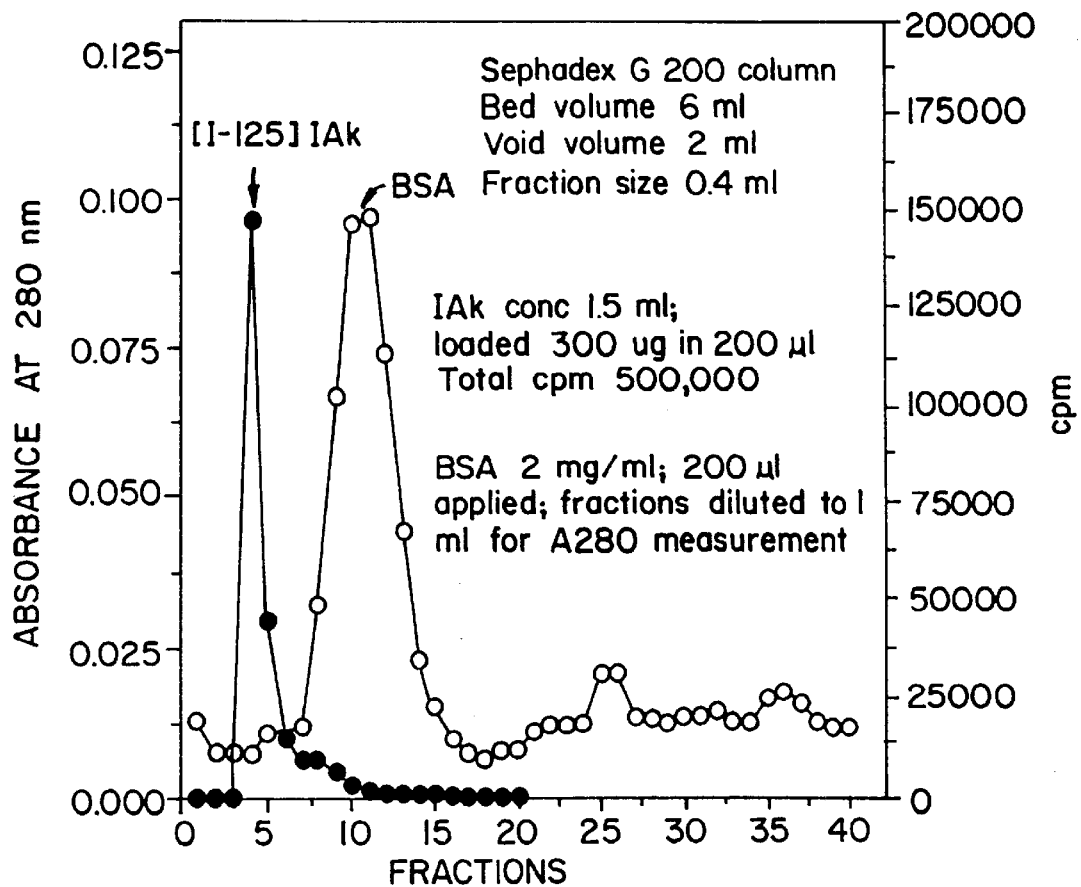
FIG. 20 shows that complexes of the invention exist as aggregates because they pass through the column with the void volume and thus have a molecular weight greater than 600,000.

An IA$^k$-P complex labeld with $^{125}$I was prepared as described above. The complex (1.5 mg/ml) was dialysed extensively against phosphate buffered saline (PBS) to remove detergent and loaded on a 6 ml b. v. Sephadex-G200 column (fractionation size 5000–600,000). The results presented in FIG. 20 show that the gregated complexes pass through the column with the void volume and thus have a molecular weight greater than 600,000.

The same dialyzed IA$^k$ complex (1.5 mg/ml) was also centrifuged and the pellet was counted. To do this, 200 $\mu$l of complex (300 $\mu$g) was diluted in 5 ml PBS and centrifuged in a fixed angle rotor at 100,000 xg for 60 minutes. The results are given in Table 3, below.

TABLE 3

DETECTION OF COMPLEX AGGREGATION BY HIGH SPEED SPIN

| EXP # | Starting cpm | cpm in pellet | cpm in sup | % aggreg. |
|---|---|---|---|---|
| 1 | 514,576 | 317,717 | 205,797 | 60.68 |
| 2 | 519,340 | 321,304 | 209,108 | 60.57 |

The results of the chromatography and centrifugation experiments both show that MHC-peptide complexes exist largely in gregated or micellar form. These results strongly indicate that the single subunit complexes of the present invention are also aµgregated or in micellar form, in the absence of detergent.

EXAMPLE 8

This example demonstrates that administration of soluble MHC class II-AChR α peptide 100–116 complexes alter the function of AChR-reactive T cells and thereby modulate the course of EAMG, an antibody mediated, but T cell dependent autoimmune disease.

AchR and AchR Peptides. Electroplax tissue from Torpedo californica (Pacific Biomarine) was homogenized and the membrane fraction was detergent solubilized (2% Triton X-100, 100 mM NaCl, 10 mM MOPS, 0.1 mM EDTA, 0.02% NaN$_3$). AChR was isolated from the solubilized membranes by affinity chromatography with the anti-AChR monoclonal antibody mAb 35 and dialized against 1.0% n-octyl β-D-glucopyranoside (OG)/PBS.

Torpedo AChRα subunit peptide 100–116 (YAIVHMTKLLLDYPGKI (SEQ ID NO: 10) was synthesized by solid-phase 9-fluorenylmethoxycarbonyl (FMOC) procedures, using standard procedures. The peptides were purified by reverse-phase HPLC, and characterized by HPLC and mass spectroscopy.

Rat MHC II Purification and Peptide Loading. Rat class II RT1.B and RT1.D molecules were detergent solubilized (0.5% NP-40, 10 mM Tris HCl pH 8.3, 1 mM PMSF, 0.02% NaN$_3$) from homogenized spleens and purified by affinity chromatography with monoclonal antibodies OX 6 and OX 7. The RT1.B/D mixture was incubated at 37° C. for 24 hours with a 50-fold molar excess of peptide AChRα 100–116, followed by 24 hours of dialysis at 4° C. against 0.1% OG/PBS to remove unbound peptide. Analysis by nitrocellulose filter binding and TLC (B. Nag et al. (1991) *J. Immunol. Meth.* 142: 105) revealed 70–80% of the RT1.B and 90–100% of the RT1.D bound peptide AChRα 100–116. This complex is stable at 4° C. for at least 8 weeks.

Induction of EAMG and Treatment with Soluble MHC II:AChRα 100–116. Male Lewis rats (8–12 weeks old) were injected in both hind footpads with Tc AchR emulsified in complete Freund's adjuvant, and intraperitoneally with 600 ng of Pertussis toxin. Sick rats (clinical stage 1–3) were fed moist chow and teeth were trimmed weekly.

On days 1, 4, and 7 post AChR immunization, individual rats were treated i.v. with saline, 25 µg MHC II alone (MHC II:0), or 25 µg of MHC II complexed with the T.c. AchRα peptide 100–116 (MHC II:AchRα 100–116). T cells were purified from popliteal lymph nodes 9 days after AchR immunization and tested for proliferation to a panel of antigens.

T Cell Proliferation Assay. T cells from the peripheral lymph nodes were isolated by nylon wool chromatography. 2×10$^5$ T cells and 3×10$^5$ irradiated syngeneic splenocytes were incubated in 0.2 ml of culture medium (RPMI 1640, 10% FBS, 10 mM HEPES, 5×10$^5$ M 2-ME, 100 U/m. penicillin, 100 U/ml streptomycin) with peptide or whole antigen for 3 days at 37° C., 5% CO$_2$, pulsed with 1 µCi $^3$H-thymidine for 18 hours, harvested, and counted.

Timecourse of EAMG in Lewis Rats. Immunization of Lewis rats with T. c. AchR induces anti-AchR antibodies, causing weight loss and progressive muscle weakness with a predictable timecourse. A drop in weight in the week following immunization coincides with an "acute phase" due to infiltration of the neuromuscular junction by mononuclear cells. A second, sustained weight loss begins at day 33–40, a "chronic phase" accompanied by the clinical symptoms resembling MG in human patients. Weight changes of individual rats are shown to demonstrate the range of disease onset, progression, and time of death (indicated by intersection with the abscissa).

In untreated rats, progressive EAMG may be classified into three stages. In stage 1, anti-AChR antibodies cause endocytosis of the AchR. Subthreshold levels of AChR at the neuromuscular junction reduce muscle contractions, particularly in the posterior muscles. Weak back and hind leg muscles cause a characteristic hunched posture at rest. Stage 2 is characterized by progressive weakness that causes frequent rest periods, with the head unsupported due to weakness in the neck muscles. In stage 3, the diaphragm and intercostal muscles are weakened, causing labored breathing. Deterioration of the mandible muscles leads to excessive tooth growth.

To test the therapeutic effect of soluble MHC I:AChRα 100–116, rats were treated after clinical symptoms appeared in the chronic phase.

Antigen-Specific Unresponsiveness Induced by Soluble MHC II:AChRα 100–116. In saline treated rats, the T cell response to AChRα peptide 100–116 equalled 30% of the response to AChR ($\alpha^2\beta\gamma\delta$) (FIG. 21), confirming literature reports that 100–116 is a major epitope in the T cell response to AChR. T cells from the MHC:0 treated rat respond to each antigen at levels similar to T cells from the saline treated rat.

Figure 21:
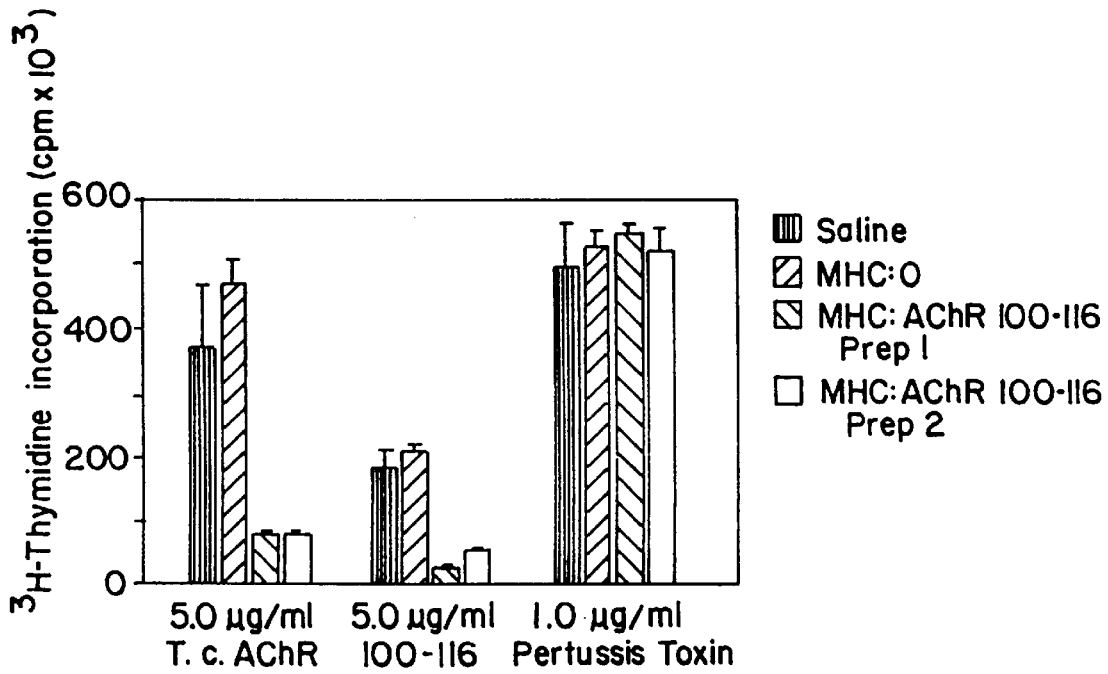
FIG. 21 shows that complexes of the invention (MHC II:AChRα 100–116) were effective in treating MG in rats.

The T cell response of MHC II:AChRα 100–116 treated rats to whole Tc AChR and AChRα 100–116 were respectively 22% and 20% of saline treated rat T cell proliferation levels (FIG. 21). Proliferation of T cells from the MHC II:AChRα 100–116 treated rat to Pertussis toxin was equivalent to T cells from saline and MHC II:0 treated rats, indicating that the T cell inactivation was antigen specific (FIG. 21).

Therapeutic Effect of Soluble MHC II:AChRα 100–116. Randomized groups of rats with clinical stage 1 EAMG (approximately day 42–56 post-inoculation) were injected i.v. at five weekly intervals with saline, 25 µg MHC II:HSP 180–188 (MHC II bearing an irrelevant heat shock peptide), 25 µg MHC II alone (MHC II:0), or 5 µg AChRα 100–116 alone (O:AChRα 100–116). The weight and clinical symptoms were monitored.

Treatment of rats with clinical stage 1 EAMG with MHC II:AChRα 100–116 resulted in a survival frequency of 67% at 140 days post-induction. In comparison, the maximum survival rate in the control groups was 20% (16.7% saline, 0% Tc AChRα 100–116 alone, 20% MHC II alone, 20% MHC II:HSP 180–188). The time course of EAMG for representative rats in each treatment group is presented in Table 4.

The four surviving MHC II:AChRα 100–116 treated rats exhibited relatively severe EAMG (maxima of 2.0, 2.5, 2.5, and 3.0), followed by remission approximately three weeks after the first therapeutic injection.

TABLE 4

| TREATMENT | DAYS POST EAMG INDUCTION | | |
|---|---|---|---|
| | 61 | 123 | 224 |
| MHC II:AChRα 100–116 | 2.5 | 0.0 | 0.0 |
| MHC II:HSP 180–188 | 3.0 | 3.0 | Dead (day 138) |
| MHC II:0 | 3.0 | Dead (day 66) | |
| 0:AChR 100–116 | 2.5 | Dead (day 66) | |
| Saline | 3.0 | Dead (day 82) | |

Representative rats from each treatment group are shown 61, 123, and 224 days after EAMG induction by AChR immunization.

The clinical stage of each rat is indicated. By day 123, the MHC II:AChRα 100–116 treated rat shows improved mobility and posture, in contrast to the lone surviving rat treated with MHC:HSP 180–188.

These results show that soluble MHC II:AChRα 100–116 complex injected at the start of EAMG induction significantly reduces the T cell response to the AChRα peptide 100–116 and to whole AChR. The effect of the soluble MHC II:AChRα 100–116 complex is antigen-specific, as the complex does not affect the T cell response to an unrelated antigen, pertussis toxin. Treatment with the soluble MHC II:AChRα 100–116 complex during the chronic phase of EAMG reduces mortality and clinical symptoms of the disease.

EXAMPLE 9

This example demonstrates the ability of complexes of the invention to induce anergy in human T cells associated with myasthenia gravis (MG).

The T cells in this experiment were derived form the thymus of young onset MG patient. They recognize the residues 138–167 AChR αsubunit and are restricted by DR4Dw4. In the experiments, $2 \times 10^4$ T cells were preincubated for varying times with either complex (DR4:p138–167), DR4 alone, or peptide alone. Antigen presenting cells (APC's) pulsed with different antigens were then added and proliferation of the T cells was measured using tritiated thymidine as described above. The stimulating antigens included p138–167 and a recombinantly produced AChR αsubunit polypeptide termed r37–181, which was prepared as described in Beeson et al., *EMBO J* 9:2101–2106 (1990) and Beeson et al., *Biochem. Soc. Trans.* 17:219–220 (1989), both of which are incorporated herein by reference.

Preincubation of the T cells with complex at 10 μgm/ml overnight lead to nonresponsiveness in the T cells when subsequently presented with antigen. Incubation with lower concentrations and for shorter times were not as effective at inducing anergy.

Figure 22A:
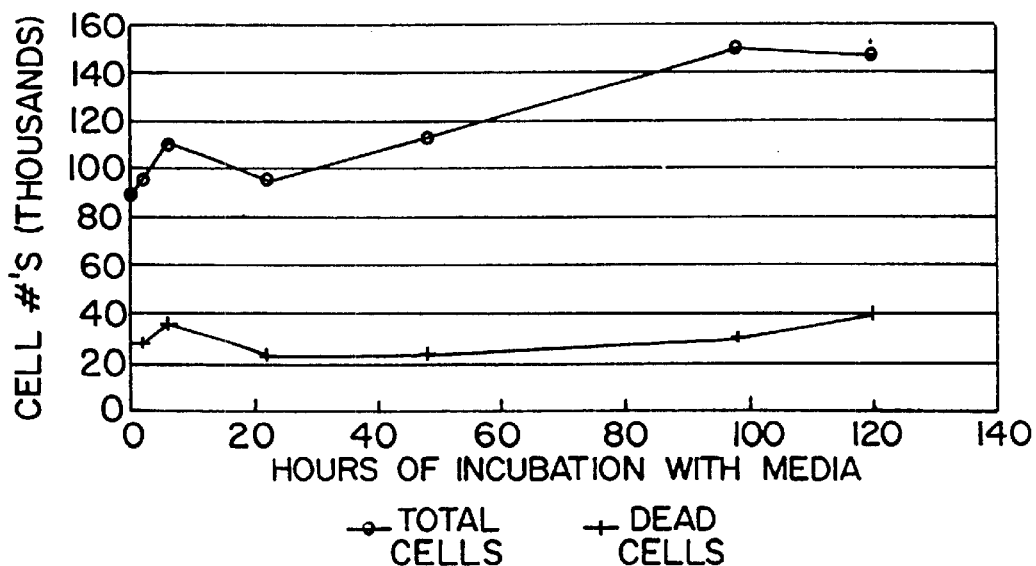
FIGS. 22A and 22B show that cell death follows the induction of anergy in T cells.
Figure 22B:
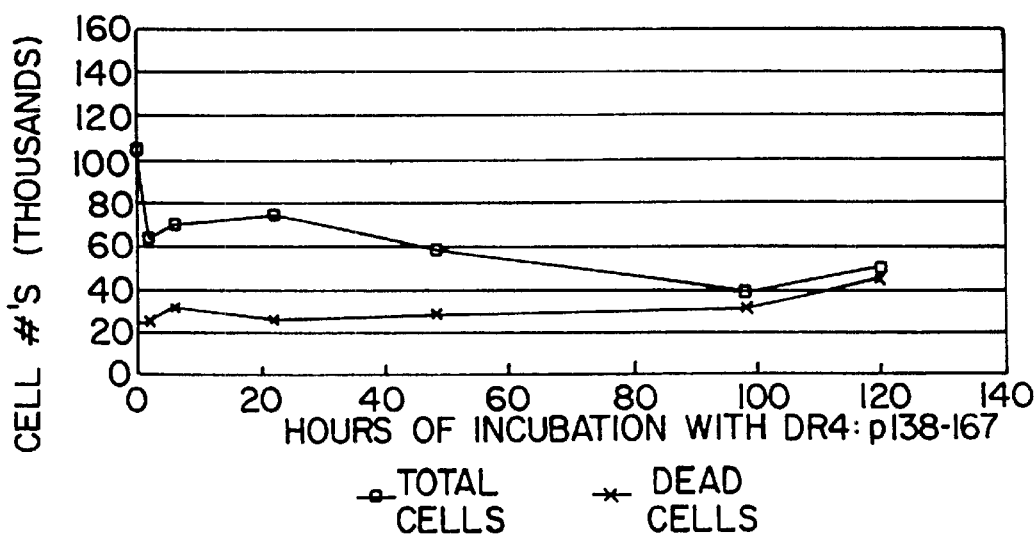

Viability of the anergized cells was tested with Trypan Blue. T-cells were incubated with media, or complex at 5 μg/ml, and aliquots withdrawn for counting at various times. Cells were counted as either living or dead based on trypan blue exclusion in living cells. The results are presented in FIGS. 22A and 22B. In the media incubated cells, the total number of cells gradually rose while the number of dead cells remained the same. In the complex incubated cells, the total number of cells fell—rapidly during the first 6 hours and more slowly thereafter. The number of dead cells gradually rose so that after several days incubation, almost 90% of the cells were dead. These results show that cell death follows the induction of anergy in T cells.

To test the specificity of the interaction of the complexes with the T cells, T-cells ($1 \times 10^4$) were incubated with various forms of the complex. These were—the relevant complex DR4:p138–167, DR4 alone, soluble DR4 and "sham" p138–167 in equimolar (proportionally) amounts but not bound together and DR4:MBPp1–14 complex. Sham peptide was used as previous experiments had shown that soluble p138–167 alone had similar effects to the complex. Sham p138–167 was a sample of p138–167 subjected to the same preparation as the complex including dialysis, thus controlling for the effects of any soluble peptide which may be released from the complex. After overnight preincubation, irradiated PBL's ($2 \times 10^5$) and stimulating antigens were added.

Irrelevant complexes and peptides did not induce anergy. Incubation overnight with media and subsequent stimulation with recα37–1811 resulted in a good proliferative response. Preincubation with DR4:p13B-167 substantially reduced subsequent proliferation. However, preincubation with any of the other substances had no effect on proliferation compared to preincubation with media.

In addition to the effects of preincubating with various complexes, the effect of adding various antibodies to cell surface markers, or of adding IL2 0.5%, at the time of preincubation with DR4:p138–167 was studied. Addition of an anti-TCR Ab (anti-TAC—786) inhibited the background stimulation caused by the complex, inhibited any antigen-induced response and partially inhibited the response to stimulation with IL2 after preincubation. An anti-DR Ab (L234) had no effects on the inhibition of antigen induced response induced by preincubation with complex. Combination of anti-TAC and anti-DR reduced background proliferation and antigen-induced proliferation but had no effect on IL2-induced proliferation. Preincubation of the T-cells with complex in the presence of 0.5% IL2 did not diminish the inhibitory effects of the complex. similarly, experiments designed to identify any non-specific effects of the complex on non-DR4, non-AChR T cell lines. Cells ($2 \times 10^4$) from lines raised against KLH or Tetanus Toxoid were preincubated overnight with the complex. They were then stimulated in the with irradiated PBL's ($2 \times 10^5$) and antigen. Preincubation with the complex did not have any effect on background proliferation response to specific antigen. Thus the complex does not appear to have any non-specific stimulatory or inhibitory effects on unrelated cell lines.

Figure 23A:
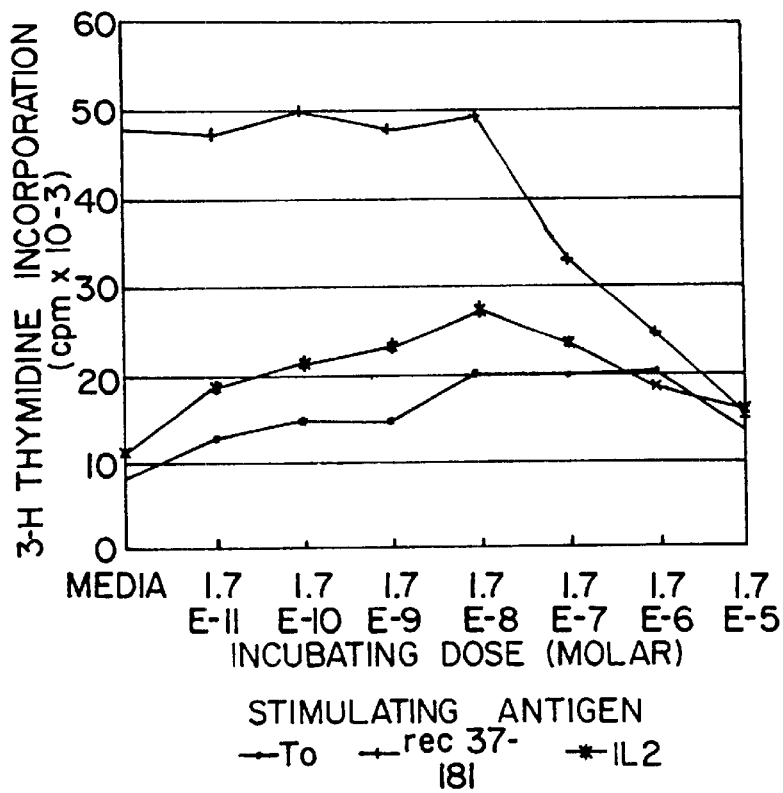
FIGS. 23A and 23B show that the molar concentration of complex of the invention required to induce anergy is much less than that of peptide alone.
Figure 23B:
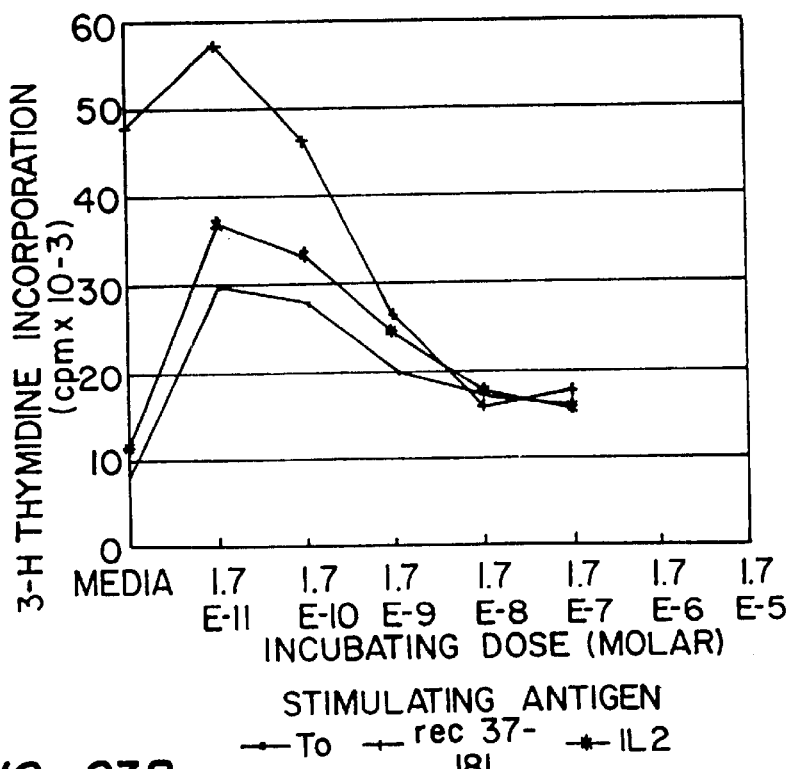

Finally, FIGS. 23A and 23B show that the molar concentration of complex required to induce anergy is much less than that of peptide alone. As can be seen form the figures, preincubation of T-cells with p138–167 at concentrations above $1.7 \times 10^8$ resulted in a decrease in the response to recombinant. Preincubation with lower concentrations caused an increase in background proliferation compared to preincubation with media (far left). Not until concentrations of $1.7 \times 10^{-5}$ were reached did the proliferative response fall to background levels.

Preincubation of T-cells with DR4:p138–167 at concentrations greater than $1.7 \times 10^{-11}$ inhibited the antigen-induced proliferative response. At concentrations above $1.7 \times 10^{-8}$ the antigen-induced proliferation fell to background levels. The lowest concentration of the complex used, $1.7 \times 10^{-11}$, resulted in an increase in antigen-induced proliferation, an increase in background proliferation and an increase in the proliferative response to IL2.

Thus, both complex and p138–167 alone cause some stimulation. At higher concentrations, both inhibit antigen-specific response. However, the amount of p138–167 required for comparable inhibition (i.e. to levels of background stimulation) was approximately 1000× (molar) that of DR4:p138–167.

The results described in the Examples, above, demonstrate the ability of the complexes of the present invention to treat autoimmune disease in vivo. These data in combination with the in vitro data showing induction of anergy establish the effectiveness of the claimed complexes. Although the invention has been described in some detail in these examples for purposes of clarity and understanding, it will be apparent that certain changes and modifications may be practiced within the scope of the appended claims.

---

What is claimed is:

1. An MHC class II peptide complex capable of inducing nonresponsiveness in a target T cell, the complex comprising a preselected antigenic peptide bound to an isolated recombinant MHC class II heterodimer, the recombinant MHC class II heterodimer comprising a recombinant alpha chain and a recombinant beta chain and having an antigen binding pocket, wherein the antigenic peptide is associated with the antigen binding pocket and is recognized by the target T cell.

2. The complex of claim 1, wherein the recombinant MHC class II components are isolated from a prokaryotic cell.

3. The complex of claim 1, wherein the recombinant MHC class II components are isolated from a eukaryotic cell.

4. The complex of claim 1, wherein the recombinant MHC class II components are isolated from a yeast cell.

5. The complex of claim 1, wherein the antigenic peptide comprises an epitope recognized by a T cell specifically immunoreactive with an autoantigen.

6. The complex of claim 5, wherein the autoantigen is selected from the group consisting of myelin basic protein, acetyl choline receptor, and type II collagen.

7. The complex of claim 6, wherein the antigenic peptide is from myelin basic protein.

8. The complex of claim 1, wherein the antigenic peptide consists of between about 8 amino acids and about 15 amino acids.

9. The complex of claim 1, wherein the antigenic peptide consists of 20 amino acids.

10. The complex of claim 1, wherein the recombinant MHC II component is DR2.

* * * * *

```
                        SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
        (A) LENGTH: 1350 base pairs
        (B) TYPE: nucleic acid
        (C) STRANDEDNESS: single
        (D) TOPOLOGY: linear (ii) MOLECULE TYPE: mRNA (ix) FEATURE:
        (A) NAME/KEY: CDS
        (B) LOCATION: 1..1350
        (D) OTHER INFORMATION: /product= "acetylcholine receptor
            alpha subunit"

(xi) SEQUENCE DESCRIPTION: SEQ ID NO:1:

CUA CUG UUA UUU UCG UGU UGU GGU CUG GUA CUA GGU UCU GAA CAU GAA        48
Leu Leu Leu Phe Ser Cys Cys Gly Leu Val Leu Gly Ser Glu His Glu
  1               5                  10                  15

AGA CGU UUG GUU GCU AAU UUA UUA GAA AAU UAU AAC AAG GUG AUU CGU        96
Arg Arg Leu Val Ala Asn Leu Leu Glu Asn Tyr Asn Lys Val Ile Arg
             20                  25                  30

CCA GUG GAG CAU CAC ACC CAC UUU GUA GAU AUU ACA GUG GGG CUA CAG       144
Pro Val Glu His His Thr His Phe Val Asp Ile Thr Val Gly Leu Gln
         35                  40                  45

CUG AUA CAA CUC AUC AGU GUG GAU GAA GUA AAU CAA AUU GUG GAA ACA       192
Leu Ile Gln Leu Ile Ser Val Asp Glu Val Asn Gln Ile Val Glu Thr
     50                  55                  60

AAU GUG CGC CUA AGG CAG CAA UGG AUU GAU GUG AGG CUU CGC UGG AAU       240
Asn Val Arg Leu Arg Gln Gln Trp Ile Asp Val Arg Leu Arg Trp Asn
 65                  70                  75                  80

CCA GCC GAU UAU GGU GGA AUU AAA AAG AUC AGA CUG CCU UCU GAU GAU       288
Pro Ala Asp Tyr Gly Gly Ile Lys Lys Ile Arg Leu Pro Ser Asp Asp
                 85                  90                  95

GUU UGG CUG CCA GAU UUA GUU CUG UAC AAG AAU GCU GAU GGU GAU UUU       336
Val Trp Leu Pro Asp Leu Val Leu Tyr Lys Asn Ala Asp Gly Asp Phe
            100                 105                 110

GCC AUU GUU CAC AUG ACC AAA CUG CUU UUG GAU UAU ACG GGA AAA AUA       384
Ala Ile Val His Met Thr Lys Leu Leu Leu Asp Tyr Thr Gly Lys Ile
        115                 120                 125

AUG UGG ACA CCU CCA GCA AUC UUC AAA AGC UAU UGU GAA AUU AUU GUA       432
Met Trp Thr Pro Pro Ala Ile Phe Lys Ser Tyr Cys Glu Ile Ile Val
    130                 135                 140

ACA CAU UUC CCA UUU GAU CAA CAA AAU UGC ACU AUG AAG UUG GGA AUC       480
Thr His Phe Pro Phe Asp Gln Gln Asn Cys Thr Met Lys Leu Gly Ile
145                 150                 155                 160

UGG ACG UAC GAU GGG ACA AAA GUU UCC AUA UCC CCG GAA AGU GAC CGU       528
Trp Thr Tyr Asp Gly Thr Lys Val Ser Ile Ser Pro Glu Ser Asp Arg
                165                 170                 175

CCG GAU CUG AGU ACA UUU AUG GAA AGU GGA GAG UGG GUA AUG AAA GAU       576
Pro Asp Leu Ser Thr Phe Met Glu Ser Gly Glu Trp Val Met Lys Asp
            180                 185                 190
```

```
UAU CGU GGA UGG AAG CAC UGG GUG UAU UAU ACC UGC UGU CCU GAC ACU      624
Tyr Arg Gly Trp Lys His Trp Val Tyr Tyr Thr Cys Cys Pro Asp Thr
        195                 200                 205

CCU UAC CUG GAU AUC ACC UAC CAU UUU AUC AUG CAG CGU AUU CCU CUU      672
Pro Tyr Leu Asp Ile Thr Tyr His Phe Ile Met Gln Arg Ile Pro Leu
    210                 215                 220

UAU UUU GUU GUG AAU GUC AUC AUU CCU UGU CUG CUU UUU UCA UUU UUA      720
Tyr Phe Val Val Asn Val Ile Ile Pro Cys Leu Leu Phe Ser Phe Leu
225                 230                 235                 240

ACU GGA UUA GUA UUU UAC UUA CCA ACU GAU UCA GGU GAG AAG AUG ACU      768
Thr Gly Leu Val Phe Tyr Leu Pro Thr Asp Ser Gly Glu Lys Met Thr
                245                 250                 255

UUG AGU AUU UCC GUU UUG CUG UCU CUG ACU GUG UUC CUU CUG GUU AUU      816
Leu Ser Ile Ser Val Leu Leu Ser Leu Thr Val Phe Leu Leu Val Ile
            260                 265                 270

GUU GAG CUG AUC CCC UCA ACU UCC AGC GCU GUG CCU UUG AUU GGC AAA      864
Val Glu Leu Ile Pro Ser Thr Ser Ser Ala Val Pro Leu Ile Gly Lys
        275                 280                 285

UAC AUG CUU UUU ACA AUG AUU UUU GUC AUC AGU UCA AUC AUC AUU ACU      912
Tyr Met Leu Phe Thr Met Ile Phe Val Ile Ser Ser Ile Ile Ile Thr
    290                 295                 300

GUU GUU GUA AUU AAU ACU CAC CAU CGC UCU CCA AGU ACA CAU ACA AUG      960
Val Val Val Ile Asn Thr His His Arg Ser Pro Ser Thr His Thr Met
305                 310                 315                 320

CCA CAA UGG GUA CGA AAG AUC UUU AUU GAU ACU AUA CCC AAU GUU AUG     1008
Pro Gln Trp Val Arg Lys Ile Phe Ile Asp Thr Ile Pro Asn Val Met
                325                 330                 335

UUU UUC UCA ACA AUG AAA CGA GCU UCU AAG GAA AAG CAA GAA AAU AAG     1056
Phe Phe Ser Thr Met Lys Arg Ala Ser Lys Glu Lys Gln Glu Asn Lys
            340                 345                 350

AUA UUU GCU GAU GAC AUU GAU AUC UCU GAC AUU UCU GGA AAG CAA GUG     1104
Ile Phe Ala Asp Asp Ile Asp Ile Ser Asp Ile Ser Gly Lys Gln Val
        355                 360                 365

ACA GGA GAA GUA AUU UUU CAA ACA CCU CUC AUU AAA AAU CCA GAU GUC     1152
Thr Gly Glu Val Ile Phe Gln Thr Pro Leu Ile Lys Asn Pro Asp Val
    370                 375                 380

AAA AGU GCU AUU GAG GGA GUC AAA UAU AUU GCA GAG CAC AUG AAG UCU     1200
Lys Ser Ala Ile Glu Gly Val Lys Tyr Ile Ala Glu His Met Lys Ser
385                 390                 395                 400

GAU GAG GAA UCA AGC AAU GCU GCA GAG GAA UGG AAA UAU GUU GCA AUG     1248
Asp Glu Glu Ser Ser Asn Ala Ala Glu Glu Trp Lys Tyr Val Ala Met
                405                 410                 415

GUG AUU GAU CAC AUU CUG CUG UGU GUC UUC AUG CUG AUU UGU AUA AUU     1296
Val Ile Asp His Ile Leu Leu Cys Val Phe Met Leu Ile Cys Ile Ile
            420                 425                 430

GGU ACA GUU AGC GUG UUU GCU GGC CGU CUC AUU GAA CUC AGU CAA GAG     1344
Gly Thr Val Ser Val Phe Ala Gly Arg Leu Ile Glu Leu Ser Gln Glu
        435                 440                 445

GGC UAA                                                             1350
Gly (2) INFORMATION FOR SEQ ID NO:2:

(i) SEQUENCE CHARACTERISTICS:
        (A) LENGTH: 449 amino acids
        (B) TYPE: amino acid
        (D) TOPOLOGY: linear (ii) MOLECULE TYPE: protein (xi) SEQUENCE DESCRIPTION: SEQ ID NO:2:
```

-continued

```
Leu Leu Leu Phe Ser Cys Cys Gly Leu Val Gly Ser Glu His Glu
  1               5                  10                  15

Arg Arg Leu Val Ala Asn Leu Leu Glu Asn Tyr Asn Lys Val Ile Arg
             20                  25                  30

Pro Val Glu His His Thr His Phe Val Asp Ile Thr Val Gly Leu Gln
             35                  40                  45

Leu Ile Gln Leu Ile Ser Val Asp Glu Val Asn Gln Ile Val Glu Thr
     50                  55                  60

Asn Val Arg Leu Arg Gln Gln Trp Ile Asp Val Arg Leu Arg Trp Asn
 65              70                  75                  80

Pro Ala Asp Tyr Gly Gly Ile Lys Lys Ile Arg Leu Pro Ser Asp Asp
                 85                  90                  95

Val Trp Leu Pro Asp Leu Val Leu Tyr Lys Asn Ala Asp Gly Asp Phe
            100                 105                 110

Ala Ile Val His Met Thr Lys Leu Leu Leu Asp Tyr Thr Gly Lys Ile
            115                 120                 125

Met Trp Thr Pro Pro Ala Ile Phe Lys Ser Tyr Cys Glu Ile Ile Val
        130                 135                 140

Thr His Phe Pro Phe Asp Gln Gln Asn Cys Thr Met Lys Leu Gly Ile
145                 150                 155                 160

Trp Thr Tyr Asp Gly Thr Lys Val Ser Ile Ser Pro Glu Ser Asp Arg
                165                 170                 175

Pro Asp Leu Ser Thr Phe Met Glu Ser Gly Glu Trp Val Met Lys Asp
            180                 185                 190

Tyr Arg Gly Trp Lys His Trp Val Tyr Tyr Thr Cys Cys Pro Asp Thr
        195                 200                 205

Pro Tyr Leu Asp Ile Thr Tyr His Phe Ile Met Gln Arg Ile Pro Leu
    210                 215                 220

Tyr Phe Val Val Asn Val Ile Pro Cys Leu Leu Phe Ser Phe Leu
225                 230                 235                 240

Thr Gly Leu Val Phe Tyr Leu Pro Thr Asp Ser Gly Glu Lys Met Thr
                245                 250                 255

Leu Ser Ile Ser Val Leu Leu Ser Leu Thr Val Phe Leu Leu Val Ile
            260                 265                 270

Val Glu Leu Ile Pro Ser Thr Ser Ser Ala Val Pro Leu Ile Gly Lys
        275                 280                 285

Tyr Met Leu Phe Thr Met Ile Phe Val Ile Ser Ser Ile Ile Ile Thr
    290                 295                 300

Val Val Val Ile Asn Thr His His Arg Ser Pro Ser Thr His Thr Met
305                 310                 315                 320

Pro Gln Trp Val Arg Lys Ile Phe Ile Asp Thr Ile Pro Asn Val Met
                325                 330                 335

Phe Phe Ser Thr Met Lys Arg Ala Ser Lys Glu Lys Gln Glu Asn Lys
            340                 345                 350

Ile Phe Ala Asp Asp Ile Asp Ile Ser Asp Ile Ser Gly Lys Gln Val
        355                 360                 365

Thr Gly Glu Val Ile Phe Gln Thr Pro Leu Ile Lys Asn Pro Asp Val
    370                 375                 380

Lys Ser Ala Ile Glu Gly Val Lys Tyr Ile Ala Glu His Met Lys Ser
385                 390                 395                 400

Asp Glu Glu Ser Ser Asn Ala Ala Glu Glu Trp Lys Tyr Val Ala Met
                405                 410                 415

Val Ile Asp His Ile Leu Leu Cys Val Phe Met Leu Ile Cys Ile Ile
```

```
                   420              425              430
Gly Thr Val Ser Val Phe Ala Gly Arg Leu Ile Glu Leu Ser Gln Glu
               435              440              445
Gly
```

(2) INFORMATION FOR SEQ ID NO:3:

(i) SEQUENCE CHARACTERISTICS:
        (A) LENGTH: 170 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..170
        (D) OTHER INFORMATION: /note= "myelin basic protein (MBP)"

(ix) FEATURE:
        (A) NAME/KEY: Modified-site
        (B) LOCATION: 1
        (D) OTHER INFORMATION: /product= "OTHER"
           /note= "Xaa = N-acetyl-alanine"

(ix) FEATURE:
        (A) NAME/KEY: Modified-site
        (B) LOCATION: 3
        (D) OTHER INFORMATION: /product= "OTHER"
           /note= "Ala at position 3 may be present
           or absent"

(ix) FEATURE:
        (A) NAME/KEY: Modified-site
        (B) LOCATION: 10
        (D) OTHER INFORMATION: /product= "OTHER"
           /note= "Xaa = Arg or His"

(ix) FEATURE:
        (A) NAME/KEY: Modified-site
        (B) LOCATION: 11
        (D) OTHER INFORMATION: /product= "OTHER"
           /note= "Xaa = Ser or Gly"

(ix) FEATURE:
        (A) NAME/KEY: Modified-site
        (B) LOCATION: 16
        (D) OTHER INFORMATION: /product= "OTHER"
           /note= "Xaa = Ser or Thr"

(ix) FEATURE:
        (A) NAME/KEY: Modified-site
        (B) LOCATION: 40
        (D) OTHER INFORMATION: /product= "OTHER"
           /note= "Xaa = Leu or Ile"

(ix) FEATURE:
        (A) NAME/KEY: Modified-site
        (B) LOCATION: 46
        (D) OTHER INFORMATION: /product= "OTHER"
           /note= "Xaa = Ser or Gly"

(ix) FEATURE:
        (A) NAME/KEY: Modified-site
        (B) LOCATION: 59
        (D) OTHER INFORMATION: /product= "OTHER"
           /note= "Xaa = Gly or Ser"

(ix) FEATURE:
        (A) NAME/KEY: Modified-site
        (B) LOCATION: 66
        (D) OTHER INFORMATION: /product= "OTHER"
           /note= "Xaa = Thr or Ala"

(ix) FEATURE:

(A) NAME/KEY: Modified-site
        (B) LOCATION: 75
        (D) OTHER INFORMATION: /product= "OTHER"
            /note= "Xaa = Ala or Ser"

(ix) FEATURE:
        (A) NAME/KEY: Modified-site
        (B) LOCATION: 76
        (D) OTHER INFORMATION: /product= "OTHER"
            /note= "Gln at position 76 may be
            present or absent"

(ix) FEATURE:
        (A) NAME/KEY: Modified-site
        (B) LOCATION: 80
        (D) OTHER INFORMATION: /product= "OTHER"
            /note= "Xaa = Pro or Thr"

(ix) FEATURE:
        (A) NAME/KEY: Modified-site
        (B) LOCATION: 107
        (D) OTHER INFORMATION: /product= "OTHER"
            /note= "Xaa = Arg or Met"

(ix) FEATURE:
        (A) NAME/KEY: Modified-site
        (B) LOCATION: 122
        (D) OTHER INFORMATION: /product= "OTHER"
            /note= "Xaa = Lys or Arg"

(ix) FEATURE:
        (A) NAME/KEY: Modified-site
        (B) LOCATION: 141
        (D) OTHER INFORMATION: /product= "OTHER"
            /note= "Xaa = Leu or Phe"

(ix) FEATURE:
        (A) NAME/KEY: Modified-site
        (B) LOCATION: 144
        (D) OTHER INFORMATION: /product= "OTHER"
            /note= "Xaa = His or Val"

(xi) SEQUENCE DESCRIPTION: SEQ ID NO:3:

Xaa Ser Ala Gln Lys Arg Pro Ser Gln Xaa Xaa Lys Tyr Leu Ala Xaa
1               5                   10                  15

Ala Ser Thr Met Asp His Ala Arg His Gly Phe Leu Pro Arg His Arg
            20                  25                  30

Asp Thr Gly Ile Leu Asp Ser Xaa Gly Arg Phe Phe Gly Xaa Asp Arg
        35                  40                  45

Gly Ala Pro Lys Arg Gly Ser Gly Lys Asp Xaa His His Ala Ala Arg
    50                  55                  60

Thr Xaa His Tyr Gly Ser Leu Pro Gln Lys Xaa Gln Gly His Arg Xaa
65              70                  75                  80

Gln Asp Glu Asn Pro Val Val His Phe Phe Lys Asn Ile Val Thr Pro
                85                  90                  95

Arg Thr Pro Pro Ser Gln Gly Lys Gly Xaa Gly Leu Ser Leu Ser
            100                 105                 110

Arg Phe Ser Trp Gly Ala Glu Gly Gln Xaa Pro Gly Phe Gly Tyr Gly
        115                 120                 125

Gly Arg Ala Ser Asp Tyr Lys Ser Ala His Lys Gly Xaa Lys Gly Xaa
    130                 135                 140

Asp Ala Gln Gly Thr Leu Ser Lys Ile Phe Lys Leu Gly Gly Arg Asp
145                 150                 155                 160

Ser Arg Ser Gly Ser Pro Met Ala Arg Arg
                165                 170

(2) INFORMATION FOR SEQ ID NO:4:

(i) SEQUENCE CHARACTERISTICS:
    (A) LENGTH: 776 base pairs
    (B) TYPE: nucleic acid
    (C) STRANDEDNESS: single
    (D) TOPOLOGY: linear (ii) MOLECULE TYPE: DNA (ix) FEATURE:
    (A) NAME/KEY: -
    (B) LOCATION: 1..776
    (D) OTHER INFORMATION: /note= "I-b-A-alpha chain"

(xi) SEQUENCE DESCRIPTION: SEQ ID NO:4:

```
AATTCATGCC GCGCAGCAGA GCTCTGATTC TGGGGGTCCT CGCCCTGACC ACCATGCTCA      60
GCCTCTGTGG AGGTGAAGAC GACATTGAGG CCGACCACGT AGGCACCTAT GGTATAAGTG     120
TATATCAGTC TCCTGGAGAC ATTGGCCAGT ACACATTTGA ATTTGATGGT GATGAGTTGT     180
TCTATGTGGA CTTGGATAAG AAGGAGACTG TCTGGATGCT TCCTGAGTTT GGCCAATTGG     240
CAAGCTTTGA CCCCCAAGGT GGACTGCAAA ACATAGCTGT AGTAAAACAC AACTTGGGAG     300
TCTTGACTAA GAGGTCAAAT TCCACCCCAG CTACCAATGA GGCTCCTCAA GCGACTGTGT     360
TCCCCAAGTC CCCTGTGCTG CTGGGTCAGC CCAACACCCT CATCTGCTTT GTGGACAACA     420
TCTTCCCTCC TGTGATCAAC ATCACATGGC TCAGAAATAG CAAGTCAGTC GCAGACGGTG     480
TTTATGAGAC CAGCTTCTTC GTCAACCGTG ACTATTCCTT CCACAAGCTG TCTTATCTCA     540
CCTTCATCCC TTCTGACGAT GACATTTATG ACTGCAAGGT GGAACACTGG GGCCTGGAGG     600
AGCCGGTTCT GAAACACTGG GAACCTGAGA TTCCAGCCCC CATGTCAGAG CTGACAGAGA     660
CTGTGGTGTG TGCCCTGGGG TTGTCTGTGG GCCTTGTGGG CATCGTGGTG GGCACCATCT     720
TCATCATTCA AGGCCTGCGA TCAGGTGGCA CCTCCAGACA CCCAGGGCCT TTATGA         776
```

(2) INFORMATION FOR SEQ ID NO:5:

(i) SEQUENCE CHARACTERISTICS:
    (A) LENGTH: 702 base pairs
    (B) TYPE: nucleic acid
    (C) STRANDEDNESS: single
    (D) TOPOLOGY: linear (ii) MOLECULE TYPE: DNA (ix) FEATURE:
    (A) NAME/KEY: -
    (B) LOCATION: 1..702
    (D) OTHER INFORMATION: /note= "I-b-A-beta chain"

(xi) SEQUENCE DESCRIPTION: SEQ ID NO:5:

```
CATTTCGTGT ACCAGTTCAT GGGCGAGTGC TACTTCACCA ACGGGACGCA GCGCATACGA      60
TATGTGACCA GATACATCTA CAACCGGGAG GAGTACGTGC GCTACGACAG CGACGTGGGC     120
GAGCACCGCG CGGTGACCGA GCTGGGGCGG CCAGACGCCG AGTACTGGAA CAGCCAGCCG     180
GAGATCCTGG AGCGAACGCG GGCCGAGCTG GACACGGTGT GCAGACACAA CTACGAGGGG     240
CCGGAGACCC ACACCTCCCT GCGGCGGCTT GAACAGCCCA ATGTCGTCAT CTCCCTGTCC     300
AGGACAGAGG CCCTCAACCA CCACAACACT CTGGTCTGCT CAGTGACAGA TTTCTACCCA     360
GCCAAGATCA AAGTGCGCTG GTTCCGGAAT GGCCAGGAGG AGACGGTGGG GGTCTCATCC     420
ACACAGCTTA TTAGGAATGG GGACTGGACC TTCCAGGTCC TGGTCATGCT GGAGATGACC     480
CCTCGGCGGG GAGAGGTCTA CACCTGTCAC GTGGAGCATC CCAGCCTGAA GAGCCCCATC     540
ACTGTGGAGT GGAGGGCACA GTCTGAGTCT GCCTGGAGCA AGATGTTGAG CGGCATCGGG     600
```

```
GGCTGCGTGC TTGGGGTGAT CTTCCTCGGG CTTGGCCTTT TCATCCGTCA CAGGAGTCAG      660

AAAGGACCTC GAGGCCCTCC TCCAGCAGGG CTCCTGCAGT GA                         702
```

(2) INFORMATION FOR SEQ ID NO:6:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

```
Asp Thr Pro Tyr Leu Asp Ile Thr Tyr His Phe Ile Met Gln Arg Ile
1               5                   10                  15

Pro Leu Tyr Phe Val
            20
```

(2) INFORMATION FOR SEQ ID NO:7:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

```
GACACCCCGT ACCTGGACAT CACCTACCAC TTCATCATGC AGCGTATCCC GCTGTACTTC      60

CTG                                                                    63
```

(2) INFORMATION FOR SEQ ID NO:8:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = N-acetyl alanine"

(xi) SEQUENCE DESCRIPTION: SEQ ID NO:8:

```
Xaa Ser Gln Lys Arg Pro Ser Gln Arg His Gly Ser Lys
1               5                   10
```

(2) INFORMATION FOR SEQ ID NO:9:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = N-acetyl phenylalanine"

-continued

```
    (ix) FEATURE:
         (A) NAME/KEY: Modified-site
         (B) LOCATION: 12
         (D) OTHER INFORMATION: /product= "OTHER"
             /note= "Xaa = prolinamide"

(xi) SEQUENCE DESCRIPTION: SEQ ID NO:9:

Xaa Phe Lys Asn Ile Val Thr Pro Arg Pro Pro Xaa
1               5                  10

(2) INFORMATION FOR SEQ ID NO:10:

(i) SEQUENCE CHARACTERISTICS:
         (A) LENGTH: 17 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:10:

Tyr Ala Ile Val His Met Thr Lys Leu Leu Leu Asp Tyr Pro Gly Lys
1               5                  10                  15

Ile
```